United States Patent [19]
Henniges et al.

[11] Patent Number: 5,645,540
[45] Date of Patent: Jul. 8, 1997

[54] BLOOD CONSERVATION SYSTEM

[75] Inventors: Bruce D. Henniges; Kurt J. Kuipers; Richard F. Huyser, all of Kalamazoo, Mich.

[73] Assignee: Stryker Corporation, Kalamazoo, Mich.

[21] Appl. No.: 320,940

[22] Filed: Oct. 11, 1994

[51] Int. Cl.$^6$ .................................................. A61M 1/00
[52] U.S. Cl. .............................. 604/320; 604/35; 604/73; 604/118; 604/319
[58] Field of Search ............................. 604/4–7, 35, 67, 604/73, 118, 319, 320, 322, 327, 356

[56] References Cited

U.S. PATENT DOCUMENTS

| | | |
|---|---|---|
| Re. 29,321 | 7/1977 | Holbrook . |
| 2,397,257 | 3/1946 | Goland . |
| 2,646,042 | 7/1953 | Hu . |
| 3,363,626 | 1/1968 | Bidwell . |
| 3,492,991 | 2/1970 | Dyer . |
| 3,515,127 | 6/1970 | Reymond . |
| 3,545,440 | 12/1970 | Mishkin et al. . |
| 3,565,076 | 2/1971 | Kaden . |
| 3,572,340 | 3/1971 | Lloyd et al. . |
| 3,585,995 | 6/1971 | Perkins et al. . |
| 3,675,653 | 7/1972 | Crowley et al. . |
| 3,719,197 | 3/1973 | Pannier, Jr. et al. . |
| 3,738,775 | 6/1973 | Strickland . |
| 3,768,478 | 10/1973 | Fertik et al. . |
| 3,799,702 | 3/1974 | Weishaar . |
| 3,807,401 | 4/1974 | Riggle et al. . |
| 3,855,997 | 12/1974 | Sauer ........................... 604/319 |
| 3,896,733 | 7/1975 | Rosenberg . |
| 3,918,453 | 11/1975 | Leonard . |
| 3,933,150 | 1/1976 | Kaplan et al. . |
| 3,955,574 | 5/1976 | Rubinstein . |
| 3,965,896 | 6/1976 | Swank . |
| 3,982,538 | 9/1976 | Sharpe . |
| 3,993,062 | 11/1976 | Jess . |
| 3,993,067 | 11/1976 | Schachet et al. . |
| 4,014,329 | 3/1977 | Welch et al. . |
| 4,022,209 | 5/1977 | Nehring . |
| 4,073,294 | 2/1978 | Stanley et al. . |
| 4,111,204 | 9/1978 | Hessel . |

(List continued on next page.)

FOREIGN PATENT DOCUMENTS

| | | |
|---|---|---|
| 2 058 227 | 4/1981 | United Kingdom . |
| WO8002706 | 12/1980 | WIPO . |

OTHER PUBLICATIONS

Copy of Swank article entitled "Alteration of Blood On Storage: Measurement of Adhesiveness of Aging Platelets and Leukocytes And Their Removal By Filtration", *The New England Journal of Medicine*, vol. 265, No. 15, Oct. 12, 1961, pp. 728–733.
Richards Solcotrans Plus Orthopaedic Drainage/Reinfusion System ST 6000 Series Brochure.
The Solcotrans Orthopaedic Autotransfusion System Brochure.
DePuy Closed Wound Drainage System Brochure.
Autovac 7900 Series B Boehringer Brochure.
Assessment of an Autotransfusion Device for Collection of Blood Researchers Ralph Bernstein and David Albert.
Stryker Surgical 215–28 ConstaVac Brochure (Maintenance Manual & Operating Instructions).
Orthophaedic Autotransfustion System Orth–evac Brochure.
Richards Solotrans Plus Drainage/Reinfusion System ST 6000 Series Brochure.

*Primary Examiner*—Michael J. Milano
*Attorney, Agent, or Firm*—Flynn, Thiel, Boutell & Tanis, P.C.

[57] ABSTRACT

A blood conservation system, including a vacuum wound drainage apparatus, comprises a liquid collection reservoir for a wound to be drained and an operating unit fixed on such reservoir. The operating unit is self contained and includes a battery supply, an electric motor powered pump, a control for setting the level of vacuum desired in the reservoir and structure for operating the motor powered vacuum pump in accord with the setting of the control. The entire system is arranged to be disposed of after use by one patient.

32 Claims, 35 Drawing Sheets

U.S. PATENT DOCUMENTS

| | | | |
|---|---|---|---|
| 4,157,967 | 6/1979 | Meyst et al. . | |
| 4,184,510 | 1/1980 | Murry et al. . | |
| 4,212,589 | 7/1980 | Bosio | 604/4 |
| 4,219,177 | 8/1980 | O'Day | 604/322 |
| 4,228,798 | 10/1980 | Deaton . | |
| 4,256,109 | 3/1981 | Nichols . | |
| 4,261,360 | 4/1981 | Perez . | |
| 4,306,558 | 12/1981 | Kurtz et al. . | |
| 4,345,342 | 8/1982 | Saito . | |
| 4,392,858 | 7/1983 | George et al. . | |
| 4,395,258 | 7/1983 | Wang et al. . | |
| 4,401,566 | 8/1983 | Igari et al. . | |
| 4,424,053 | 1/1984 | Kurtz et al. . | |
| 4,443,220 | 4/1984 | Hauer et al. . | |
| 4,445,884 | 5/1984 | Kurtz et al. . | |
| 4,465,485 | 8/1984 | Kashmer et al. . | |
| 4,487,606 | 12/1984 | Leviton et al. . | |
| 4,500,308 | 2/1985 | Kurtz et al. . | |
| 4,501,581 | 2/1985 | Kurtz et al. . | |
| 4,516,973 | 5/1985 | Telang . | |
| 4,540,406 | 9/1985 | Miles . | |
| 4,540,413 | 9/1985 | Russo . | |
| 4,547,186 | 10/1985 | Bartlett . | |
| 4,551,131 | 11/1985 | Miles et al. . | |
| 4,561,558 | 12/1985 | Richman et al. . | |
| 4,561,868 | 12/1985 | von Reis et al. . | |
| 4,564,359 | 1/1986 | Rühland . | |
| 4,569,674 | 2/1986 | Phillips et al. . | |
| 4,573,992 | 3/1986 | Marx . | |
| 4,631,050 | 12/1986 | Reed et al. . | |
| 4,634,430 | 1/1987 | Polaschegg | 604/141 |
| 4,642,088 | 2/1987 | Günter . | |
| 4,642,093 | 2/1987 | Härle . | |
| 4,655,740 | 4/1987 | Rühland . | |
| 4,655,754 | 4/1987 | Richmond et al. . | |
| 4,671,786 | 6/1987 | Krug . | |
| 4,744,785 | 5/1988 | Rosenthal et al. . | |
| 4,767,417 | 8/1988 | Boehringer et al. . | |
| 4,772,256 | 9/1988 | Lane et al. . | |
| 4,775,360 | 10/1988 | Lane et al. . | |
| 4,781,707 | 11/1988 | Boehringer et al. . | |
| 4,826,494 | 5/1989 | Richmond et al. . | |
| 4,994,022 | 2/1991 | Steffler et al. . | |
| 5,061,242 | 10/1991 | Sampson | 604/118 |
| 5,098,386 | 3/1992 | Smith | 604/152 |
| 5,133,703 | 7/1992 | Boehringer et al. . | |
| 5,156,602 | 10/1992 | Steffler . | |
| 5,227,049 | 7/1993 | Chevallet et al. | 210/97 |
| 5,279,550 | 1/1994 | Habib et al. . | |
| 5,304,164 | 4/1994 | Lindsay | 604/403 |
| 5,380,308 | 1/1995 | Gunya et al. | 604/323 |

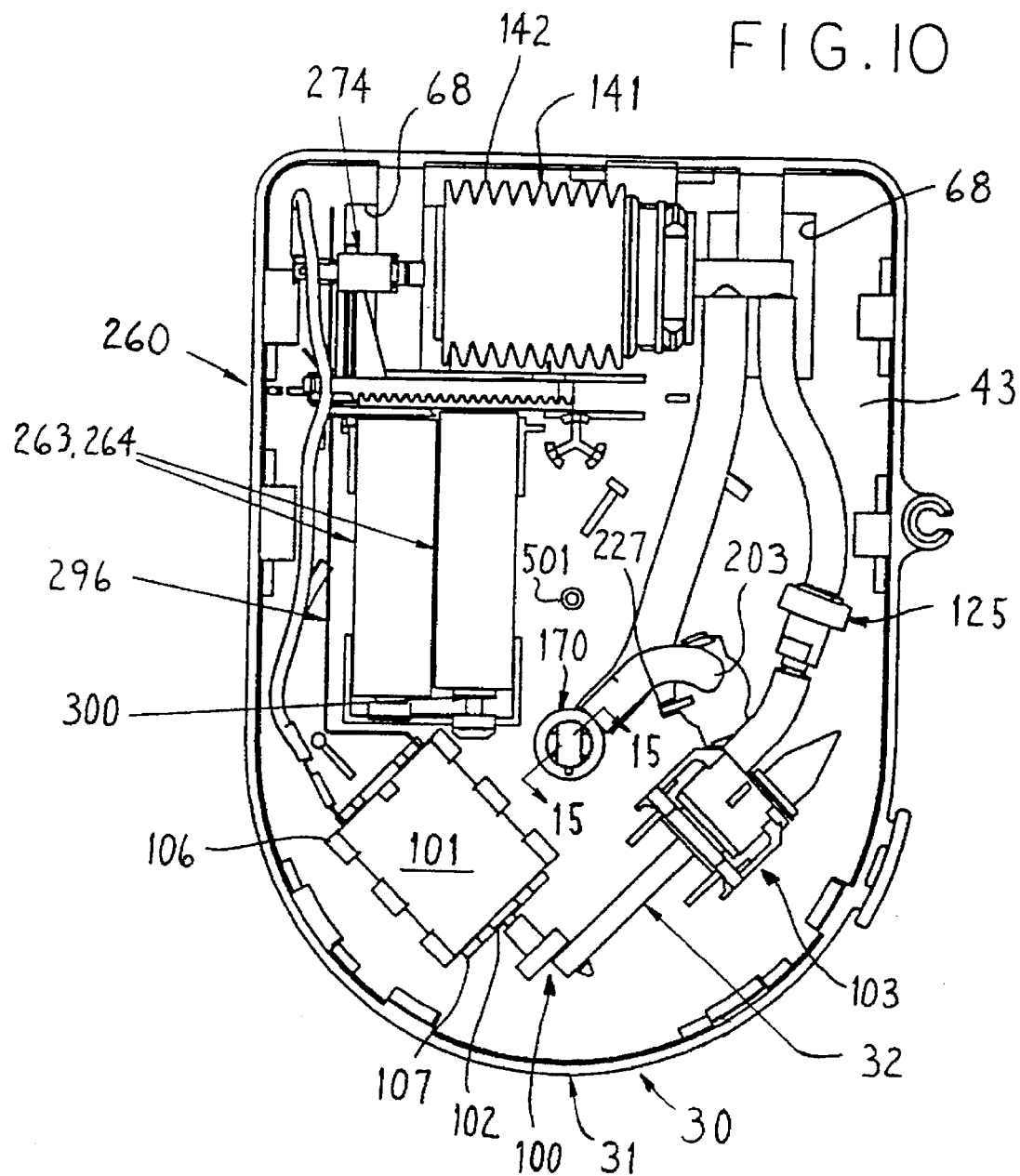

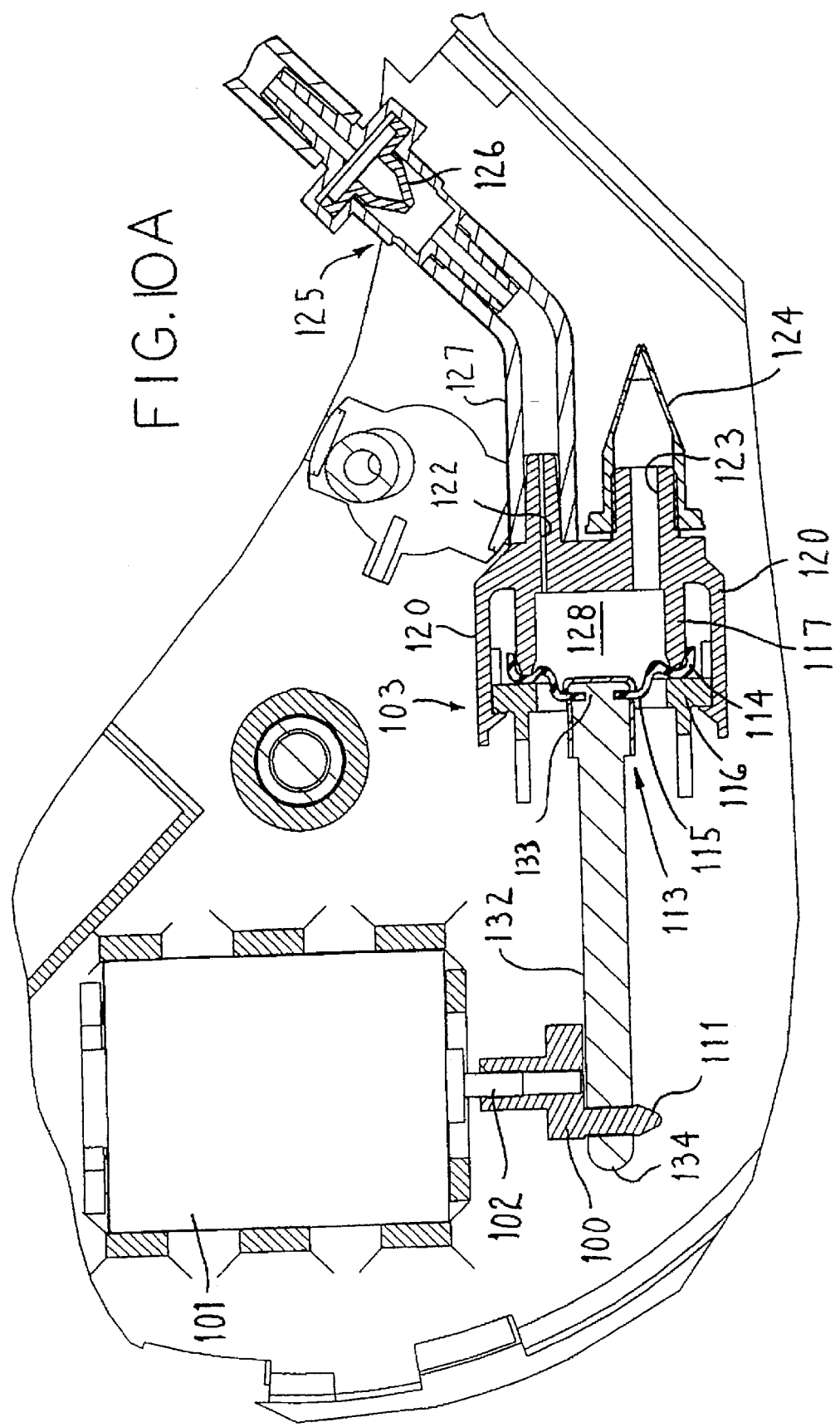

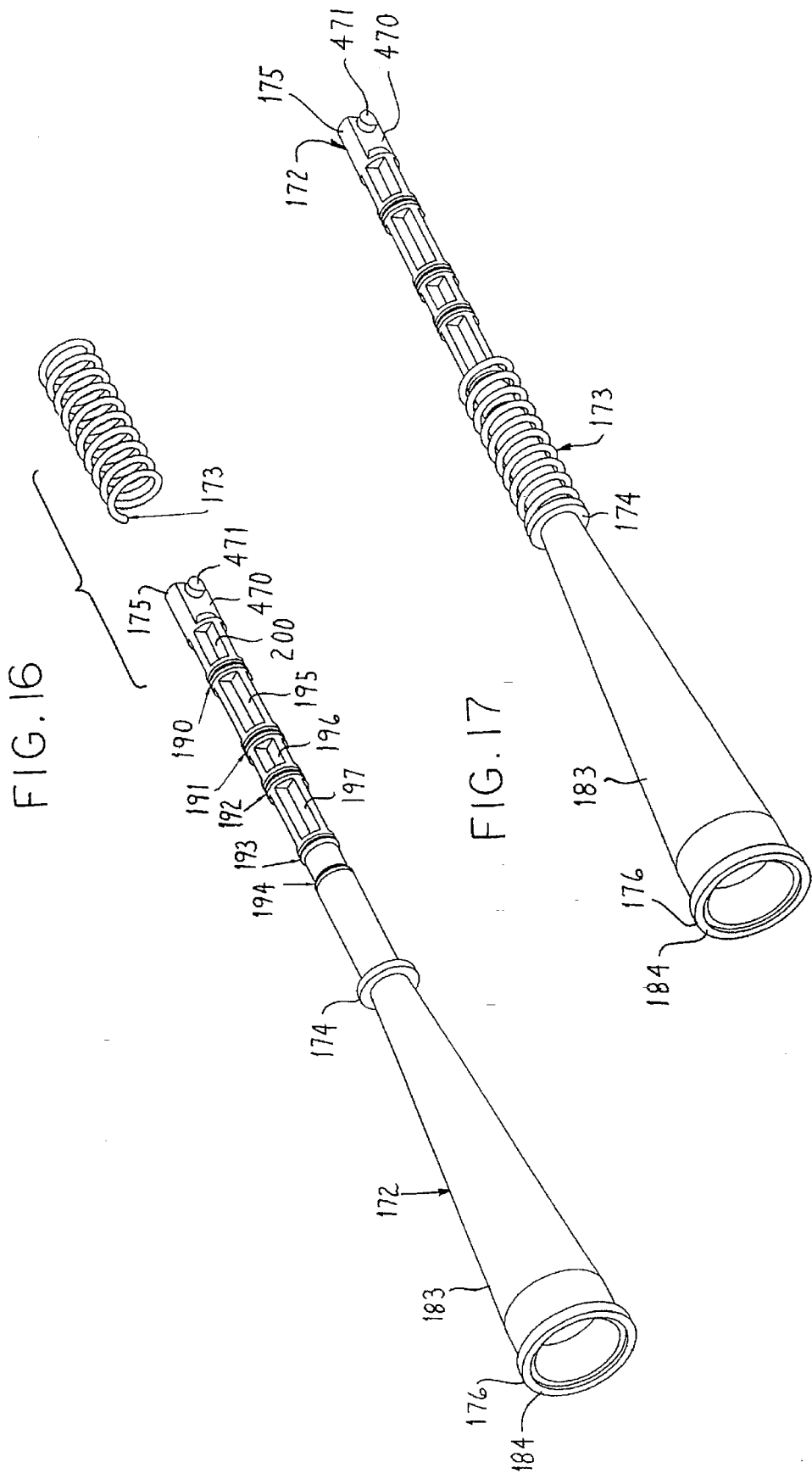

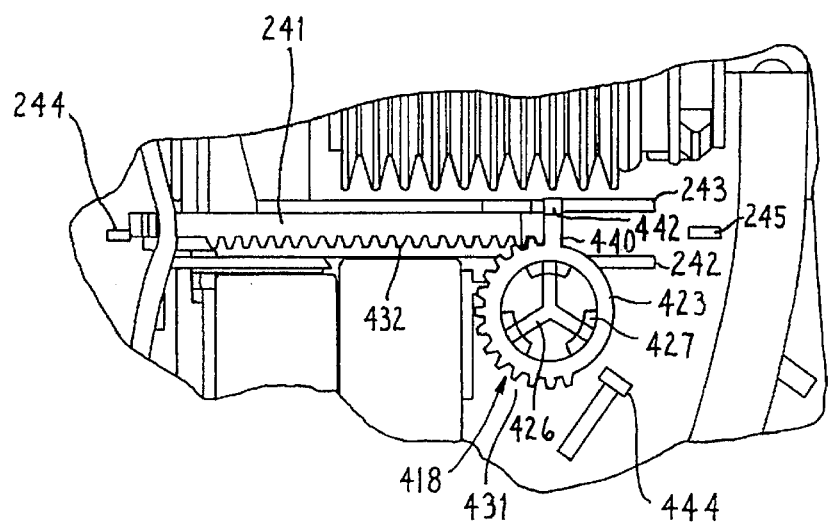
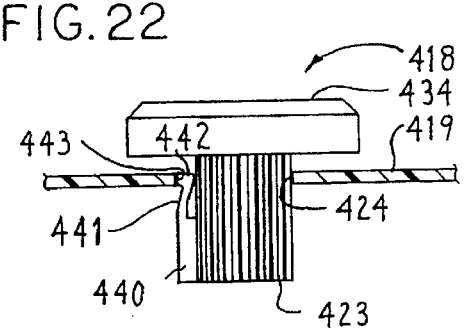
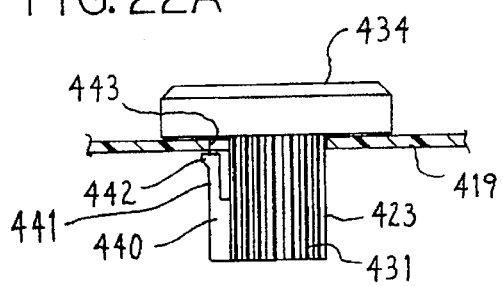
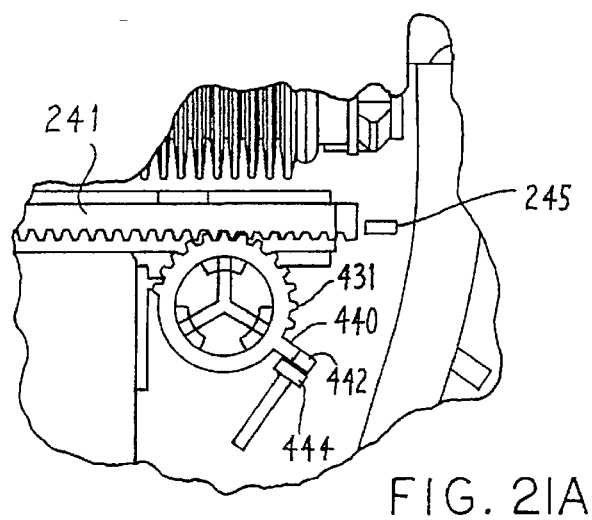

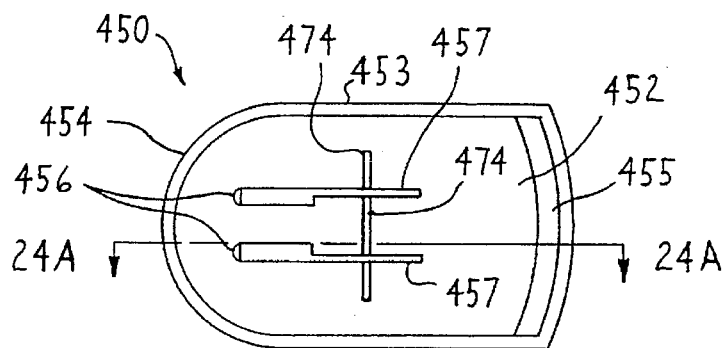
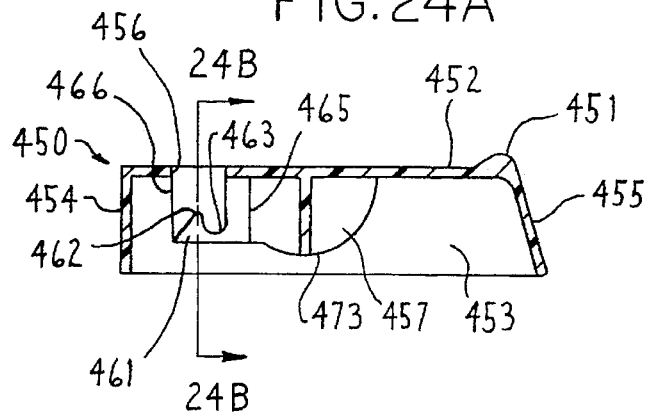
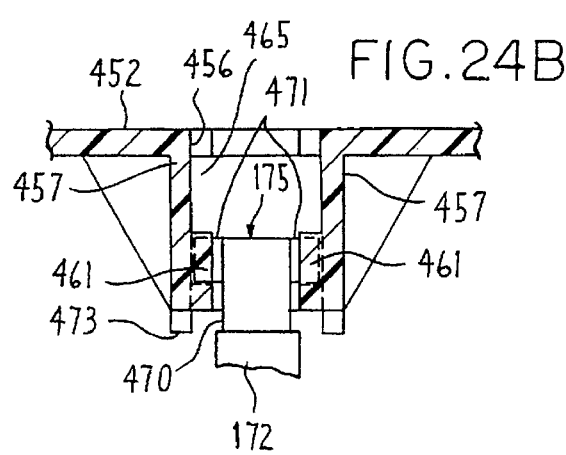
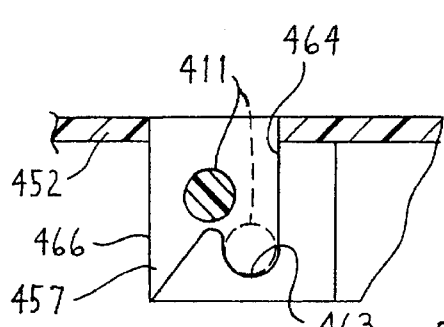

BLOOD CONSERVATION SYSTEM

FIELD OF THE INVENTION

This invention relates to a blood conservation system, including apparatus adapted for suction wound drainage.

BACKGROUND OF THE INVENTION

U.S. Pat. Nos. 5,156,602 (Steffler), 4,994,022 (Steffler et al), 4,826,494 (Richmond et al), 4,655,754 (Richmond et al) and 4,569,674 (Phillips et al), assigned to the Assignee of the present invention, disclose suction wound drainage systems and/or blood conservation systems which have been operationally and commercially successful. The present invention arises from a continuing effort to improve on an apparatus of this general type.

The objects and purposes of this invention include provision of apparatus for suction wound drainage and particularly adapted for blood conservation, especially under postoperative conditions.

SUMMARY OF THE INVENTION

A blood conservation system, including a vacuum wound drainage apparatus, comprises a liquid collection reservoir for a wound to be drained and an operating unit fixed on such reservoir. The operating unit is self-contained and includes a battery supply, an electric motor powered pump, a control for setting the level of vacuum desired in the reservoir and structure for operating the motor powered vacuum pump in accord with the setting of the control. The entire system is arranged to be disposed of after single patient use.

Further objects and purposes of the invention will be apparent to persons acquainted with apparatus of this general type upon reading the following specification and inspecting the accompanying drawings.

BRIEF DESCRIPTION OF THE DRAWINGS

A preferred embodiment of the invention is described in detail hereinafter with reference to the accompanying drawings, in which:

FIG. 5 is a fragmentary right side elevational view of the FIG. 2 system partly broken away to show structure for supporting same on a bed rail or the like;

FIG. 10 is a top view of the FIG. 2 system with the cover removed.

FIG. 10A is an enlarged fragment of the motor and pump of FIG. 10 partially broken to show the pump in central cross-section from above;

FIG. 16 is an exploded pictorial view of the valve plunger and closure spring of FIG. 15;

FIG. 17 is a view similar to FIG. 16 with the closure spring installed on the valve plunger;

FIG. 21 is an enlarged fragment of FIG. 10 showing the tubular pinion installed on the base, with its overlying knob removed for better visibility, and with the slider located outboard to return the reservoir to atmospheric pressure;

FIG. 21A is a view similar to FIG. 21 but with the pinion and slider positioned inboard for maximum evacuation of the reservoir;

FIG. 22 is a fragmentary enlarged sectional view substantially taken on the line 22—22 of FIG. 20A with the knob and tubular pinion partly installed on the top wall of the cover;

FIG. 22A is a view similar to FIG. 22 but with the knob and tubular pinion fully installed on the top wall of the cover;

FIG. 24 is a bottom view of the vacuum control lever of FIG. 23;

FIG. 24A is a central cross-sectional view of the vacuum control lever substantially taken on the line 24A—24A of FIG. 24;

FIG. 24B is an enlarged fragmentary sectional view substantially as taken on the line 24B—24B of FIG. 24A;

FIG. 24C is an enlarged fragment of FIG. 24A showing alternate positions of the vacuum plunger pivot pin during and after installation with respect to the valve lever of FIG. 24.

DETAILED DESCRIPTION

Figure 1:
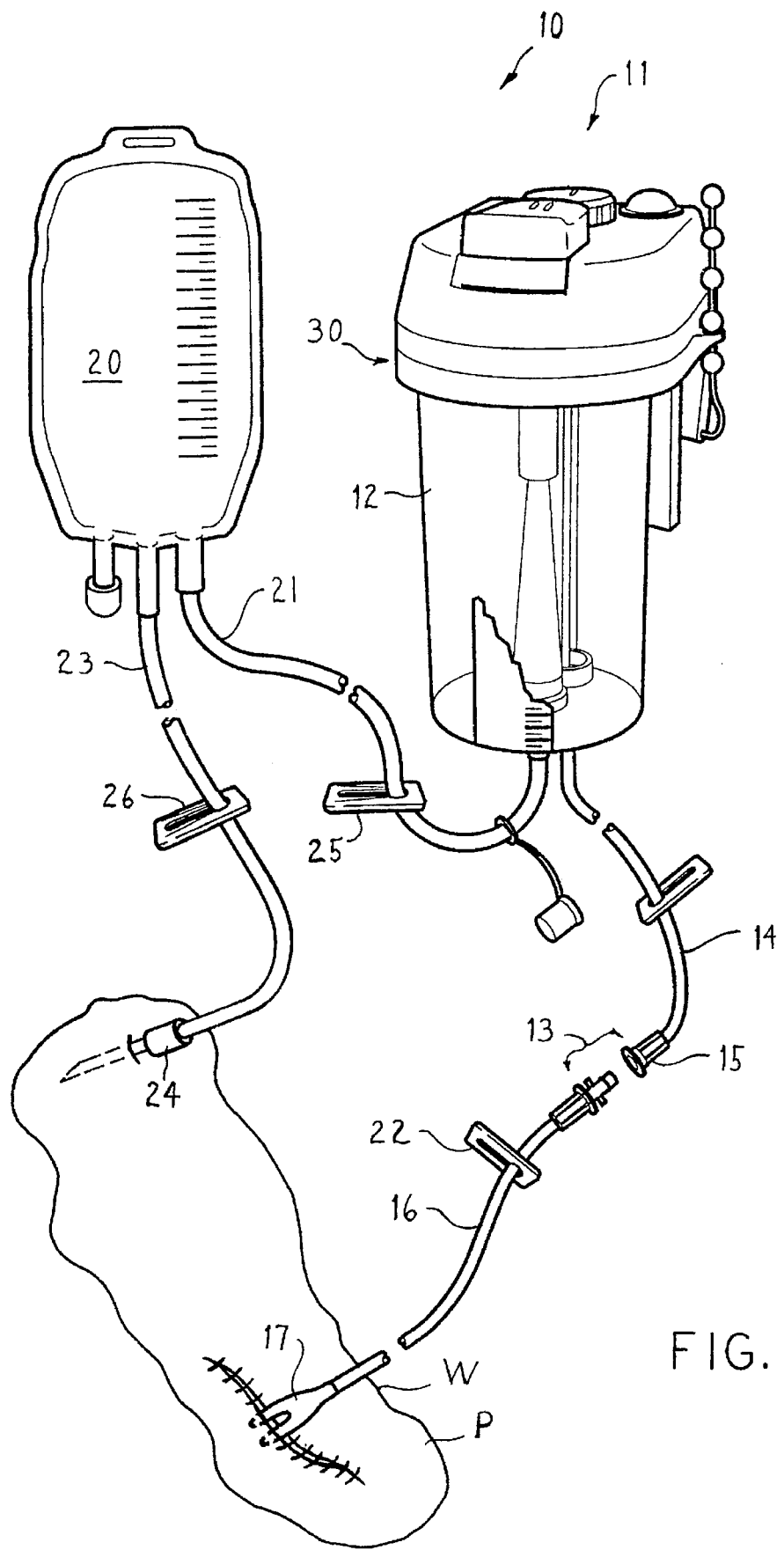
FIG. 1 is a somewhat schematic view of liquid connections of a system embodying the present invention.

A system 10 (FIG. 1) embodying the invention comprises a blood collection and conservation apparatus 11 including a reservoir 12 into which is drawn, under suction, blood draining from a post operative surgical wound W on a patient P recovering from surgery. The partially evacuated reservoir 12 is connected to the wound W through a flexible collection tubing set 13, here comprising, for example, a tube 14, bayonet-type connector 15, further tube 16 and dual port collector 17 conventionally inserted in the surgical wound in the manner of a conventional drainage tube. Blood may be emptied from the reservoir 12 into a conventional storage container, such as a conventional blood bag 20 through an outlet tube 21, after removal of suction from (restoring of atmospheric pressure) in the reservoir 12. Blood thus stored in the blood bag 20 can thereafter be returned to the patient from the blood bag 20, as through a conventional filter (not shown) and transfusion kit here represented in part by a return tube 23 connected back to the patient P intravenously by a conventional intravenous cannula 24. The tubes 16, 21 and 23 are selectively closable by conventional means such as conventional slide clamps 22, 25 and 26, respectively.

To the extent above described, the system 10 is conventional and similar to that disclosed and claimed in U.S. Pat. No. 4,994,022 (Steffler, et al) assigned to the Assignee of the present invention and marketed under the model designation CBC (TM).

Turning now more particularly to aspects of the present invention, the blood collection apparatus 11 comprises a self-contained, self-powered, suction supply and control assembly 30 (FIGS. 1 and 2) comprising a plate-like base 31 covered by an inverted cup shaped, downward opening cover 32. The base 31 and cover 32 are generally rectangular in plan (as seen from above) with conforming perimeters, and each has a generally rounded front end portion in the preferred embodiment shown, as indicated at 33 in FIG. 6, looking upward under the base 31.

Figure 4:
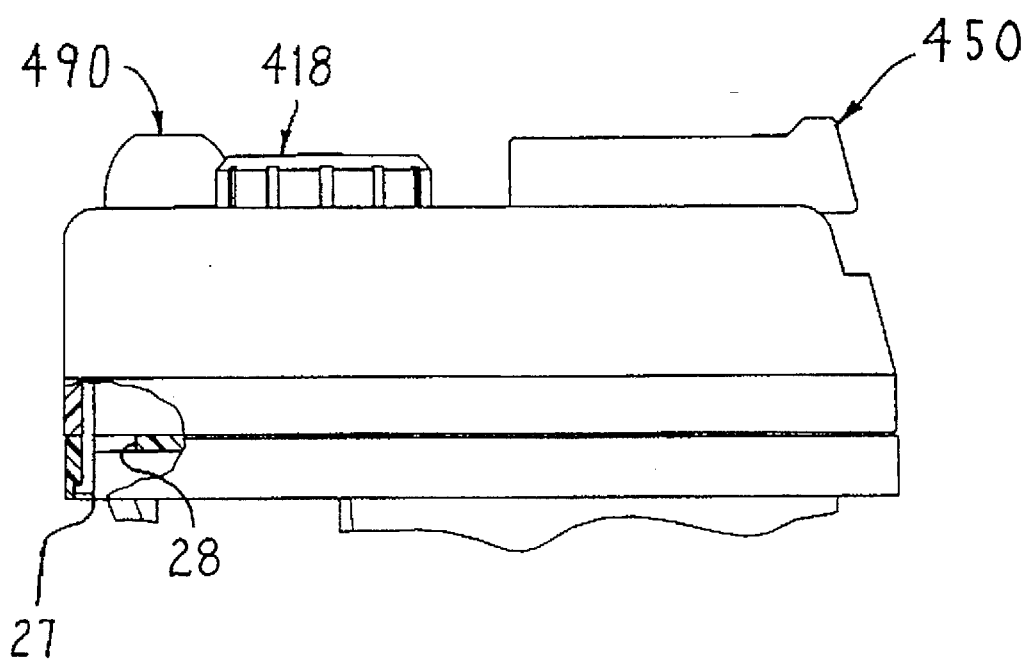
FIG. 4 is a fragmentary left side elevational view of the FIG. 2 system.

The cover 32 snap fits snug atop the base 31 in a fixed but preferably removable manner by means of springy L-shaped tongues 27 depending (preferably integrally) from the bottom edge of the cover 32 and snap fitted into slots 28 near the perimeter of the base 31 (FIG. 4).

Figure 2:
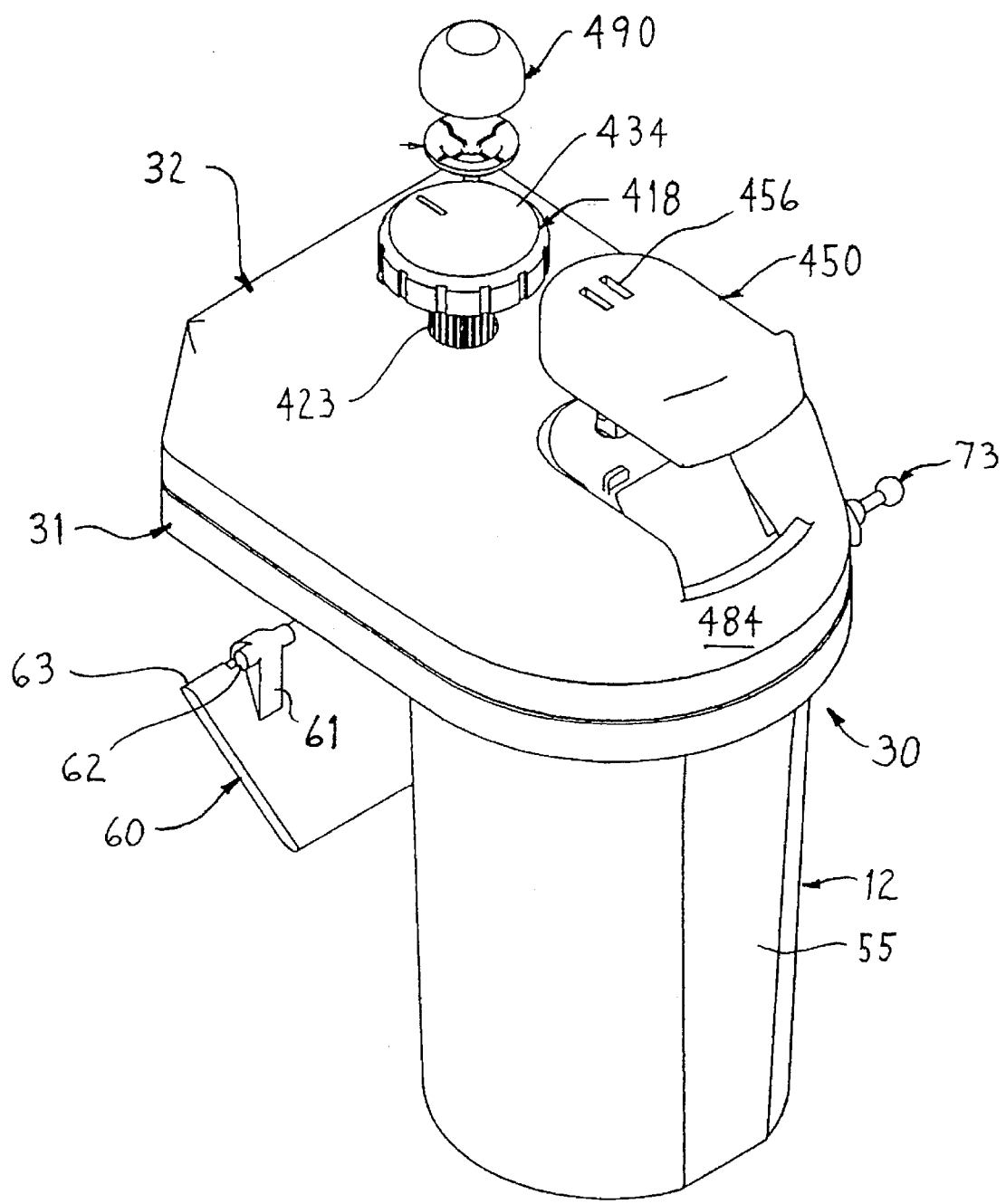
FIG. 2 is a partly exploded pictorial view of a blood collection and conservation apparatus of FIG. 1.
Figure 6:
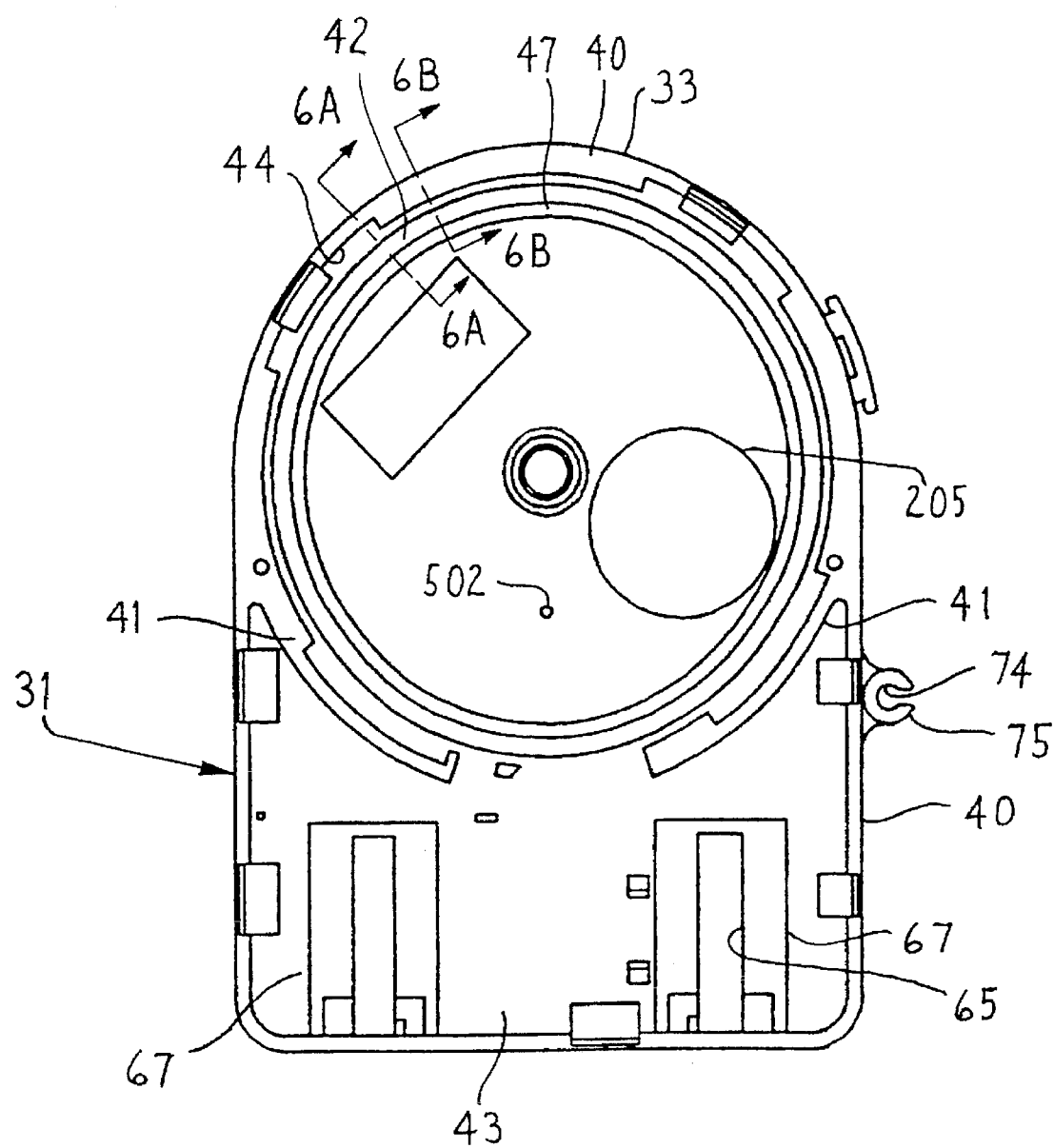
FIG. 6 is a bottom view of the FIG. 2 suction and control assembly base with the reservoir removed.
Figure 6A:
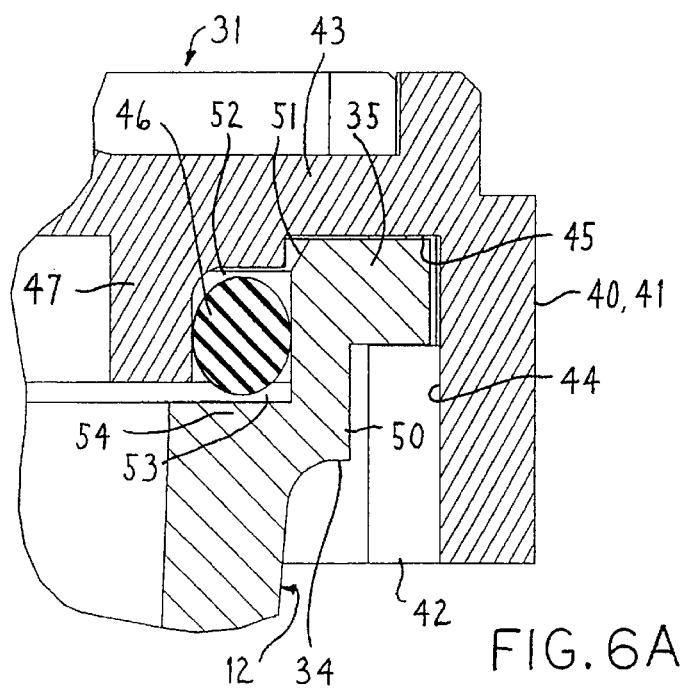
FIG. 6A is a fragmentary enlarged sectional view substantially taken on the line 6A—6A of FIG. 6.

The reservoir 12 is a relatively tall, upward opening, slightly downward tapered, generally cup shaped member releasably and fixedly sealingly depending from the front end portion of the base 31 as seen for example in FIG. 2. The top of the reservoir 12 is releasably fixed to the underside of the base 31 by a bayonet type connection requiring the reservoir 12 to be pushed upward toward the underside of the base 31 and twisted slightly in a tightening direction. Release of the reservoir 12 from the base 31 is by an opposite twist and drop motion of the reservoir 12 with respect to the base 31. To this end, the reservoir 12 upper end is provided with a substantially L-cross section, radially outward and upward stepped rim 34 circumferentially therearound (FIGS. 6, 6A, 6B, and 7). Radially outwardly extending, circumferentially spaced ears 35 are fixed at the top edge of the rim 34 of the reservoir 12. The base 31 has a depending perimeter flange 40. The perimeter flange 40 has semi-circular spurs 41 (FIG. 6) which angle toward the central portion of the underside of the base in a generally convergent manner, as see in FIG. 6, and with the rounded front portion of such perimeter flange 40, define a circle shaped, almost circumferentially complete, slightly open flange structure. The depending flange 40 and semi-circular spurs 41 thereof have circumferentially spaced, radiating inward extending ledges 42 spaced below the generally plate-like, normally horizontal floor 43 of the base 31. The ledges 42 are circumferentially separated by circumferential spaces 44 (FIGS. 6 and 6A).

Accordingly, on pushing the reservoir 12 upward against the underside of the base 31, adjacent to the front of the base, the reservoir ears 35 can upwardly enter the circumferential spaces 44. Thereafter, rotation (here clockwise as seen from below) of the reservoir angularly moves each ear 35 into an annular space 45 (FIGS. 6A and 6B) above a corresponding ledge 42 in a snug but circumferentially reversible manner, to establish the aforementioned bayonet connection of the top of the reservoir 12 to the underside of the base 31.

Figure 6C:
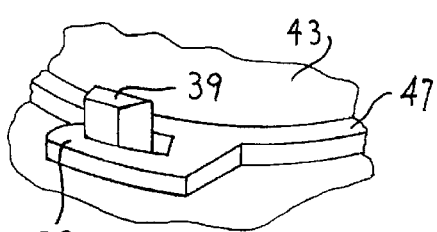
FIG. 6C is an enlarged fragment of FIG. 6 showing the resilient latch for blocking unintended loosening of the reservoir from the overlying base.
Figure 6B:
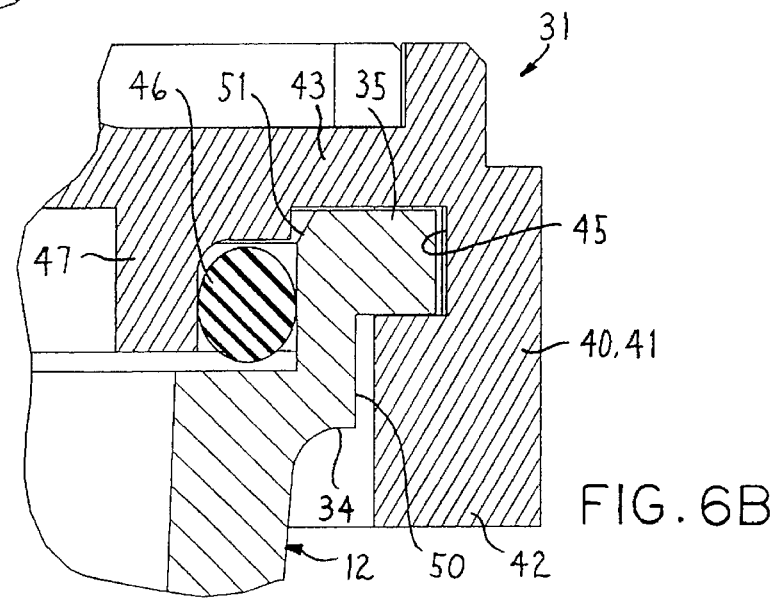
FIG. 6B is a fragmentary enlarged sectional view substantially taken on the line 6B—6B of FIG. 6.

A releasable latch may be provided to positively block accidental rotation of the reservoir 12 out of its bayonet connection to the underside of the base 31. Here, for example, a springy finger 38 (FIG. 6C) fixed preferably integrally on the upper run of the reservoir 12 snaps releasably over a block 39 depending integrally from the floor 43 of the base 31.

An annular airtight vacuum seal is provided between the top of the reservoir 12 and the underside of the base 31. To this end, an annular resilient seal (preferably an O-ring) 46 (FIGS. 6A, 6B and 7) snugly surrounds, in slightly stretched but releasable and frictionally clinging fashion, a circular flange 47 depending from the underside of the floor 43 of base 31, coaxial with and radially spaced inward from the rounded front portion of the perimeter flange 40 and its continuing, generally converging, semi-circular spurs 41 and the radially inward ledges 42. As the reservoir 12 is pushed up into engagement with the underside of the base 31, the upstanding circular part 50 of the rim 34 thereof slides upwards snugly over the O-ring 46 and cooperates with the depending circular flange 47 of the base 31 to radially crush the O-ring 46 sufficient to establish a tight vacuum seal between the base depending flange 47 and reservoir upstanding rim part 50, and hence between the base 31 and reservoir 12, thereby effectively sealing the top of the reservoir 12. To facilitate upward movement of the upstanding part 50 of the reservoir rim 34 past the outside of the O-ring 46, the upper portion of the upstanding part 50 is preferably chamfered, as indicated at 51 in FIGS. 6A and 6B. In one unit built according to the invention, the O-ring had a cross-sectional diameter of about 0.139 inch and was subjected to a radial crush, between the flange 47 and upstanding part 50 of about 0.013 inch. To put this in some degree of scale, the same unit built according to the invention had a reservoir 12 about 6 inches high fitted to a base 31 approximately 4½ inches wide by 6 inches long.

The radially directed crush of the O-ring 46 is advantageous in requiring much less axial force on the reservoir against the bottom of the base 31 during installation than would a corresponding axially directed crush of the O-ring, for the same sealing effect. Thus, the reservoir 12, under the present invention, is much easier to install and remove with respect to the base 31 than would have been the case given an O-ring crush in the axial direction of the reservoir 12, for the same sealing effect of the O-ring with respect to the reservoir 12 and base 31. In this respect, note in FIG. 6A the top and bottom clearances 52 and 53 of the O-ring 46 with respect to the overlying floor 43 of the base 31 and underlying radial portion 54 of the reservoir rim 34, showing no axial crush.

The front of the reservoir 12 has a chordal flat 55 (FIG. 2) for identifying the front of the reservoir and also for carrying a numbered liquid level scale (not shown), for example measured in hundreds of cc's, in the form of an adhered label or, if desired, molded-in scale.

Figure 3:
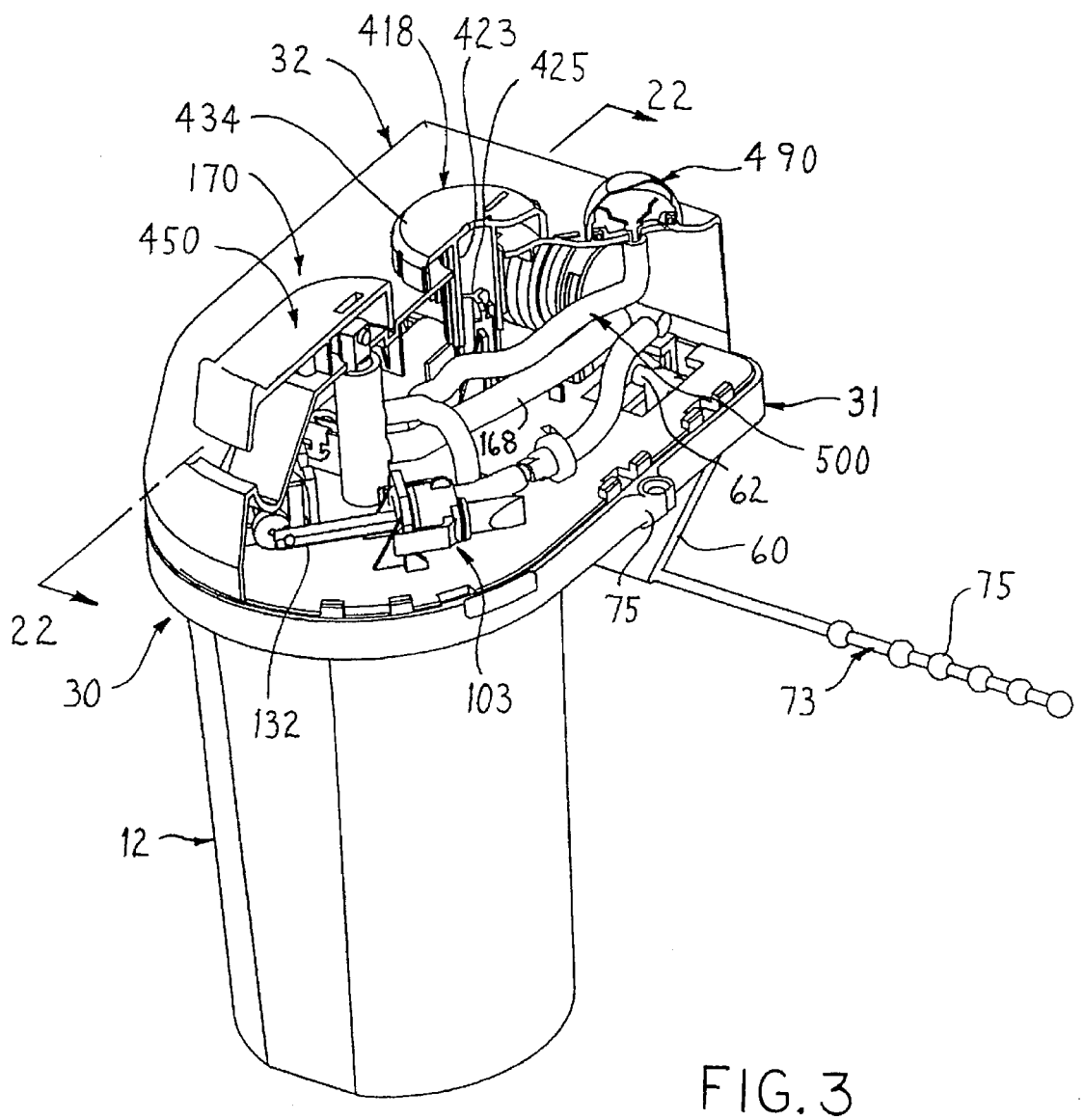
FIG. 3 is a partially broken pictorial view of the FIG. 2 system.
Figure 5:
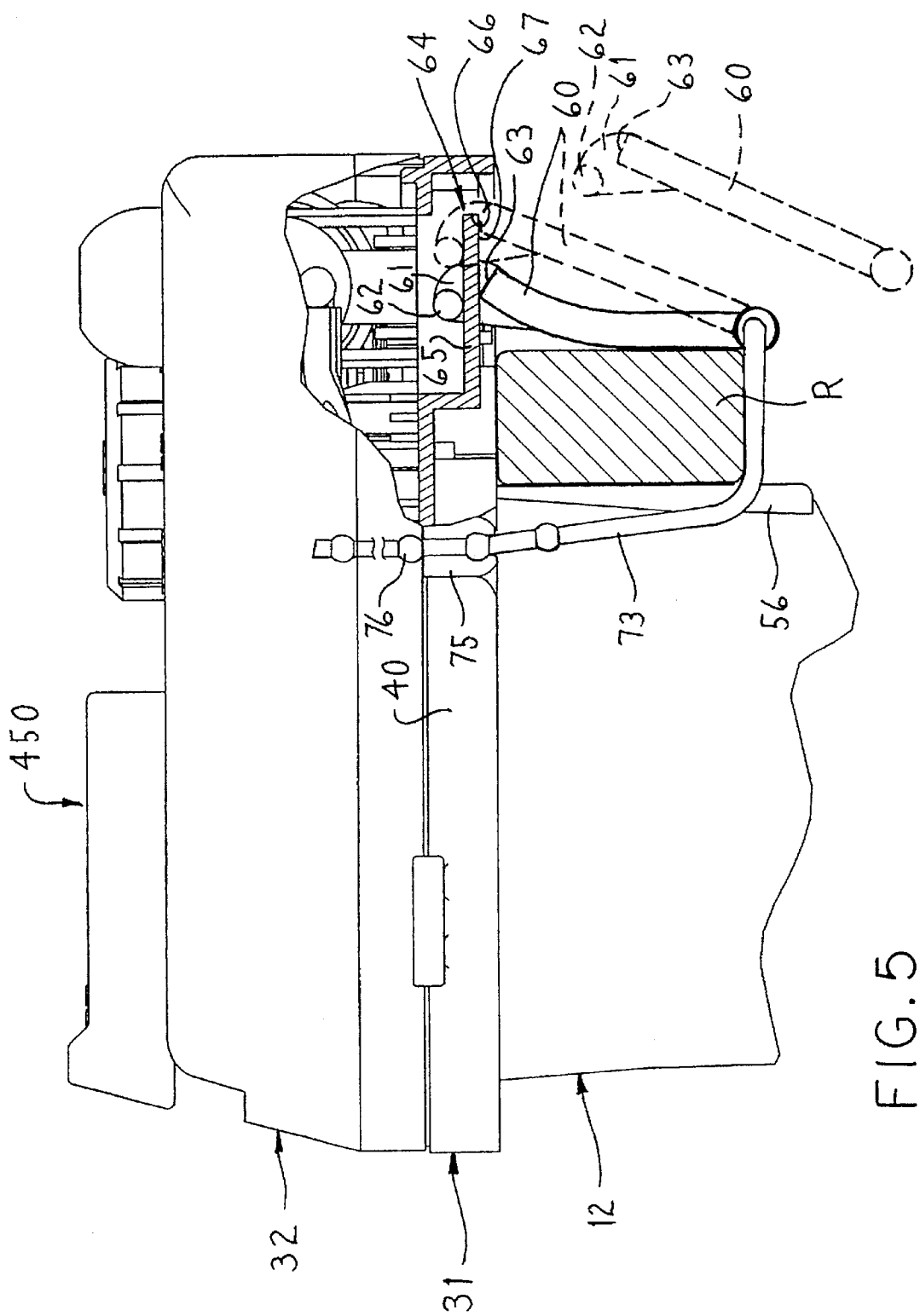
Figure 8:
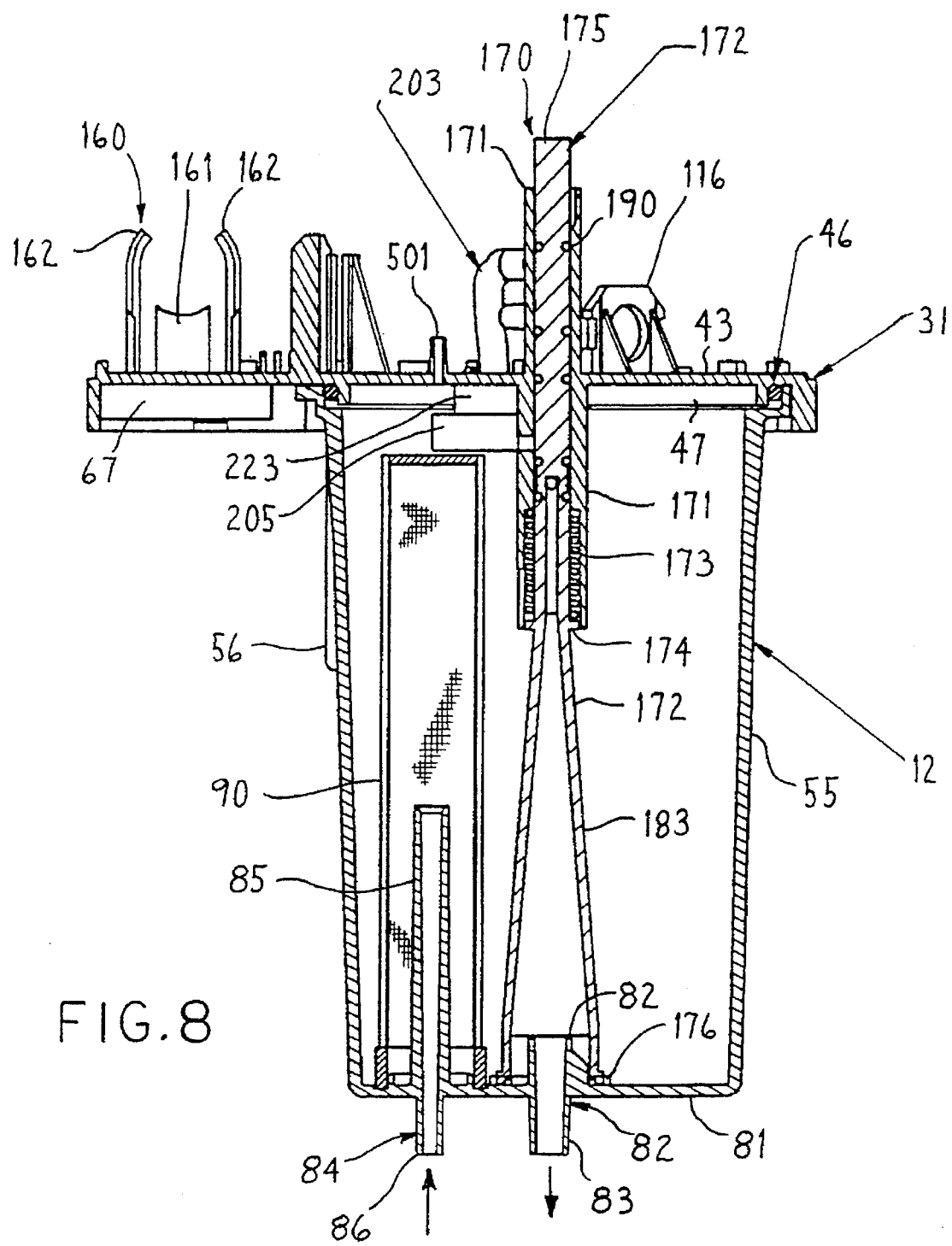
FIG. 8 is a central cross-sectional view substantially taken on the line 8—8 of FIG. 7.

The upper portion of the back of the reservoir 12 carries axially extending ribs 56 (FIG. 8). The rear portion of the base 31 projects rearwardly beyond the top of the reservoir 12 and is adapted to rest upon a substantially horizontal member located adjacent to the patient, such as a hospital bed rail R, for supporting the apparatus 10 in a stable but removable manner, with the reservoir 12 upright, as generally indicated in FIGS. 2, 3 and 5. To this end, the ribs 56 on the back of the reservoir 12 upper portion engage the front of bed rail R supporting the rear portion of the base 31, with the upright reservoir 12 and front part of the base 31 and cover 32 projecting forwardly from the rail R.

To releasably retain the apparatus 10 fixedly upright on the rail R, an almost rigid, slightly elastically bendable paddle 60, preferably of a rubber-like plastics material, removably depends from the rear portion of the base 31 behind the rail R. The paddle 60 is of generally rectangular shape and has a pair of laterally spaced arms 61 extending up from the top edge thereof, the arms being provided with preferably integral, fixed, opposite laterally extending, stub pins 62 extending substantially parallel to the top edge 63 of the paddle 60 but offset slightly forwarded of the plane of the paddle 60. The arms 61 are each generally L-shaped in a plane substantially perpendicular to the plane of the paddle. The arms each can thus be described as being rigidly shouldered fixedly on the top edge of the paddle, having a rigid bent elbow pointing generally up and rearward of the apparatus 10 and the stub pins 62 being as though rigidly gripped by a fist offset forward from the rigid elbow.

To receive the stub pins 62 of the arms 61, the rear bottom portion of the floor 43 of the base 31 is provided with substantially T-shaped through slots 64 (FIG. 9) laterally spaced from each other in correspondence to the lateral spacing of the arms 61 along the top edge 63 of the paddle 60. Each T-shaped slot 64 has a leg 65 extending forward and a cross-head 66 thereof extending laterally at the rear end of the leg. Each T-shaped slot is spaced below the floor 43 in the bottom of a rectangular box 67 fixedly and preferably integrally depending from the floor 43. The boxes 67 have open tops 68 which open upward through the floor 43 of the base 31. The floor is thus open above the box 67 except for small square portions 70 of the floor 43 above the ends of the cross-head 66 of the T-shaped slot 64. The longitudinal (forward/rearward) portion of this T-shaped slot 64, through the length of the slot leg 65 and thickness of the cross-head 66, are below the open portion of the floor.

To install the paddle 60 with respect to the base 31, the paddle is placed under the base 31 and as flat against it as possible. The stub pins 62 on the paddle arms 61 are snapped upward into the cross-heads 66 of the T-shaped slots 64 in the bottoms of the boxes 67. With the stub pins 62 of the arms 61 riding upon the bottoms of the boxes 67, and the arms 61 hanging down through the legs 65 of the T-shaped slots 64, the paddle can slide forwardly and rearwardly along the slot legs 65 and the paddle is free to pivot within a limited range, determined by collision of its front end with the ribs 56 on the back of the reservoir 12, on the one hand, and by abutment of the top edge 63 of the paddle 60 against the bottoms of the boxes 67. The latter prevents rearward pivoting of the paddle to a true vertical depending position, such that the paddle normally hangs from the bottoms of the boxes, in a free manner, due to gravity, with about a 70° to 80° forward opening angle between the paddle 60 and the floor 43 of the base 31.

To support the blood collection apparatus 11 on a bed rail R, the bottom on the base 31 is rested on the bed rail (FIG. 5) with the ribs 56 of the reservoir 12 abutting the front face of the rail. The paddle 60 is then slid forwardly along the legs of the T-shaped slots 64, by manually pressing the top edge 63 of the paddle forwardly to bring the bottom portion of the paddle against the back face of the bed rail R. Continued forward sliding of the top edge of the paddle 60 toward the bed rail R under force of the user's thumb will bend the paddle and cock it counterclockwise as seen in FIG. 5, so that the top edge of the paddle 60 bears forcibly against the bottoms of the boxes 67. This creates a resilient jam fit in which the bottoms of the boxes flanking the slots are tightly frictionally gripped between the stub pins and the top edge of the paddle, thereby fixing the forward/rearward position of the paddle 60 with respect to the base 31 and thereby tightly fixedly securing the apparatus 11 on the bed rail R.

To remove the apparatus 11 from the bed rail R, the user merely inserts a finger between each end of the paddle and the bed rail and slides the adjacent top edge corner of the paddle rearward. This can be done simultaneously for both top corners of the paddle, or sequentially.

In the preferred embodiment shown, the lower left (looking forward) corner of the paddle 60 has a preferably integral, slightly stretchy strand 73 (FIG. 5) extending therefrom which can easily be bent around the bottom of a bed rail R and led up past the forward face of the bed rail into a notch 74 which opens at the top and bottom and side thereof from a boss 75. The boss 75 is preferably integral with and protrudes sideways from an intermediate portion of the perimeter flange 40 at the corresponding side of the base 31. The strand 73 is of the same slightly resilient material as the paddle 60. Fixed in spaced relation along the strand 73 are a series of enlarged diameter balls 76, one of which will ride on the top of the boss 75 when the strand is pulled snugly forward and upward around the bed rail R, so as to entrap the bed rail R in completely surrounded fashion by the overlying base 31, the paddle 60 and the strand 73. The strand is shown in use in FIG. 5 and idle in FIG. 3. The strand is easily removed from the rail R simply by pulling sideways from the notch 74 in the boss 75, thereby allowing it to fall to its FIG. 3 idle position.

An outlet tube 80 extends substantially coaxially through the bottom wall 81 of the reservoir 12 (FIG. 8) to define top and bottom nipples 82 and 83 protruding above and below such reservoir bottom wall. A smaller diameter tube 84 similarly sealingly protrudes through the reservoir bottom wall 81, in spaced relation to the rear of the tube 80 and has top and bottom nipples 85 and 86 extending above and below the reservoir bottom wall 81. In the embodiment shown, the top eccentric nipple 85 extends upward to about one-third the height of the reservoir 12 and serves as liquid inlet. The depending central outlet nipple 83 and the eccentric inlet nipple 86 are slightly tapered and are sized to snugly frictionally, but fixedly and removably, receive thereover the adjacent ends of the outlet tube 21 and inlet tube 14 (FIG. 1), respectively, in a sealed manner.

A tall, relatively slim, substantially cylindrical cage 90 (FIG. 8) surrounds the upper inlet nipple 85 and rises from sealed connection to the bottom of the reservoir 12 upward nearly to the underside of the base 31 and hence nearly to the top of the reservoir 12. The cage is solidly closed at its ends and entirely covered around its perimeter with fine mesh screen (not shown) of mesh size about 200 micron or 0.0079 inch, to trap within the cage 90 all solids and semi-solids that may be entrained in the blood draining from the wound W (FIG. 1). The cage 90 is shown in cross section in FIG. 8. Blood can only exit from the cage 90 through the fine mesh screen thereof, in order to enter the interior of the reservoir 12, so that solids from the wound W are thus excluded from the portion of the interior of the reservoir 12 outside the cage 90.

The reservoir 12 is preferably molded of a transparent (clear or tinted) plastics material of rigid type, such as polycarbonate. In this way, the flow and level of liquid in the reservoir can be observed by an attending nurse, or the like, by simple visual inspection from the outside.

Turning now to the suction control assembly 30, the base 31 and cover 32 are advantageously of a substantially rigid molded plastics material, here opaque, such as ABS or polycarbonate.

The base 31 supports atop its floor 43 (FIG. 10) a vacuum pumping unit 100 comprising a DC-powered variable speed motor 101 with a rotating output shaft 102 and a pump 103 driven thereby to establish a partial vacuum in a reservoir 12 fixed beneath the base 31.

The motor has a cylindrical casing and is precisely located on the base 31 by resting on its side in a shallow, snug fitting recess 105 (FIG. 9) opening upward in the floor of the base 31. Springy claws 106 preferably integrally upstanding on opposite sides of the recess 105 partly overlie the motor 101 and fix the motor in the recess in a releasable snap fit manner, allowing the motor to be installed on the base 31 by simply firmly pushing it down into the recess and allowing its removal by any reversal of that movement. Rigid abutments 107 preferably integrally upstanding fixedly from the floor 43 of the base 31 at opposite ends of the recess bear on the ends of the motor. The motor is thus rigidly fixed in place on the base 31 by the recess 105, claws 106 and upstanding abutments 107. A drive member 110 is fixed on the shaft 102 for rotation therewith and includes an eccentric drive pin 111.

The pump 103 is fixedly mounted atop the floor 43 of the base 31. The pump 103 comprises a generally hat-shaped flexible member 113 of suitable elastomeric, generally rubber-like material having a radially outwardly extending brim 114 and a central crown 115. A bracket 116 fixedly and preferably integrally upstanding from the floor 43 of the base 31 receives the crown 115 loosely reciprocably therethrough. The pump includes a rigid cup 117 open toward the open end of the crown 115. The brim 114 is axially fixedly clamped between the bracket 116 and the open end of the cup 117 and folds over the outside of the latter. To this end, resilient hooks 120 fixed on opposite sides of the cup 117 have free ends snap-fitted over the sides of the bracket 116, thereby relatively fixing the cup 117 and hat-shaped member 113. The cup 117 includes an end wall 121 substantially coaxial with the hat-shaped member 113 and closing the space within the hat-shaped member. The end wall 121 includes an inlet port 122 and an outlet port 123. An outlet check valve 124, here conveniently a conventional duck-bill valve, is fixed conventionally on and extends outwardly from the end wall 121 and communicates with the outlet port 123. A tubular valve assembly 125 connects to the inlet port 122 through a tube 127 and includes an inlet check valve 126, again conveniently in the form of a duck-bill valve. The outlet and inlet check valves 124 and 126 respectively permit airflow out of and into the expansible pump chamber 128 enclosed by the cup 117 and the hat-shaped member 113.

An axial drive rod 132 is fixed at one end 133 coaxially to the crown of the hat-shaped pump member 113 and extends away therefrom. The free-end 134 of the drive rod is pivoted on the eccentric drive pin 111 of the motor, the axes of the hat-shaped member 113 and drive rod 132 lying at right angles to the longitudinal axis of the shaft of the motor. The pump 103 and motor 101 are located in the rounded front end portion of the base 31, the motor shaft 102 and pump rod 132 converging forwardly toward the central portion of the rounded part of the rim of the base 31.

Thus, rotation of the motor shaft 102, and hence of the eccentric pin 111 thereon, reciprocates the pump drive rod 132 to reciprocally move the hat-shaped member crown 115 coaxially toward and away from the cup 117 interior to thereby repetitively change the volume of the pumping chamber 128 and thereby alternately push air out the outlet duck-bill valve 124 and suck air into the inlet duck-bill valve 126.

Figure 13:
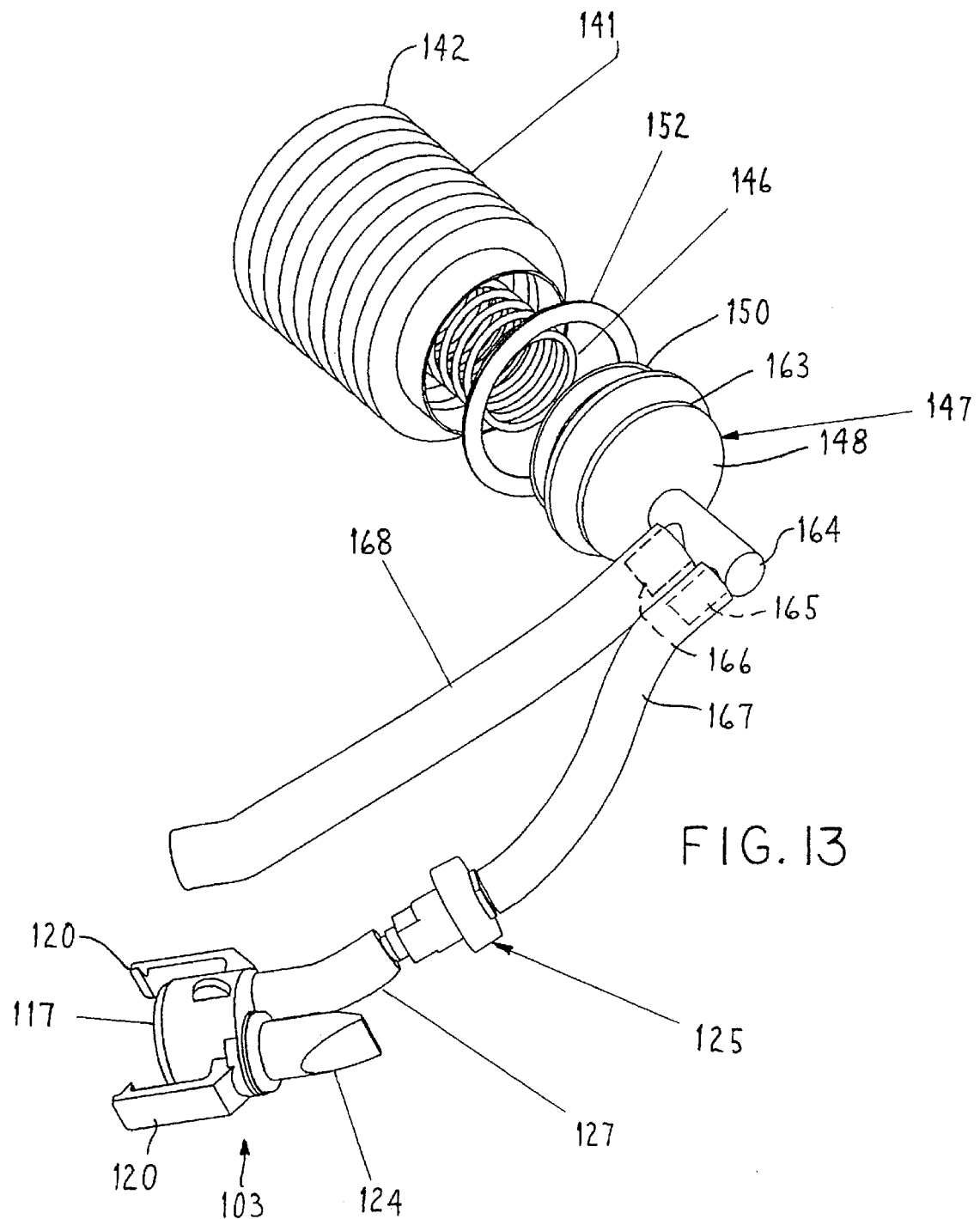
FIG. 13 is an enlarged exploded pictorial view of the bellows and vacuum pump of FIG. 10.
Figure 14:
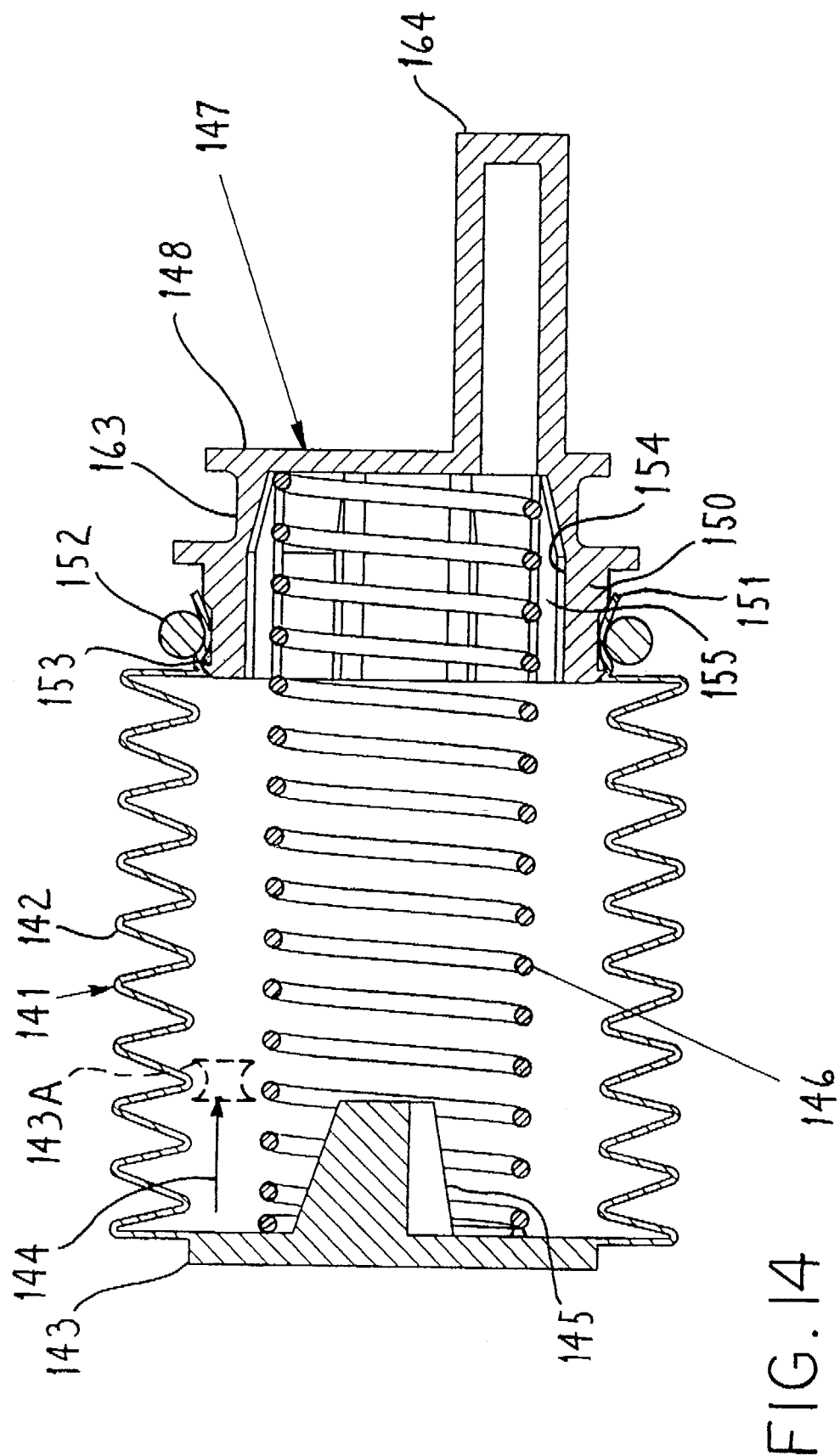
FIG. 14 is an enlarged central cross-sectional view of the FIG. 13 bellows.

A vacuum sensing unit comprises a bellows assembly 141 (FIGS. 10, 13 and 14) including an axially expandable and compressible bellows 142 (FIG. 14) having a closed end wall 143 axially moveable, in accord with the arrow 144 from its extended, rest position shown to a partly compressed position 143A, as with a partial vacuum therein. The end wall 143 is substantially rigid and carries a coaxial, interiorly extending projection 145 for coaxially locating the leftward (FIG. 14) end of a bellows expanding, helical, compression spring 146.

The bellows assembly 141 further includes an end support 147 (FIGS. 13 and 14) which serves several functions, as follows. The end support 147 closes the rightward (FIG. 14) end of the bellows 142. To this end, the support 147 includes a plug portion 150 around which is snugly sleeved a rightward extending coaxial annular end flange 151 which defines the right end of the bellows 142. An annularly stretched, resilient ring 152, here a conventional O-ring, sealingly presses the bellows end flange 151 into an annular groove 153 in the perimeter of the plug portion 150, to fixedly and sealingly secure the open right end of the bellows 142 coaxially on the end support 147, such that the bellows 142 is carried in laterally cantilevered fashion on the end support 147.

The end support 147 has a leftwardly (FIG. 14) opening coaxial recess 154 which coaxially seats and takes the rightward thrust of the spring 146. In one unit constructed in accord with the invention, circumferentially spaced, axial ribs 155 extend radially into an axially long interior of the recess 154 for bearing on and centering the spring 146 coaxially there within.

Figure 10B:
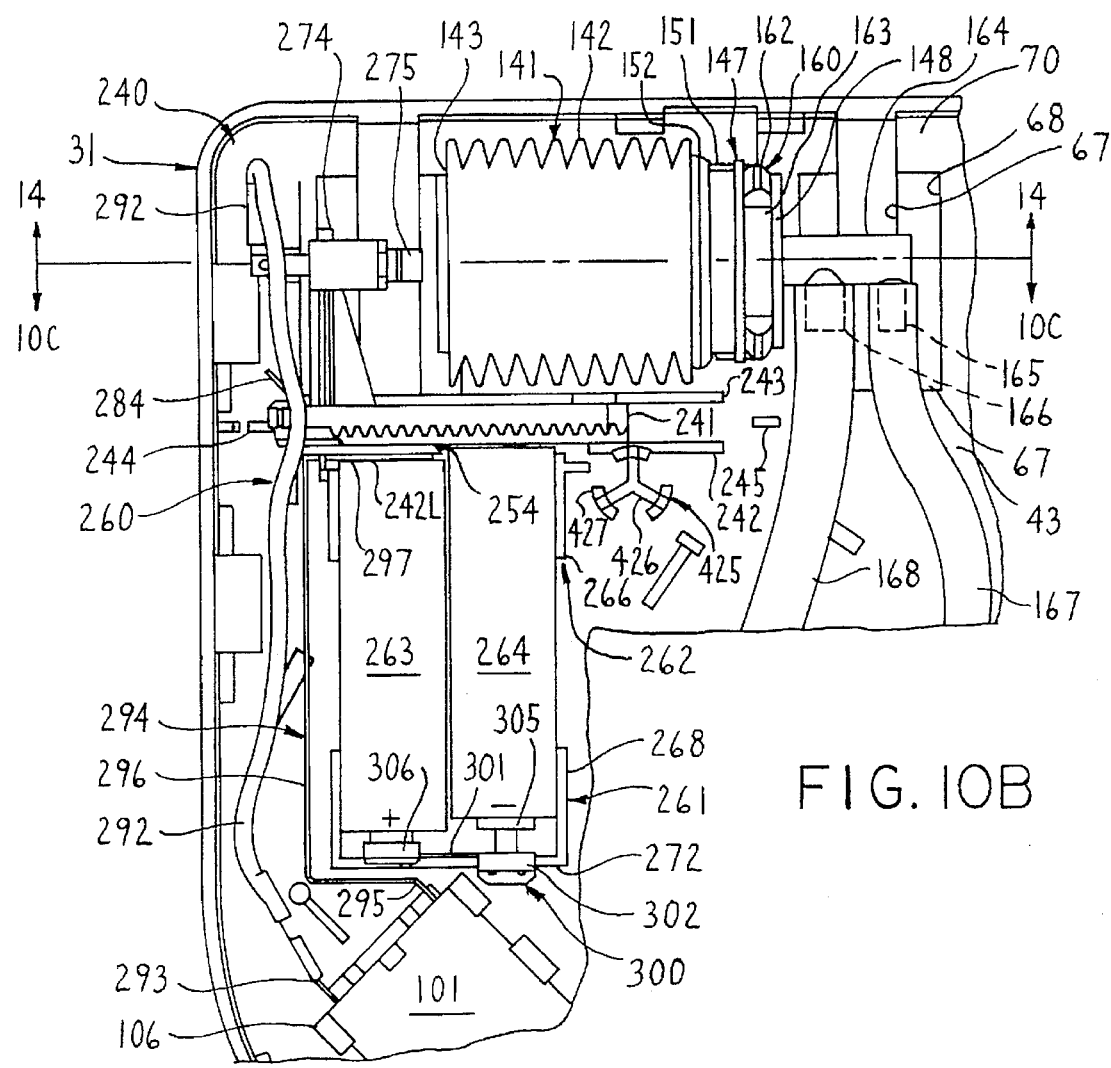
FIG. 10B is an enlarged fragment of FIG. 10 showing the bellows and the electrical circuitry.
Figure 11:
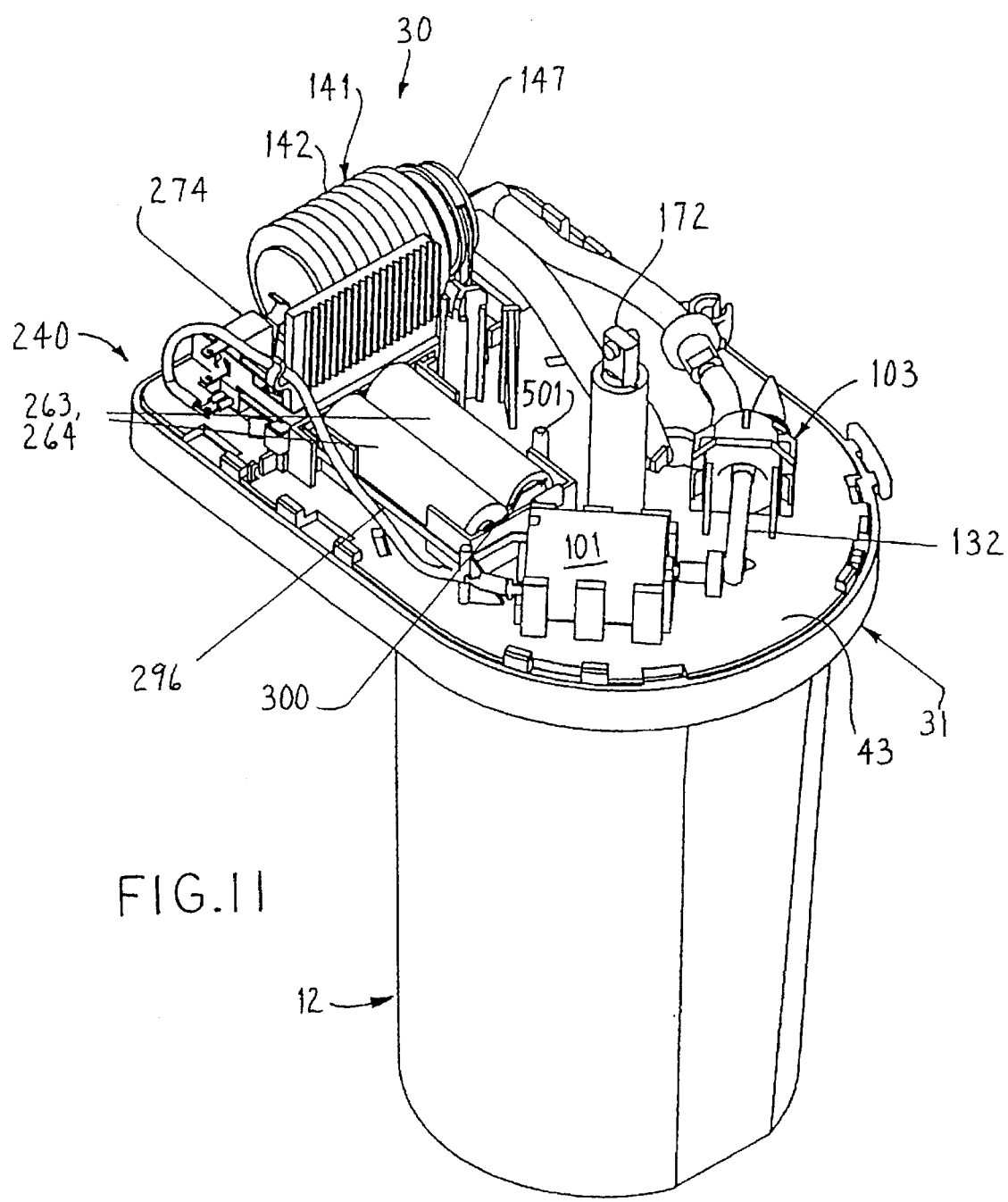
FIG. 11 is a pictorial view taken from the front and left side of FIG. 10.
Figure 12:
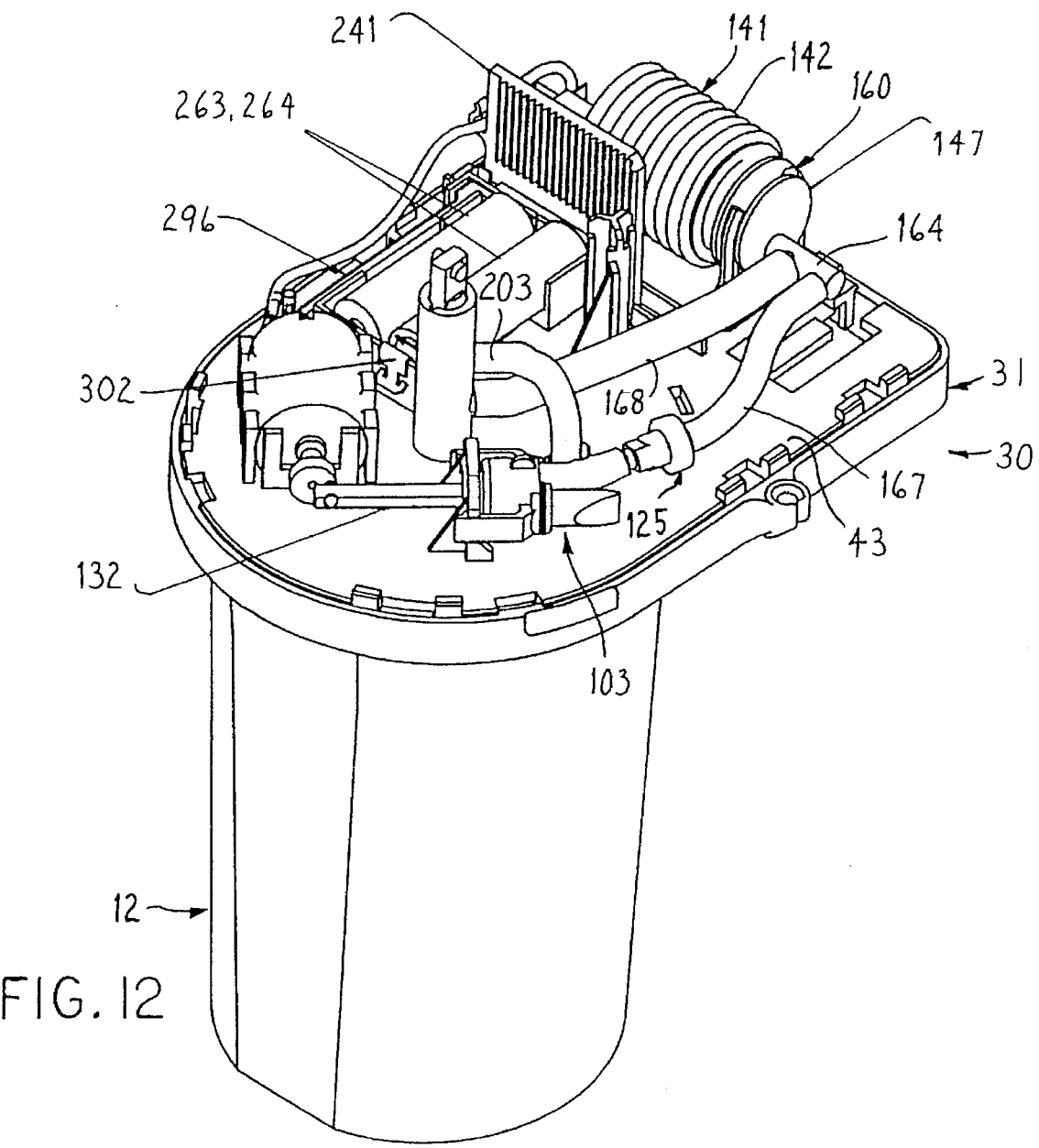
FIG. 12 is a pictorial view taken from the front and right side of FIG. 10.

The bellows assembly 141 is located along the floor 43 (FIGS. 10–12) near the rear edge thereof and transversely between the open tops 68 (FIG. 10) of the boxes 67. The length axis of the bellows assembly 141 extends parallel to the rear edge of the floor 43. To this end, the bellows end support (fixed end) 147 is fixedly but releasably supported, in spaced relation above the floor 43, by a carrier 160 (FIG. 8) comprising a tongue 161 and a flanking pair of jaws 162 fixedly upstanding from and preferably integral with the floor 43 between the open upper box ends 68 and adjacent to the one thereof behind the pump 103. An annular groove 163 (FIG. 14) in the end support 147 of the bellows assembly receives the upper end of the tongue 161 (FIG. 8) and, in snap fit relation, the upper ends of the jaws 162, which hook inward toward each other to resiliently grip and hold down the bellows assembly fixed end 147 atop the tongue 161, as seen for example in FIGS. 10–12. Thus, the carrier 160 grips the bellows assembly free end 147 at three circumferentially, generally evenly spaced locations so as to cantilever the bellows 142 leftwardly (FIGS. 10–12 and 10B) therefrom in spaced relation above the floor 43, so that the bellows 142 is free to axially expand away from and contract back toward the fixed end 147 thereof. In this way, the bellows closed end wall 143 is moveable laterally toward the carrier 160 in the direction of the arrows 144 in FIG. 14. The jaws 162 allow both snap fit insertion and removal of the bellows assembly with respect to the carrier 160.

Figure 10C:
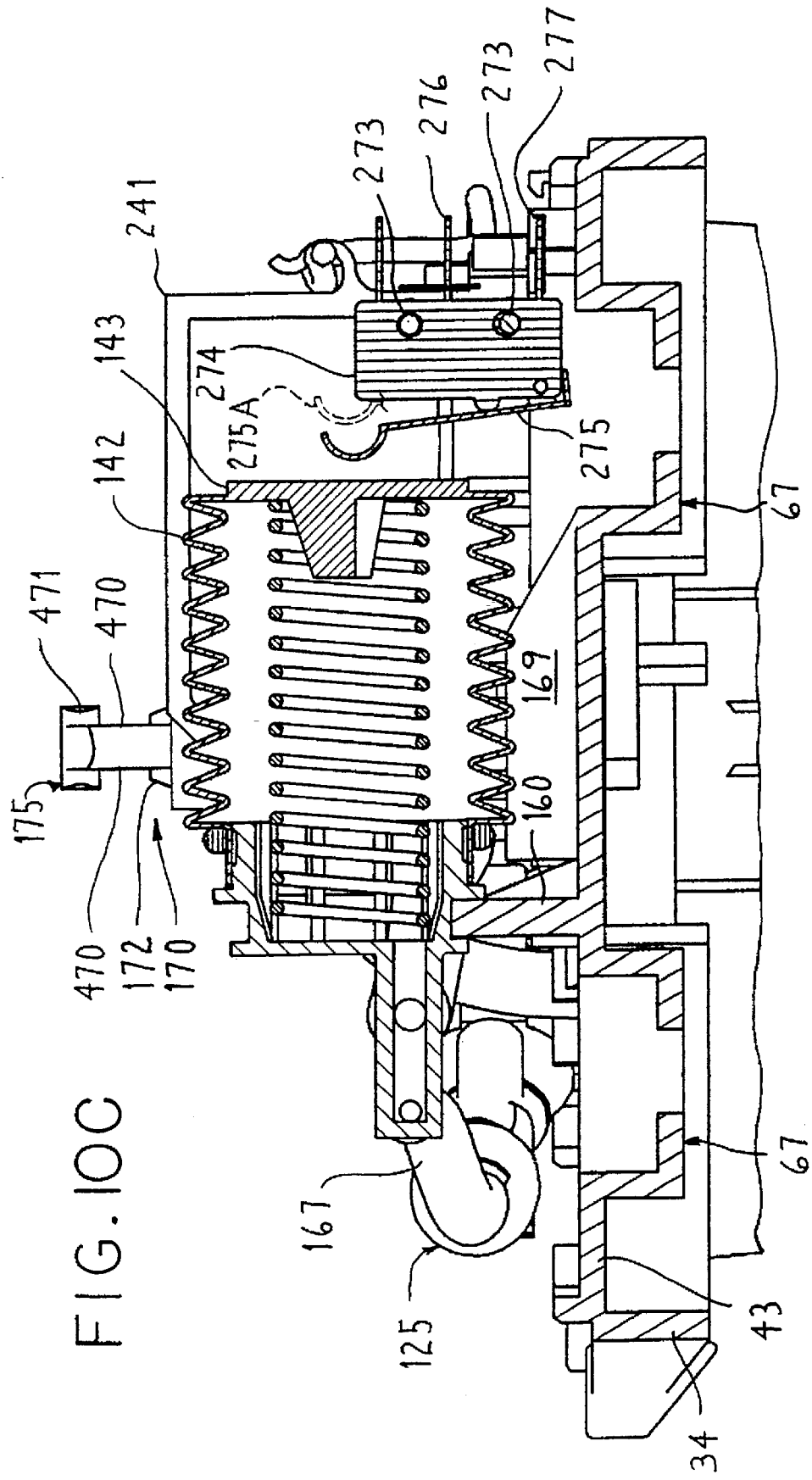
FIG. 10C is a sectional view substantially taken on the line 10C—10C of FIG. 10B and showing the bellows and switch from the rear.

Spaced, parallel front and rear ridges, one being shown at 169 in FIG. 10C, extend laterally outboard away from the carrier 160 (i.e. to the right in FIG. 10C) in the direction of bellows expansion and contraction. The ridges 169 cradle the bellows 142 and help guide its expansion and contraction direction.

A manifold 164 preferably integrally protrudes axially beyond the closed end wall 148 of the bellows fixed end 147 (FIGS. 10B, 13 and 14) at an off-center location thereon. The manifold 164 is hollow and communicates with the interior of the recess 154 and bellows 142, on the one hand, and, on the other hand, has radially outwardly extending hollow tubular nipples 165 and 166. The suction pump 103, and more particularly the tubular assembly 125, communicates through a tube 67 (FIG. 13), sealingly sleeved thereon and on nipple 165, and thence through the manifold 164 with the interior of the bellows 142.

A valve assembly 170 (FIGS. 3, 7, 8 and 15) connects to the other nipple 166 through a tube 168. The valve assembly 170 comprises a tubular valve sleeve 171 preferably integral with and perpendicular to and extending through the floor 43 so as to have upper and lower portions extending above and below such floor. The valve sleeve 171 is here preferably located substantially at the center of the rounded front portion of the floor 43 and extends, with its lower part, down into the reservoir 12. The valve assembly 170 further includes a valve plunger assembly comprising a valve plunger 172 (FIGS. 16 and 17) and a coil spring 173 coaxially sleeved over the intermediate portion of the valve plunger 172 and blocked against downward movement further along the valve plunger by a radial flange 174 fixed on and preferably integral with the valve plunger.

Figure 15:
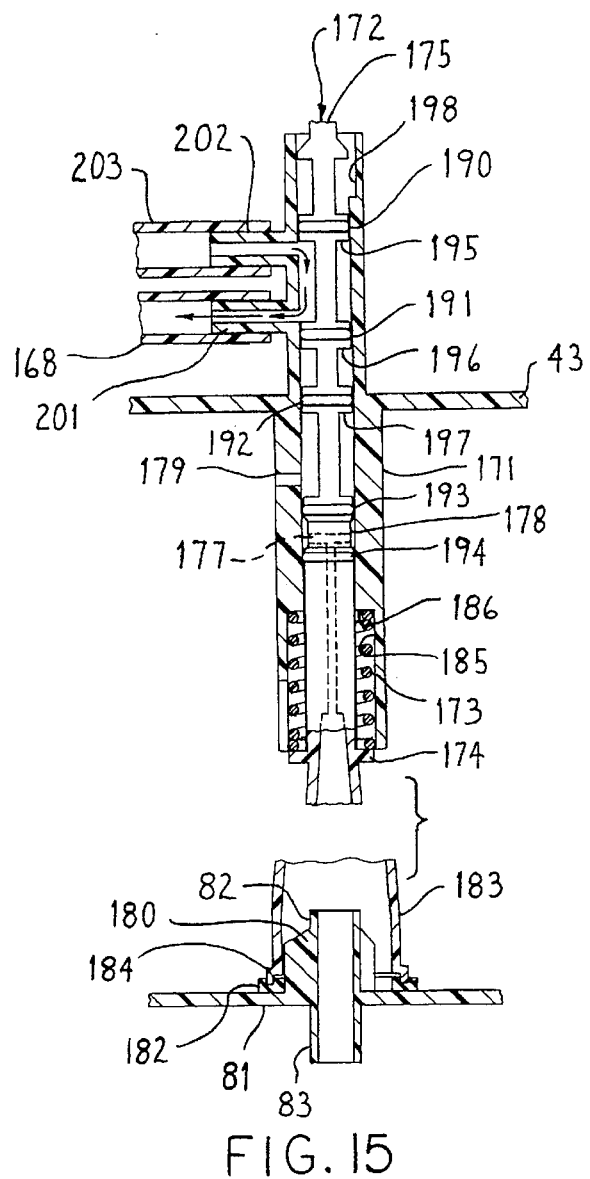
FIG. 15 is an enlarged central cross-sectional view of the valve assembly, substantially is taken on the line 15—15 of FIG. 10.
Figure 15A:
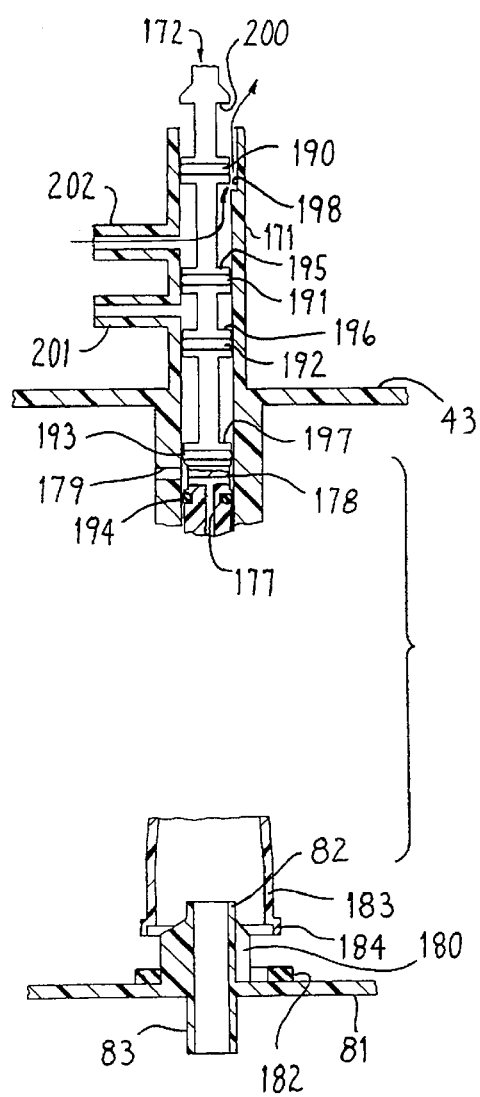
FIG. 15A is a view similar to FIG. 15 with the valve plunger raised to its open position for emptying the reservoir of blood.

As seen in FIGS. 8 and 15, the upper portion of the valve plunger 172 is slidably guided in the valve sleeve 171 and has a preferably integral upper end fitting 175 protruding from the top of the valve sleeve 171 with the bottom end 176 of the valve sleeve 171 resting on the bottom 81 of the reservoir 12 (with the reservoir fixed pendently beneath the base 31 as shown in FIG. 8). The top nipple 82 of the outlet tube 80 is flanked by three evenly circumferentially spaced webs 180 (FIGS. 15 and 15A) preferably integral therewith and with the reservoir bottom wall 81. A resilient seal washer 182 atop the reservoir bottom wall 81 (FIG. 15A) is located by the webs 180 to coaxially surround the top nipple 82. The lower portion 183 (FIGS. 8 and 16) of the valve plunger 172 is hollow and slightly outwardly and downwardly flared in a steep frustoconical shape. The webs 180 fit snugly but slidably within, and help center, the lower portion 183 of the valve plunger coaxially around the top nipple 82, in the lower position of the valve plunger 172 shown in FIGS. 8 and 15. The lower portion 183 of the valve plunger 172 terminates at its lower end in a radially outwardly stepped, down facing, annular flange 184 (FIGS. 15, 15A and 16). The annular flange 184 is adapted by seat sealingly upon the seal washer 182 in its downward position shown in FIGS. 8 and 15. In this position, the valve plunger lower portion 183 serves to close off the top nipple 82 from the interior of the reservoir 12. Thus, the top nipple 82 cannot be used to drain, or maintain atmospheric pressure in, the reservoir 12 with the valve plunger 172 in its closed bottom position shown in FIGS. 8 and 15.

The coil spring 173 of the valve assembly 170 is received in and bears against the top of a recess 185 (FIG. 15) opening downward into the interior of the reservoir 12 from the bottom of the valve sleeve 171. Thus, the coil spring 173 is axially trapped between a down facing step 186 at the top of the recess 185 and the radial flange 174 fixed on the valve plunger 172, in such way as to resiliently urge the valve plunger 172 downward forcibly against the seal washer 182, to sealingly isolate the top nipple 82 from the interior of the reservoir 12 around the valve plunger 172 as above mentioned.

The valve plunger 172 can be forced upward, compressing the spring 173, to its FIG. 15A raised position, spaced above the seal washer 182. This allows blood in the reservoir 12 to drain down through the top and bottom nipples 82 and 83. The fully raised valve plunger bottom flange 184 is still below the top of the top nipple 82, which acts as a standpipe, to block a fatty material (e.g. lipids) layer floating atop the blood, from escaping from the reservoir with the downward draining blood.

The upper portion of the valve plunger 172 (FIG. 15) is snugly vertically slidable in the valve sleeve 171 above the recess 185 and comprises a plurality of axially spaced annular grooves filled by conventional O-rings 190, 191, 192, 193 and 194. The upper portion of the valve plunger 172 has radially outwardly opening venting recesses 195, 196 and 197 disposed between the O-rings 190, 191, 192 and 193, in that order. The upper portion of the valve plunger 172 has a further venting recess 200 opening out radially therefrom and closed axially between the upper end fitting 175 and upper O-ring 190. As seen in FIG. 16, each recess 195, 196, 197 and 200 is matched by corresponding recesses distributed circumferentially around the valve plunger 172, so precise rotative positioning of the plunger 172 in the valve sleeve is not needed.

An antisiphoning passage 177 (FIGS. 15 and 15A) communicates from the open bottom of the valve plunger 172 coaxially upward in the valve plunger and angles out radially into the annular clearance space 178 axially between the lower O-rings 193 and 194 and radially between the valve plunger 172 and surrounding valve sleeve 171. The annular space 178 is closed with the valve plunger down as in FIG. 15. However, such passage 177 opens to the upper part of the interior of the receiver 12, through a radial hole 179 in the valve sleeve 171, just below the floor 43, with the valve plunger up as in FIG. 15A.

Closely vertically spaced nipples 201 and 202 (FIG. 15) extend radially outward from the upper portion of the valve sleeve 171 above the floor 43 in vertically close spaced relation. Both nipples 201 and 202 communicate with the interior of the valve sleeve 171. The lower nipple 201 connects through the tube 168, above mentioned, to the bellows assembly 141 and thence through the tube 167 to the vacuum pumping unit 100 above described. The upper nipple 202 connects through a tube 203 (FIGS. 9 and 12) extending through a hole 204 (FIG. 9) in the floor 43 to an air filter assembly 205 sealingly and pendently fixed to the bottom of the floor 43 as generally indicated in FIGS. 6–9, for withdrawing of air, but not liquids, from the reservoir 12 in response to operation of the pump 103 with the valve plunger 171 down (FIG. 15), so that its venting recess 195 connects the nipples 201 and 202.

On the other hand, with the valve plunger 171 up (FIG. 15A), its venting recess 195 vents the top of the reservoir 12 through an axial vent groove 198 (or a corresponding radial through hole not shown) in the inner wall of the valve sleeve 171 upper end to the atmosphere; the O-rings 191 and 192 close the nipple 201 connected to the vacuum pump 103 and bellows 142 (to soon stop and hold stopped the vacuum pump 103); the passage 177 applies the atmospheric pressure in the top portion of the reservoir to the top of the standpipe 82; and, of course the seal 182 and flange 184 are spaced to allow blood flow from the reservoir 12 out the standpipe 82. Note that the thus-open passage 177 prevents creation of subatmospheric pressure atop the open standpipe 82 due to blood flow down through the tube 21 to the blood bag 20 and so prevents suctioning (siphoning) of flowable contaminants (e.g. lipids), in a layer floating atop the blood, from the reservoir into the standpipe.

The air filter assembly 205 may be conventional, for example, the kind disclosed in U.S. Pat. No. 5,156,602 (Steffler), assigned to the Assignee of the present invention. However, in the embodiment shown, the air filter assembly 205 preferably is improved to provide even more isolation between liquid in the reservoir 12 (particularly fatty materials therein) and the hydrophobic filter element therein, so as to reduce even further the risk of contamination by fatty materials of such hydrophobic filter element, while still allowing pumping and venting of air from the reservoir 12 therethrough.

Figure 27:
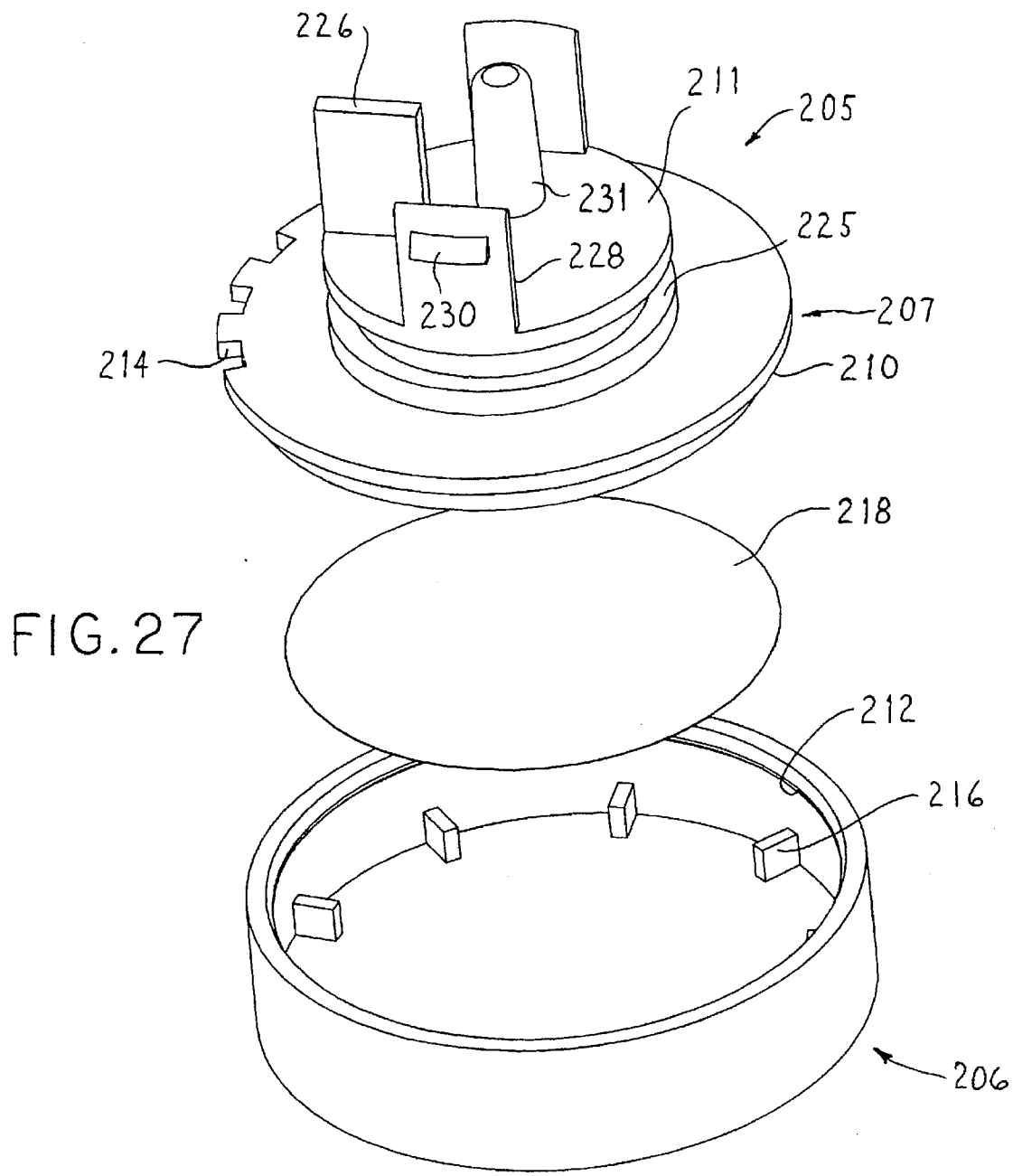
FIG. 27 is an enlarged, exploded pictorial view of the air filter of FIG. 7.
Figure 28:
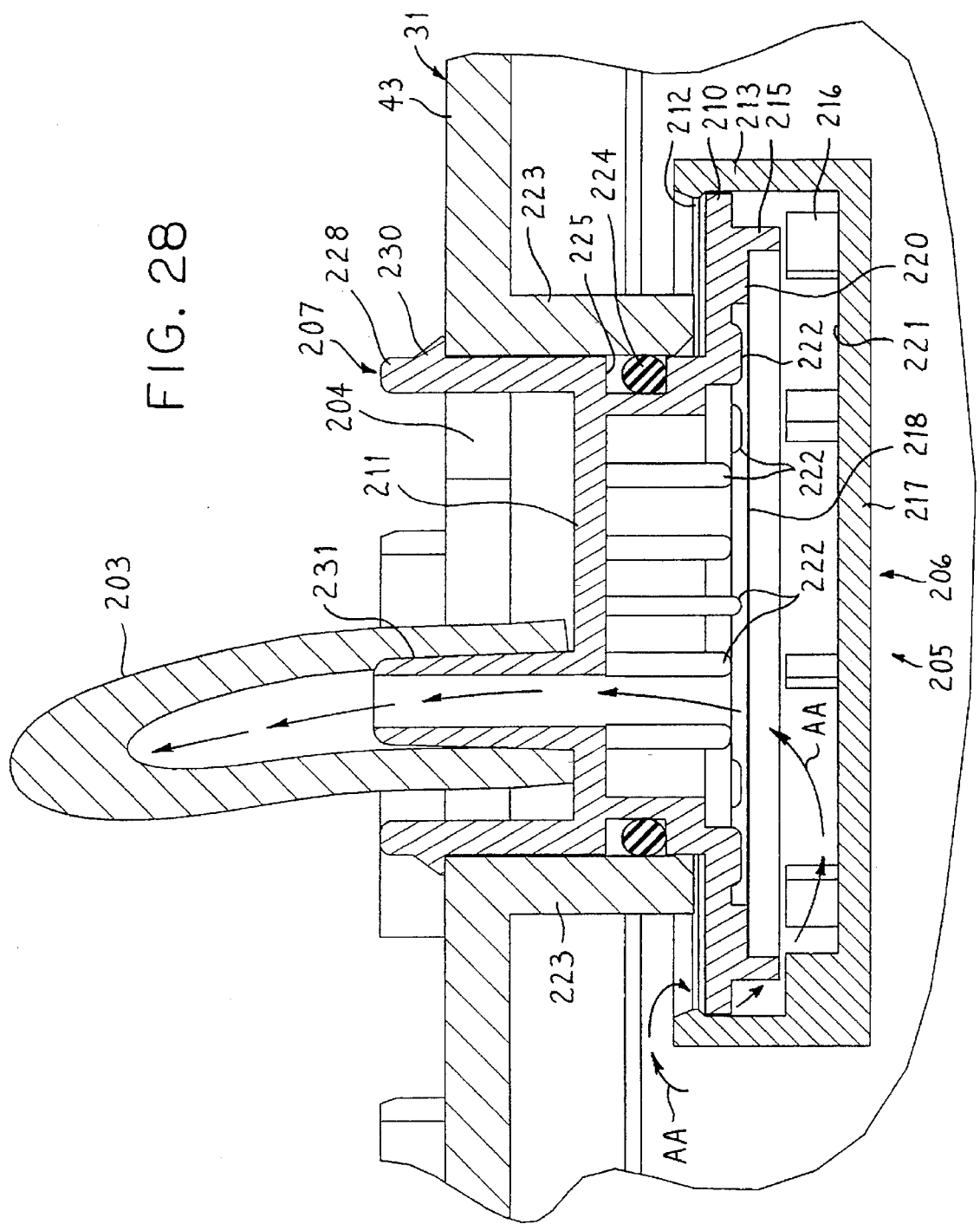
FIG. 28 is an enlarged central cross-sectional view substantially as taken on the line 28—28 of FIG. 9 and showing the FIG. 27 air filter.
Figure 30:
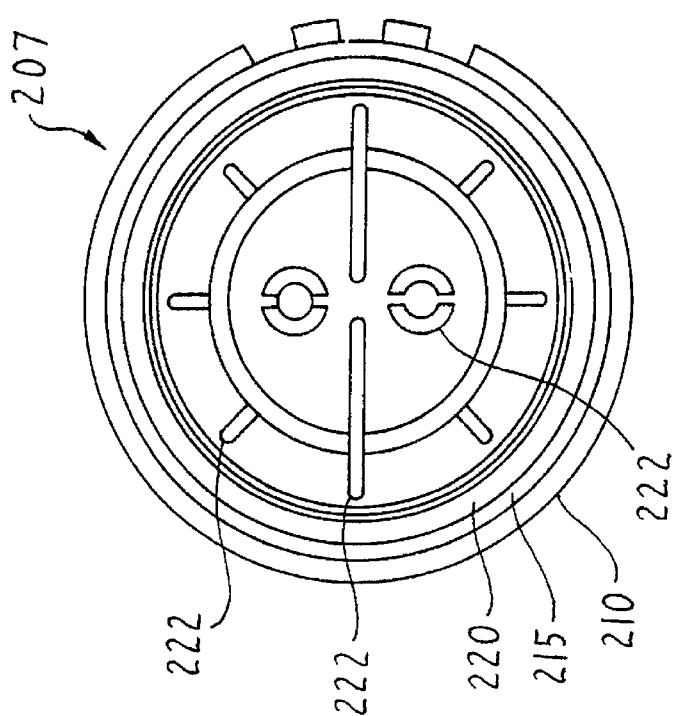
FIG. 30 is a bottom view of the FIG. 27 air filter top lid.
Figure 29:
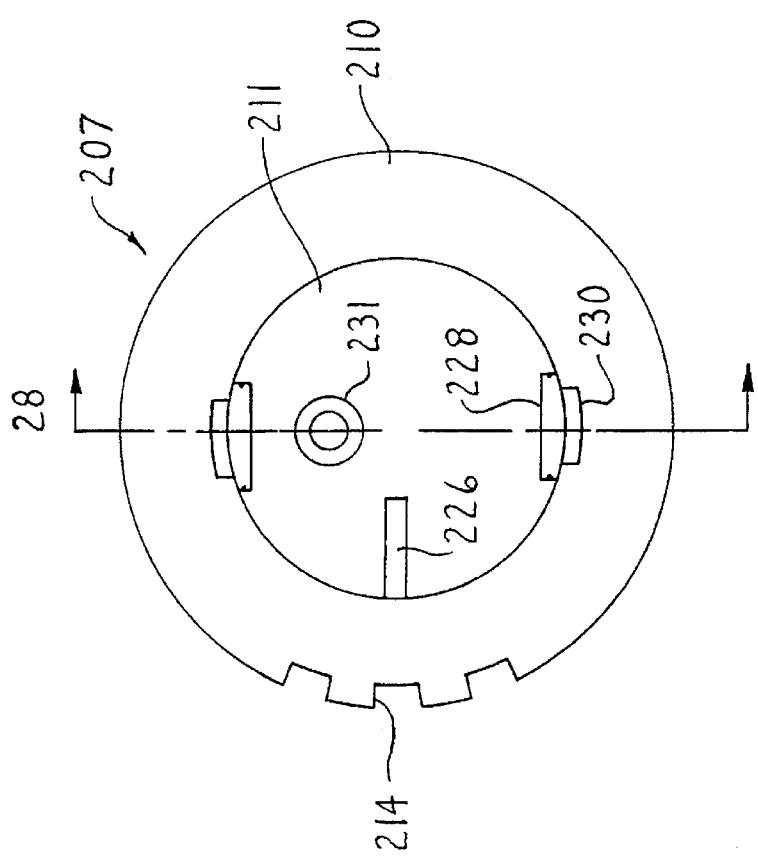
FIG. 29 is a top view of the FIG. 27 air filter.

Thus, a preferred filter assembly 205 (FIGS. 28–30) comprises a broad, shallow, upward opening cup 206 closed at its upper end by, and independently supported by, a generally hat-shaped lid 207, in turn fixedly depending from the floor 43. The lid 207 has a flat rim 210 centrally surmounted by an inverted cup-shaped crown 211. The lid brim 210 snap fits down into the top of the cup 206, being resiliently retained therein by an annular bead 212 radially inwardly protruding (FIG. 28) in fixed relation on the interior surface of the side wall 213 of the cup 206. The lid can thus dependently support the cup 206 therebelow as seen in FIG. 28. Small notches 214 (here three in number) are circumferentially close spaced in the outer peripheral edge of the brim 210 as seen in FIG. 27. These notches 214 extend radially inward sufficient to allow air flow from the upper portion of the reservoir 12 downward through the notches 214, past the annular bead 212 and into the interior of the cup 206 below the lid 207. Indeed, the fit of the brim 210 of the lid 207 radially in the cup 206 is relatively loose so that air would be free to flow through the clearance therebetween even in the absence of the notches 214, as generally indicated by the arrows AA in FIG. 28.

In the unlikely event that liquid from the reservoir 12 may in small quantity enter the cup 206 with incoming air from the reservoir, along the path defined by the arrows AA, such liquid is discouraged from splashing upward toward the crown 211 as follows. First, a rigid annular skirt 215 coaxially depends from the brim 210 in close spaced relation from the periphery of the brim. The skirt 215 depends only a relatively short distance into the cup 206 and below the brim 210 and acts to deflect any inward flow downward and away from the underside of the brim 210. In addition, circumferentially spaced baffles 216 extend inward from the side wall 213 of the cup 206 and extend upward from the bottom wall 217 of the cup. The baffles 216 rise almost to the underside of the skirt 215 and extend radially inward to about the same extent as the skirt 215, so as to tend to limit circumferential sloshing of any liquid that may enter the cup 206.

A commercially available, disk-like, microporous hydrophobic filter sheet 218 has a perimeter portion fixed to the underside of an annular step 220 extending radially inward from the skirt 215 on the underside of the lid 207. The filter sheet 218 is preferably fixed to the underside of the step 220 by ultrasonic welding, though other convenient means may be used. The filter sheet 218 may be like the screen described at 273 in aforementioned U.S. Pat. 4,655,754. Such screen is hydrophobic in the sense of allowing free passage of gases therethrough but blocking passage of liquid therethrough. However, it is preferred that an improved version of the hydrophobic filter sheet be used. A hydrophobic filter sheet is now available in a new laminate which has an anti-lipids (oleophobic) face which makes the underside of the filter sheet 218 less attractive to fats. Such new hydrophobic filter sheet 218 is cut to size from a laminate sheet of Goretex® PTFE (polytetrafluoroethylene) membrane with an applied ZINTEX® oleophobic laminate thereon, marketed by W. L. Gore and Associates Inc. located at Elkton, Md.

Thus, should the apparatus, by careless handling, be tipped and agitated sufficient to allow blood mixed with lipids to enter along the path of the arrows AA into the chamber 221, defined between the cup bottom 217 and the hydrophobic filter sheet 218, and have lipids and blood splash up against the bottom of the filter sheet 218, the fact that the filter sheet 218 is well spaced above the bottom wall 217 of chamber 221 and that the hydrophobic filter sheet inlet side faces downward enables gravity to assist the oleophobic and hydrophobic character of the filter sheet to cause lipids to drop off the filter sheet onto the bottom wall 221 of the cup 206. Further, the air filter assembly 205 (FIG. 28) is located as high in the reservoir 12 as possible, namely in close spaced relation beneath and parallel to the floor 43 of the overlying base 31, so as to be as far as possible out of contact with liquid in the reservoir 12.

The net result of this combination of features is to make it unlikely that even careless handling of the apparatus would blind the filter sheet 218 with liquids, e.g. blood or lipids, from the reservoir 12, providing a high probability that the air filter assembly 205 will permit maintaining of a subatmospheric pressure in the reservoir 12 for the desired life of the apparatus.

A network of ribs 222 (FIGS. 28 and 30) depends fixedly from the underside of the lid 207 in close proximity with the top of the filter sheet 218 to positively block excessive upward bending in the filter sheet in response to drawing of air therethrough from the reservoir 12 upward into the tube 203 (FIG. 12) as above described.

To install the air filter assembly 205 fixedly and pendently beneath the floor 43 of the base 31, the upstanding crown 211 of the lid 207 is inserted snugly and slidably upward into telescoped relation within an annular flange 223 (FIGS. 7 and 28) depending fixedly from the underside of the floor 43. An air seal annularly between the depending annular flange 223 and the crown 211 is provided by an O-ring 224 (FIG. 28) in an annular groove 225 in the periphery of the crown 211.

A fin 226 fixedly upstanding from the top of the crown 211 is on a radius of the crown and is on the side of the crown toward the air entry notches 214. As seen in FIG. 10, the upstanding fin 226 is upwardly received in a notch 227 in the edge of the hole 204 in the floor 43. The notch 227 is aimed at the valve assembly 170 which thus aims the fin 226 and the air inlet notches 214 at the valve assembly 170 and thus at the upstanding central axis of the reservoir 12. Fixing of the air filter assembly 205 to the underside of the base 31 thus positively requires that the air inlet notches 214 be aimed toward and be close adjacent to the central axis of the reservoir 12 for a minimum risk of entry of liquid into the air filter assembly cup 206 upon accidental tilting of the apparatus 10.

The air filter assembly 205 is preferably positively but releasably fixed to the floor 43, in depending relation therefrom, by a snap fit connection. More particularly, in the embodiment shown, the snap fit connection comprises a diametrally opposed pair of plate-like, springy fingers 228 elastically bendable toward and away from each other and being insertable up through the hole 204 in the floor 43 of the base 31 in close sliding relation with the edges of the hole. Preferably integral, radially outwardly disposed, upward tapering, flat bottom, wedges 230 on the outside faces of the fingers 228 slide upward through the depending annular flange 223 and the top of hole 204 as the air filter assembly 205 is pushed upward into the annular flange 223. Ultimately, the wedges 230 rise up out of the hole 204 and snap rigidly outward over the top of the floor 43, as shown in FIG. 28, to fix the air filter assembly 205 positively to the bottom of the floor 43 of base 31.

A nipple 231 is fixedly and preferably integrally upstanding from the lid 207. The nipple 231 snugly and sealingly receives the air inlet end of the tube 203 which, as above mentioned, leads to the reservoir air intake nipple 202 on the top of the valve assembly 170 (FIG. 15). In this way, air is evacuated from the reservoir 12 through the air filter assembly 205 and thence to the valve assembly 170.

The apparatus further includes a vacuum control unit 240. The vacuum control unit 240 (FIG. 10B) comprises an upstanding, laterally elongate, plate-like slider 241 located just in front of the bellows 142 and slidable transversely of the base 31, namely in a direction parallel to the extension/contraction axis of the bellows 142. A transversely elongate, parallel pair of guide rails 242 and 243 preferably integrally project up from the floor 43 in front of the bellows and guide the slider 241. Longitudinal travel of the slider 241 widthwise of the base 31 is limited by end stops 244 and 245 preferably integrally upstanding from the floor 43, and between which the slider 241 has a range of sliding movement.

Intermediate its ends, the rear rail 243 (FIGS. 10F–H) preferably integrally includes an upstanding hold-down finger 246 and an adjacent upstanding detent finger 247 which oppose a horizontal rib 250 protruding rearward from the rear face of the slider 241, extending substantially the width thereof, and being spaced from the top and bottom thereof. The hold-down finger 246 has a forward extending flange 251 which overlies the slider rib 250 in snug but sliding fashion to positively prevent the slider 241 from jumping up away from the floor 43 and out of guided relation between the front and rear rails 242, 243. The horizontal rib 250 on the back of the slider 241 has notches 253 at spaced points along its length for resilient engagement by an upstanding ridge 252 on the upper front portion of the detent finger 247 so as to positively locate several stopping points for the slider along its horizontal path of travel.

The front rail 242 (FIGS. 10D and 10F) has an open space 254 intermediate its ends, near the upstanding fingers 246 and 247 of the rear rail 243, and sized and located to receive therethrough the end of a battery hereafter described.

A power unit 260 (FIGS. 10–12) comprises front and rear cradles 261 and 262 (FIGS. 9 and 10B) upstanding from the floor 43 in front of the slider rails 242 and 243 and shaped for cradling thereon a battery power pack, here conveniently and inexpensively comprising a pair of conventional AA batteries 263, 264 of the kind widely available in grocery and other retail stores. The cradles 261 and 262 orient the batteries physically parallel with the front/rear direction of the base 31 (the length direction of the base 31). The batteries 263, 264 may thus be referred to as the laterally inboard and outboard batteries 263, 264, same being disposed respectively adjacent the front/rear centerline of the base 31 and near the left side thereof, as seen from the front of the base 31.

The battery cradles (FIG. 9) each have low, scalloped, parallel, transverse, opposed walls 265 and 266 upon which the intermediate portions of the batteries rest. The battery orientation is illustrated by schematic representations 267 of the two batteries preferably molded into the top of the floor 43 between the cradles. The cradles have upstanding side walls 268 (FIG. 10B) which flank the batteries and cooperate with the scallops to prevent sideways movement of the batteries with respect to floor 43. One end (preferably the positive end) of the inboard battery 264 protrudes rearwardly through the gap 254 in the front guide rail 244 to bear on the lower portion of the front face of the slider 241.

Figure 10D:
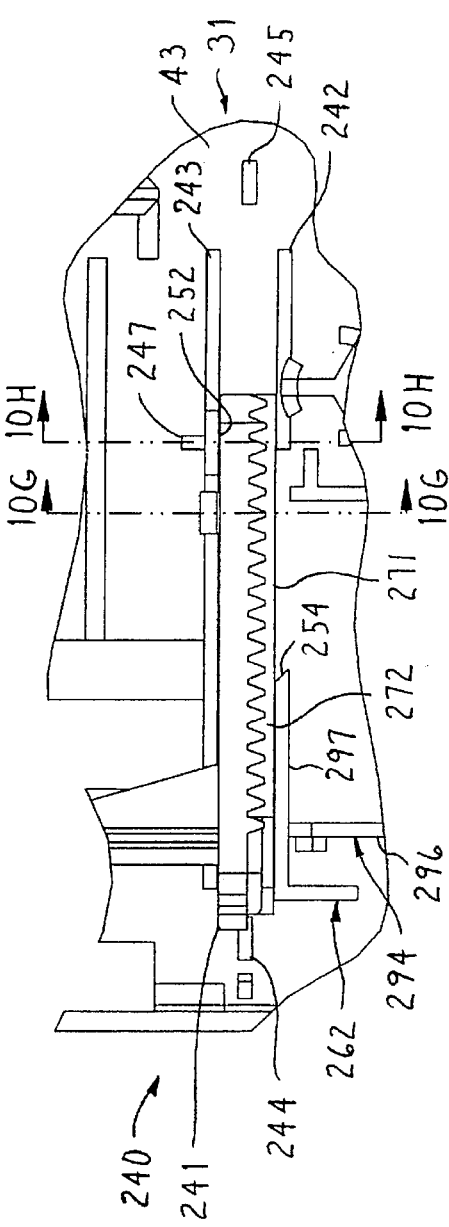
FIG. 10D is an enlarged partially broken top view of the slider of FIG. 10.
Figure 10F:
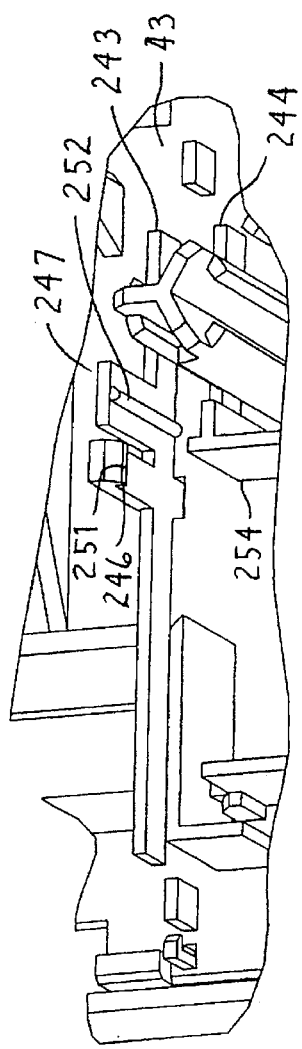
FIG. 10F is an enlarged pictorial view, taken from above and in front, showing the guide rails for the slider of FIG. 10.
Figure 10H:
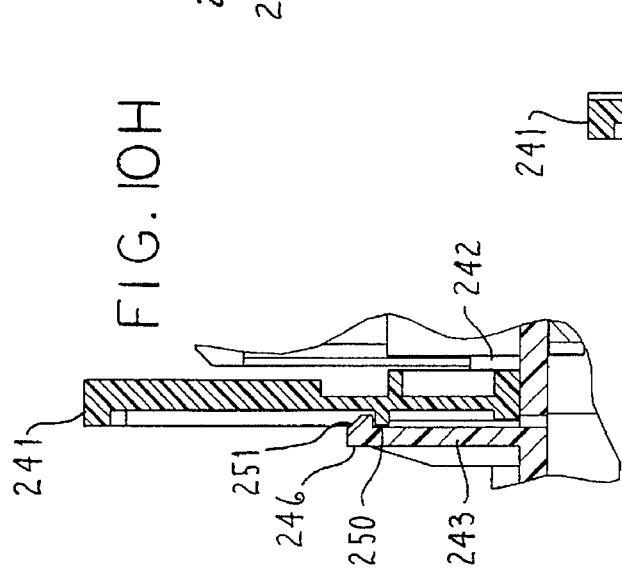
FIG. 10H is an enlarged sectional view substantially taken on line 10H—10H of FIG. 10D.
Figure 10G:
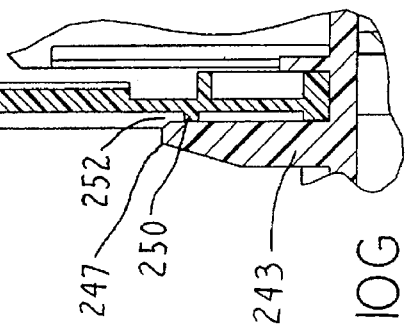
FIG. 10G is an enlarged sectional view substantially taken on line 10G—10G of FIG. 10D.
Figure 10I:
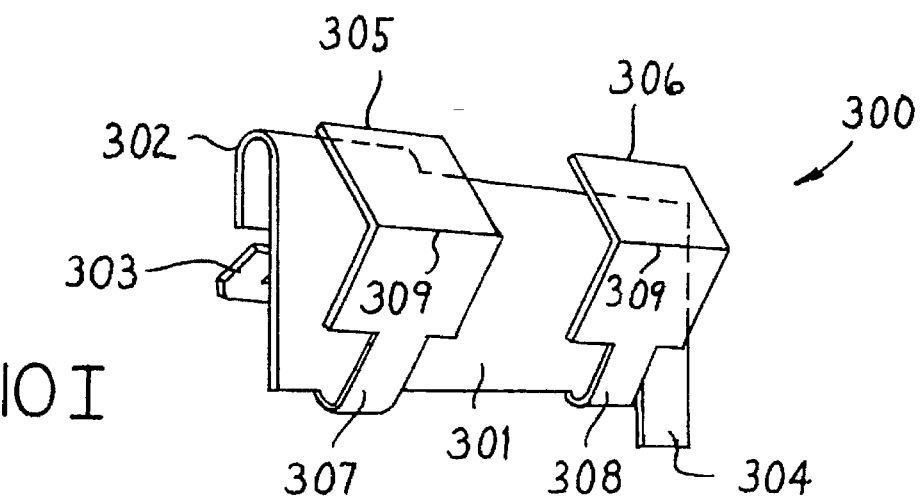
FIG. 10I is an enlarged pictorial view of a bridging contact strip for connecting the front ends of the batteries of FIG. 10.
Figure 10E:
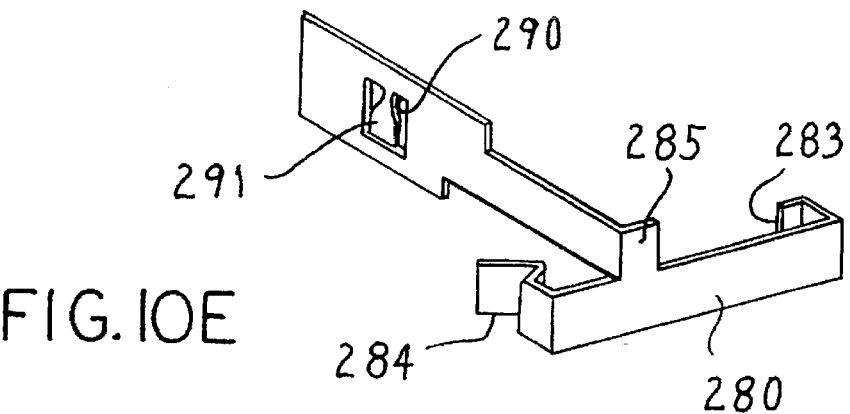
FIG. 10E is an enlarged pictorial view of the battery/switch contact strip of FIG. 10.
Figure 18:
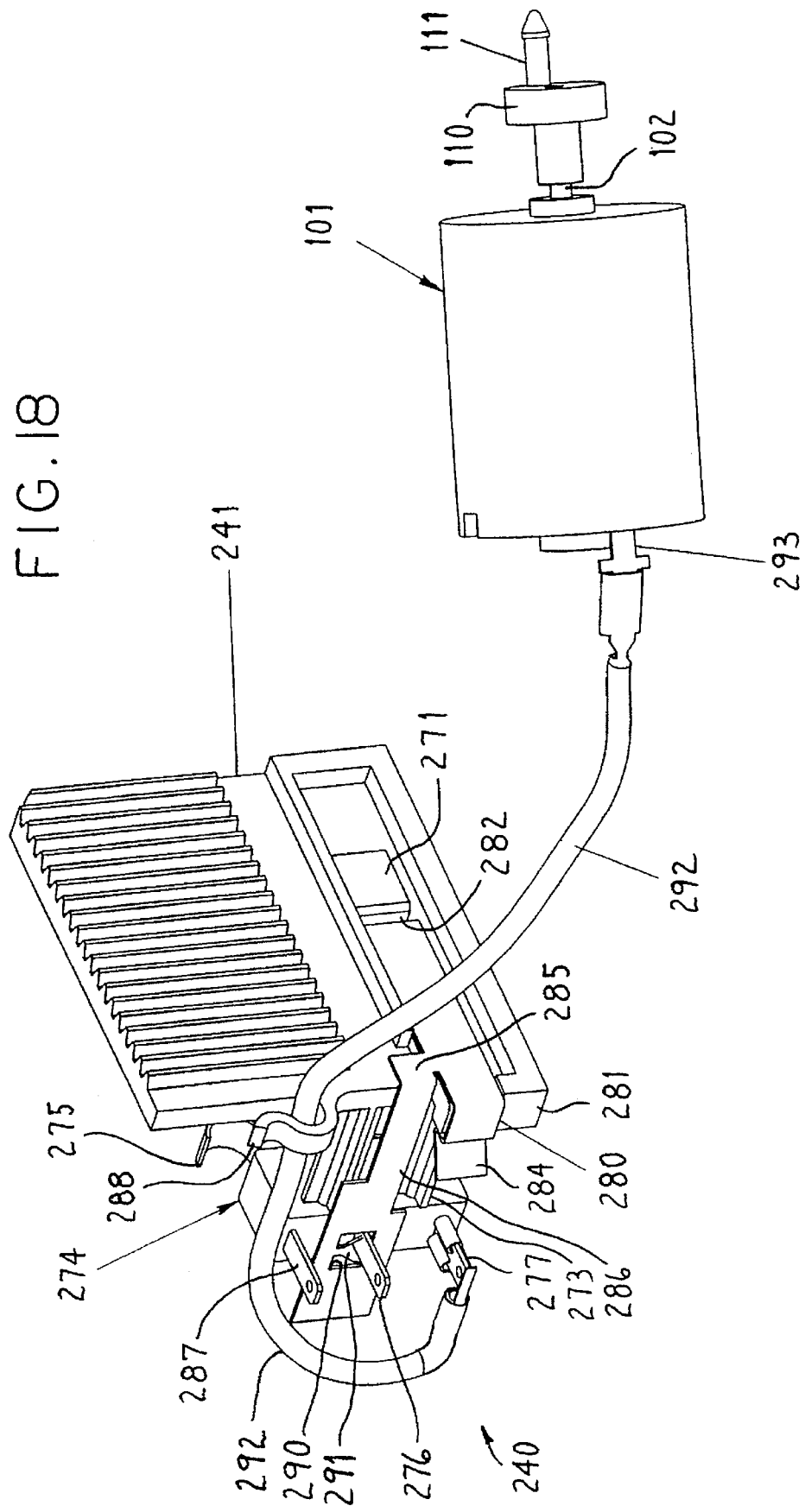
FIG. 18 is an enlarged pictorial view of the slider, switch, and motor of FIG. 10.
Figure 18A:
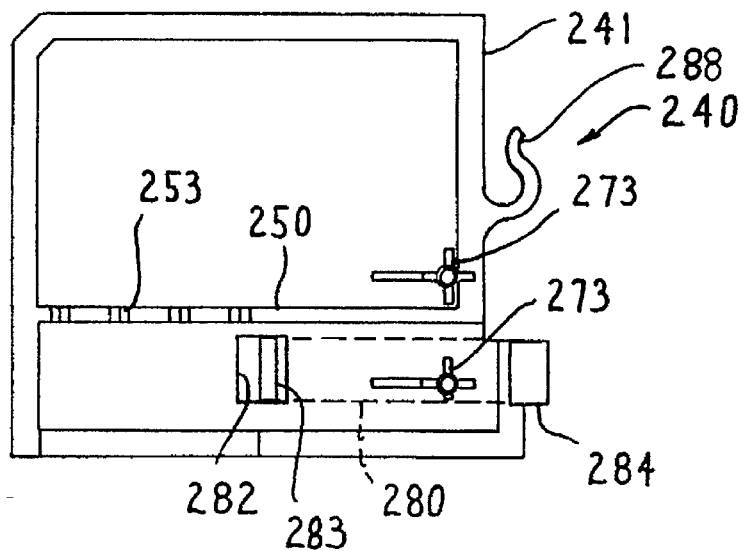
FIG. 18A is a rear view of the slider of FIG. 18.
Figure 18B:
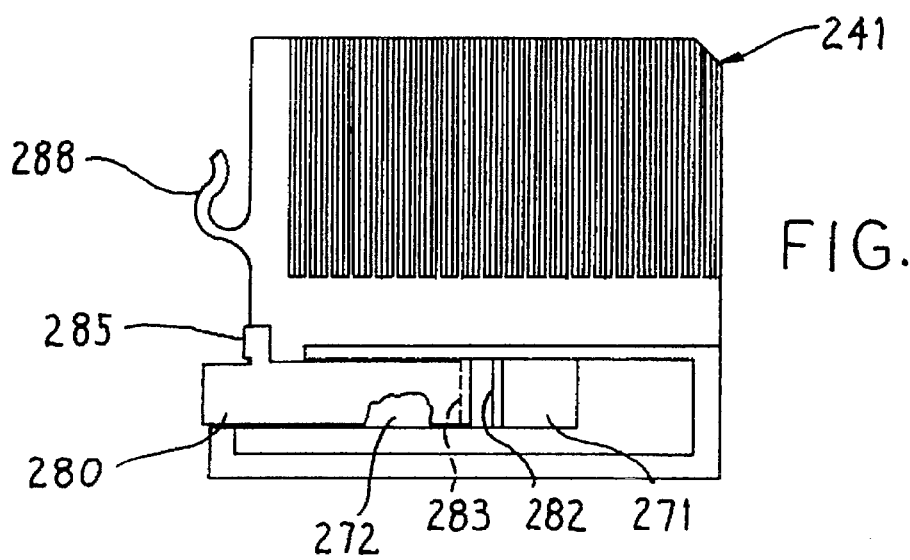
FIG. 18B is a partially broken front view of the slider of FIG. 18.

As seen in FIGS. 10D and 18B, the lower front face of the slider 241 carries slightly forwardly protruding, inboard and outboard (rightward and leftward in FIG. 18B) flat, generally rectangular bosses 270 and 271. Such bosses alternatively face forward through the gap 254 (FIG. 10B) in the front guide rail 242, so the positive rear end of the inboard battery can bear on or oppose alternatively these two bosses, in response to lateral sliding of the slider 241. The front end of the outboard battery bears against the front guide rail 242 and thus cannot contact the slider 241. The front cradle 271 includes a laterally extending front wall 272 closely opposing and substantially covering, as seen from the front, the front ends of the two batteries 263 and 264.

The outboard (leftward in FIGS. 10D and 18) end portion of the slider 241 preferably integrally and fixedly carries a rearward projecting pair of mounting elements 273 (FIGS. 10C and 10D), one spaced over the other, whose rear ends fixedly support a spring loaded switch 274 (FIGS. 10B and 10C). The switch 274 has an actuator 275 which extends toward the closed end wall 143 of the bellows 142 substantially on the axis of the bellows.

An electrical contact, in the form of an elongated metal strip 280 (FIGS. 10E, 18, 18A and 18B), extends along the front outboard portion of the slider 241 outboard of the central boss 271. The contact strip 280 has ends 284 and 283 which respectively extend rearward around the outboard end 281 of the slider lower portion and through a hole 282 through the thickness of the lower portion of the slider 241 just outboard of the boss 271. The inboard end 283 of the strip 280, after passing rearward through the hole 282 wraps around the backside of the slider 241 to form a short tab extending back in the outboard direction (to the right in FIG. 18A) to positively prevent the strip 280 from moving in an outboard direction with respect to the slider 241. Similarly, the outboard end 284 of the strip 280 wraps back and in the inboard direction (leftward in FIG. 18A), around the outboard end of the lower portion of the slider 241 to positively prevent the strip 280 from moving in an inboard direction with respect to the slider 241. Thus, the contact strip 280 in effect hugs the outboard lower portion of the slider 241 to maintain itself fixed thereon.

An upward extension 285 of the strip 280 has an elongate portion 286 (FIG. 18) which is bent rearward and extends rearward, parallel to the switch mounting elements 273 and past the outboard side of the switch 274. The rearward extending elongate portion 286 of the contact strip 280 is spaced from the top and bottom switch contacts 287 and 277 and has a hole 290 through which the middle contact 276 of the switch extends. The rearward extending elongate portion 286 of the contact strip 280 fixedly electrically connects to the middle switch contact 276 by means of an integral jamming tab 291 which extends partway into the hole 290, so as to firmly electrically fix the middle contact 276 of the switch to the contact strip 280.

With the slider 241 in its outboard most position, the inboard battery 264 has its positive end (FIGS. 10B and 18) resting against the non-conductive boss 271 of the slider 241 and out of electrical contact with the contact strip 280. On the other hand, inboard movement of the slider 241 slides the contact strip 280 into engagement with the positive end of the inboard battery 264, to electrically connect the positive terminal of the inboard battery 264 to the switch 274 at its middle terminal 276.

The lower terminal 277 of the switch 274 connects through an insulated wire 292 (FIG. 18) to a terminal 293 protruding from the rear end of the motor 101 (FIG. 18). Thus, with the switch 274 closed (conductive), electrical contact is established between the positive end of the inboard battery 264 and the terminal 293 of the motor 101 (FIG. 10B). A clip 288 on, and preferably integral with, the outboard end portion of the slider 241 (FIG. 18) supports an intermediate position of the insulated wire 292.

A further contact strip 294 (FIG. 10B) extends rearward from the other terminal 295 on the rear end of the motor 101, loosely around the front battery cradle 268 and has an elongate portion 296 extending rearward in spaced relation outboard of the battery cradles 261 and 262, to terminate in a rear end portion 297 (FIGS. 10B and 10D) which lies against the front face of the outboard portion 242L (left portion in FIG. 10B) of the front guide rail 242, so as to engage the negative end of the outboard battery 263 in an electrically conductive manner.

Figure 19:
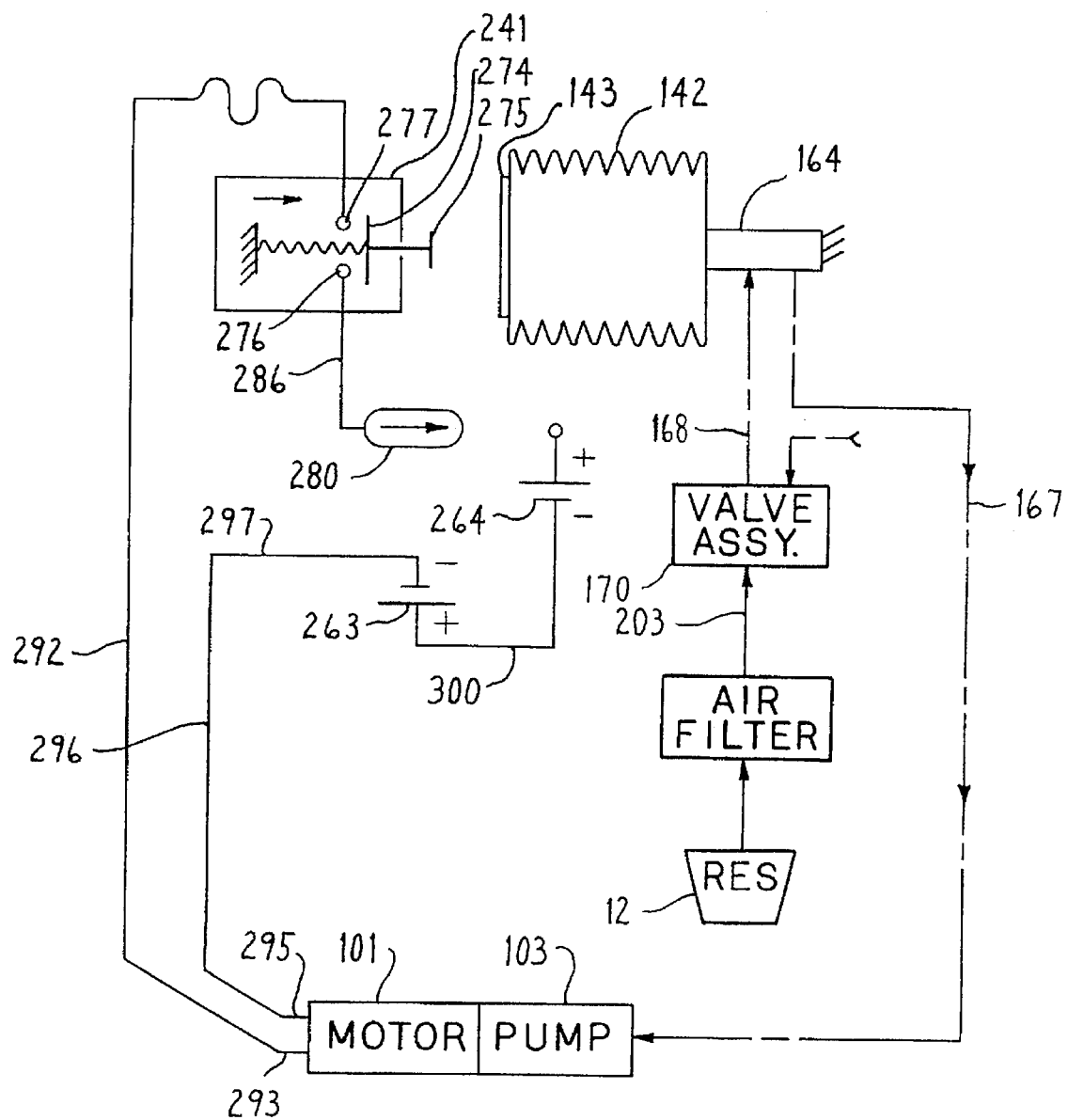
FIG. 19 is a schematic electrical and vacuum path diagram of the system of FIG. 2.

A bridging contact strip 300 (FIGS. 10B and 10I) clips on to the front wall 272 of the front cradle 261, electrically connects the positive end of battery 263 to the negative end of battery 264 and pushes the battery 264 resiliently rearward into the above described alternative engagement with the non-conductive boss 271 of the slider 241 and contact strip 280. The bridging contact strip 300 comprises an upstanding laterally elongate plate 301. The inboard top edge portion of the plate 301 is bent forward and downward to form a clip 302 for gripping the top edge portion of the front cradle front wall 272 therebetween. The bottom of the clip 302 has tabs 303 upset therefrom and angled upward and rearward to grip the outer surface of the front cradle front wall 272 in a tooth-like manner so as to resist unintended removal of the bridging contact strip 300 from such front wall 272. At the diagonally opposite corner of the plate 301, a depending tab 304 extends down to contact the floor 43 of the supporting base 31. Inboard and outboard contacts 305 and 306 are spaced rearward of the plate 301 and are fixedly cantilevered therefrom, bottom edge to bottom edge, by integral, bent, generally V-shaped arms 307 and 308 respectively. The contacts 305 and 306 are here preferably substantially rectangular and are bent in a shallow V-shape along a fold line (as generally indicated at 309), so as to open concavely toward the plate 301. The spring-like arms 307 and 308 resiliently urge the contacts 305 and 306 firmly into electrical contact with the negative end of the inboard battery 264 and positive end of the outboard battery 263 (FIG. 10B) while electrically connecting same in series through the plate 301. This completes the electrical circuit of the apparatus 11, which circuit is also shown schematically in FIG. 19.

With the slider 241 in its outboard FIG. 10C position, the bellows 142 in its relaxed, fully extended position has its closed end near but not contacting the switch actuator 275. This leaves the switch 274 in its closed (circuit completed) condition, but does not energize the pump motor 101 because the at-rest outboard positioned slider 24-1 does not complete a current path through to battery 264. The bellows 142 is in such fully extended position when the air pressure inside it equals the atmospheric pressure outside it.

Figure 20:
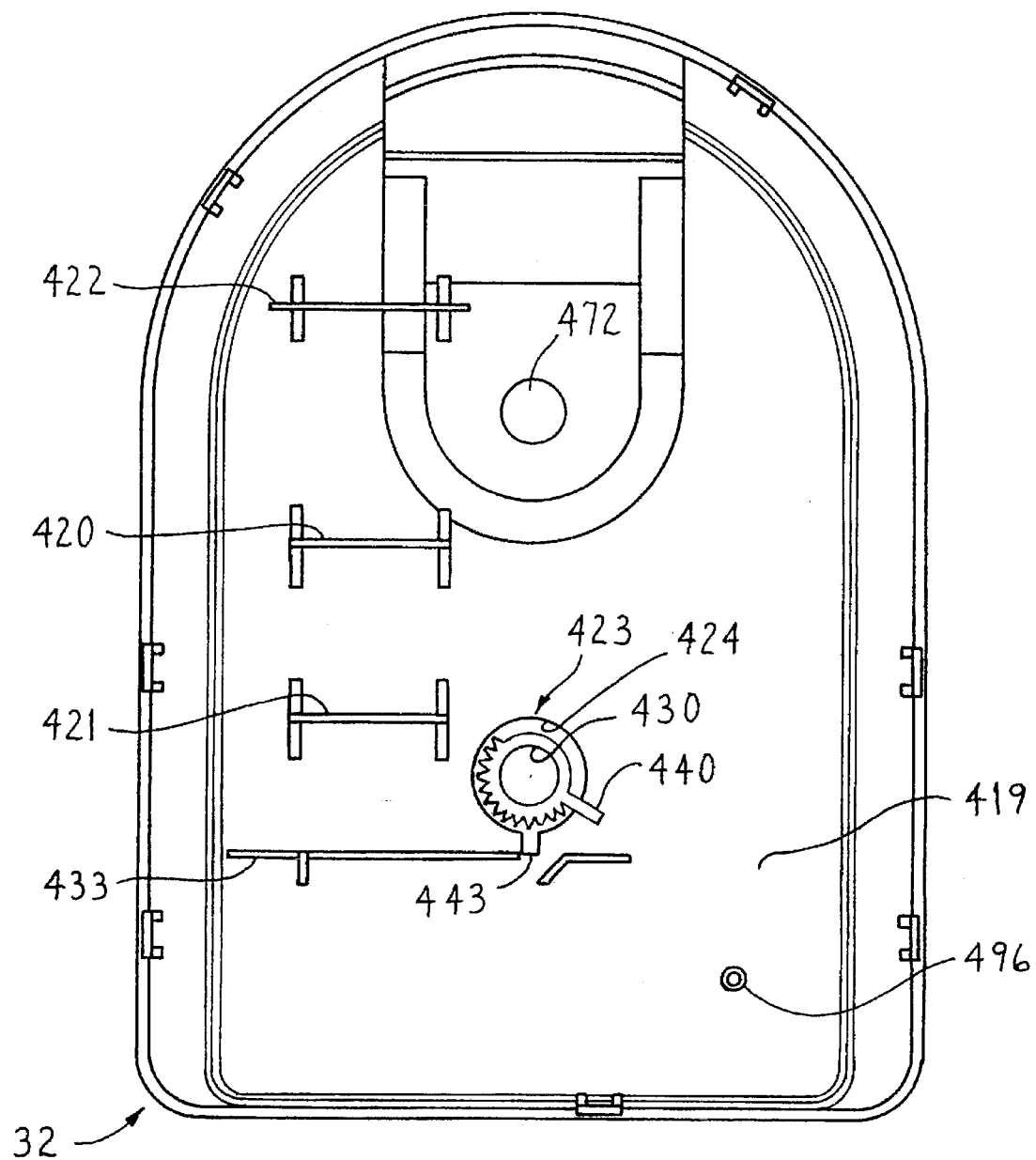
FIG. 20 is a bottom view of the cover of FIG. 2.
Figure 20A:
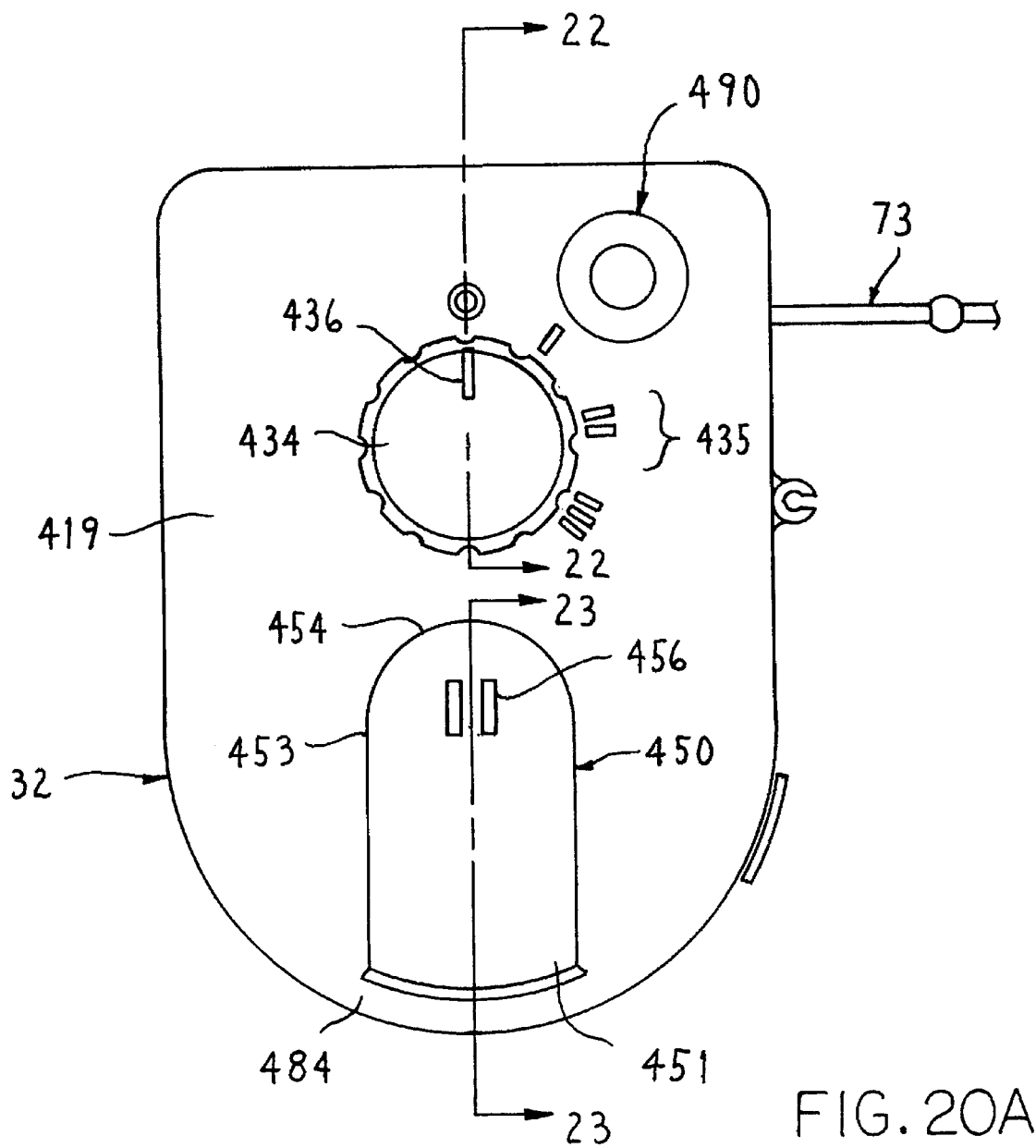
FIG. 20A is a top view thereof.

Actuation of the pump motor 101 requires inboard shifting of the slider 241, to the extent required to complete the circuit through the battery 264 and cause the bellows end 143 to depress the switch actuator to close its internal contacts (not shown). Reduction of the air pressure inside the bellows, by actuation of the vacuum pump 103 connected to it, progressively axially contacts the bellows 142 and retracts its closed end 143 away from the switch 274. When the bellows 142 has contracted sufficient to allow the switch actuator 275 to relax to its normal rest position (shown in solid line in FIG. 10C), the switch 274 opens and thereby electrically disconnects its two lower contacts 276 and 277 to break the circuit therethrough. The downwardly opening, cup-like cover 32 (FIGS. 2 and 20) has a top wall 419 from which fixedly depend a pair of transversely extending fins 420 and 421 (FIG. 20) for positively holding down the batteries 263 and 264 in their cradles 261 and 262 (FIG. 10B). Forward of the front battery fin 420, a further laterally extending fin 422 depends for positively holding down the motor 101 (FIG. 10B).

A manual suction controller 418 (FIGS. 23 and 20) includes a tubular pinion 423 (FIG. 20) which extends downward into the downwardly opening cover 32 through a hole 424 in the rear portion of the cover top wall 419. The pinion 423 is freely rotatable within the hole 424. An internal bearing member 425 (FIG. 10B) is fixedly upstanding from and preferably integral with the floor 43 of the base 31. For strength and to save molding material, the upstanding bearing member 425 here has a generally Y-section core 426, fixedly supporting and generally surrounded by circumferentially spaced, semi-circular section, upstanding bearing elements 427 which act as a radial thrust bearing on the inside wall 430 of the tubular pinion 423, to fix the rotative axis of the tubular pinion 423 with respect to the base 31 and installed cover 32. The rearward semi-circular bearing element 427 arises up from the inboard (rightward in FIG. 10B) portion of the front guide rail 242 above described. The internal bearing member 425 is laterally centered on the base 31 and located just inboard of the rear cradle 262 as seen in FIG. 10B.

Circumferentially spaced, axially extending gear teeth 431 are fixed, preferably integrally, on the outer periphery of the tubular pinion, and here cover about half the circumference thereof. In the assembled apparatus 11, the pinion teeth 431 mesh (FIG. 21) with laterally spaced, vertical rack teeth 432 fixed, preferably integrally, on the upper portion of the front face of the slider 241, so that rotation of the tubular pinion 423 in opposite directions moves the slider 241 in alternate laterally inboard and outboard directions along its guide rails 242 and 243. A third, laterally extending guide rail 433 (FIG. 20) depends from the top of the cover 32 above and parallel to the rearward guide rail 243 upstanding from the floor 43 so that the upper portion of the slider 241 is sandwiched between the tubular pinion 473 and the third guide rail 433 (FIG. 20) depending from the underside of the cover 32. In this way, the tubular pinion 423 positively engages and laterally slides the slider 241 without danger of skipping teeth.

A hand rotatable knob 434 (FIG. 3) is fixed, preferably integrally, coaxially atop the tubular pinion 423, in close spaced relation above the top wall 419 of the cover 32. The top wall 419 of the cover 32 is provided with indicia 435 (FIG. 22), here in the form of numerals 0, I, II and III, fixed around a portion of the periphery of the knob 434 substantially in correspondence to the circumferential extent of teeth 431 on the tubular pinion 423 (here about half the circumference). The indicia 0, I, II and III respectively correspond to successive positions of the slider 241 determined by the detent notches 253 (FIG. 10B) on the back rib 250 thereof, extending from the limiting outboard (pump off) position of the slider 241 in FIG. 21, against outboard stop 244, to the limiting inboard (maximum evacuation) position of the slider corresponding to 241 in FIG. 21A, against inboard stop 245. Thus, by setting an index mark 436 (FIG. 22), circumferentially fixed on the knob, into radial opposition with a desired indicia atop the cover, the user can set the maximum desired vacuum in the reservoir.

The switch actuator 275 (FIG. 10B) and the bellows 142 provide some hysteresis, so that the absolute pressure in the reservoir 12 will rise somewhat before the vacuum pump 103 turns on again, to limit the vacuum pump on/off cycling frequency in normal use to a reasonable rate, for example, to provide at least some time interval between pump-off and pump-on, in normal use.

A flange 440 (FIGS. 21 and 22) extends radially outward from the lower portion of the tubular pinion 423, at one circumferential end of the band of gear teeth thereon. A finger 441 extends upward the outer edge portion of the flange. The finger and flange are integral with the tubular pinion. A keeper tip 442 extends radially outward from the top of the finger 441. The keeper tip 442 and the top of the finger 441 are spaced below the knob 434 by a bit more than the thickness of the top wall 419 of the cover 32. A notch 443 (FIGS. 20 and 22A) radially opens forward into the hole 424 in which the tubular pinion 423 is rotatably received.

To assemble the manual vacuum control knob and tubular pinion on the cover 32, the bottom of the tubular pinion 423 is dropped down into the hole 424 in the top wall 419 of the cover 32, with the flange 440 and tubular finger 441 sliding down through the notch in the cover top wall. Pressing the keeper tip 442 radially inward toward the tubular pinion 423 bends the supporting finger 441 radially inward and allows the keeper tip 442 to drop down through the notch 443 to a location closely below the cover top wall 419, where the finger is free to unbend and thereby move the keeper tip 442 thereon radially outward away from the tubular pinion sufficient to extend slightly radially outward beyond the notch 443, so as to prevent accidental removal of the knob and tubular pinion from the cover 32. The keeper tip 442, being spaced slightly below the cover top wall 419, allows free rotation of the knob and tubular pinion. Although not normally necessary, the knob and tubular pinion can be removed from the cover by a reversal of the above assembly steps, including radially inward bending of the finger to enable the keeper tip to clear the radially outer end of the notch.

In addition, the flange 440 on the tubular pinion 423 also sets positively the limits of the arc through which the knob 434 and tubular pinion 423 can be manually rotated. More particularly, in the "off" rotative position of the knob (position 0), the flange 440 abuts the inboard end of the slider 241, which is then in its outboard position, as seen in FIG. 21.

On the other hand, in the maximum vacuum position (position III) of the knob, the flange hits an abutment fixedly upstanding from the floor 43 (FIG. 21A) just as the slider reaches its most inboard position against the inboard stop 245. In this way, the flange positively prevents accidental over-rotation of the knob so as to positively prevent any tendency of the teeth on the tubular pinion and slider from skipping with respect to each other.

The flange 440 also can be used to assure assembly of the apparatus with the slider and knob in correct relative position. For example, with the slider 241 out of its outboard rest position, the cover 32 is placed atop the base 31. The knob 434 and tubular pinion 423 can only be inserted into the hole 424 in the cover 32 with the flange 440 on the tubular pinion entering the notch 443, which corresponds to the rest or "0" position of the knob. The tubular pinion can only enter the hole 424 if the slider 241 is in its full outboard "rest" position of FIG. 21; otherwise the flange 440 interferes with the slider 241. That way, one is always sure that when the knob 434 is set at "0", namely atmospheric pressure, that indeed the system 10 will provide atmospheric pressure in the reservoir 12.

The valve assembly 170 further includes an actuator lever 450 (FIGS. 2–5 and 23–24A). The actuator lever 450 is generally of inverted cup shape, elongated in the front/rear direction with a convexly rounded semicircular rear end and a more gradually rounded front end with a correspondingly rounded upstanding front ridge 451 (FIG. 24A). The lever 450 has a top wall 452, laterally opposed side walls 453 and a rear wall 454 and front wall 455 (FIGS. 24 and 24A). A pair of parallel, forward/rearward extending slots 456 (FIGS. 2, 24 and 24A) penetrate the top wall 452 near the rear wall 454, in evenly spaced relation between the side walls 453.

Ribs 457 (FIGS. 24 and 24B) preferably integrally depend from the underside of the lever top wall 452 in immediate flanking relation with the slots 456. The ribs 457 have bottom flanges 460 extending inboard toward each other. The inboard ends of flanges 460 at their inner ends carry upstanding walls 461 (FIG. 24B). The upstanding walls 461 are both contoured as shown in FIG. 24A, wherein the top of the wall 461, starting from the rear end thereof rises to define a upstanding hill 462 followed by a valley 463, whereafter the front and portion 464 of the wall rises to lever top wall 452 (FIG. 24C). A upstanding front wall 465 (FIGS. 24B and 24C) closes the front end of the space between the rib 457 and standing wall 461. The rear edge 466 of the resulting generally box-like structure, defined by each rib 457, and its adjacent bottom flange 460 and upstanding wall 461 and front wall 465, is spaced forward substantially from the lever rear wall 454, toward which such box-like structure opens.

The upper end fitting 175 (FIGS. 10C, 16, 17 and 24B) comprises a relief at the upper end of the valve plunger 172, defining a pair of oppositely facing flats 470. Short, coaxial, preferably integral pivot pins 471 protrude perpendicularly from the respective flanges 470. The common length axis of the pins 471 is in a diametral plane of the valve plunger 172. The pins 471 are coplanar with the top end of the valve plunger 172. The outer ends of the pins 471 coincide with the circumference of the upper end of the valve plunger 172, or may be recessed slightly radially inboard therefrom.

The valve plunger 172 thus can be inserted upward through the valve sleeve 171 of the base 31 (FIGS. 15 and 15A), through a corresponding coaxial hole 472 in the top wall 419 of the installed cover 32 (FIGS. 23 and 25), up under the lever 450. The pivot pins 471 are intended to rest on respective ones of the upstanding walls 461 (FIG. 24B), each in its own respective valley 463 (FIG. 23A). Thus, the spring 173 (FIG. 17) not only pulls downward on the valve plunger 172, but also causes the latter, through its pivot pins 471, to pull down the lever 470 snugly against the top wall 452 of the cover 32.

To install the lever 450 on the top of the valve plunger 172 (the receptacle 12 not being on the base 30), the valve plunger 172 is manually pushed upward so that the flats 470 are spaced above the top wall 452 of the cover 32 (for example almost to the level of FIG. 23A), whereupon the rear end portion of the lever 450, to the rear of the ribs 457, is dropped down over the pivot pins 471. The lever 450 is then moved rearward to cause the pivot pins 471 to pass over the top of the hill 461 (FIG. 24C) toward the FIG. 24C dotted line position thereof in the valley 463. Then upward force on the valve plunger 172 is released, allowing it to move downwardly, in response to the urging of its spring, until the pivot pins 471 bottom in the valley 463 as shown in dotted line in FIG. 24C and in solid line in FIG. 24B, as well as in FIG. 23. The downward force of the valve plunger spring 173, acting through the pivot pins 471, thus pulls the lever 450 down against the top wall of the cover 32.

The ribs 457 (FIGS. 24A and 24B) extend forward past the front wall 465 and form a downwardly convexly rounded rocker edge 473 which extends downward somewhat from the bottom flange 460 (though not to the bottom of lever side wall 453). A plate like brace 474 (FIG. 24) depends fixedly and preferably integrally from the top wall 452 of the lever 450 in the region of the lowest part of the rocker edge 473. The brace 474 extends between the ribs 457 and laterally outwardly beyond same so as to maintain the rocker edges fixedly perpendicular to the bottom wall 452 of the lever 450.

Figure 23:
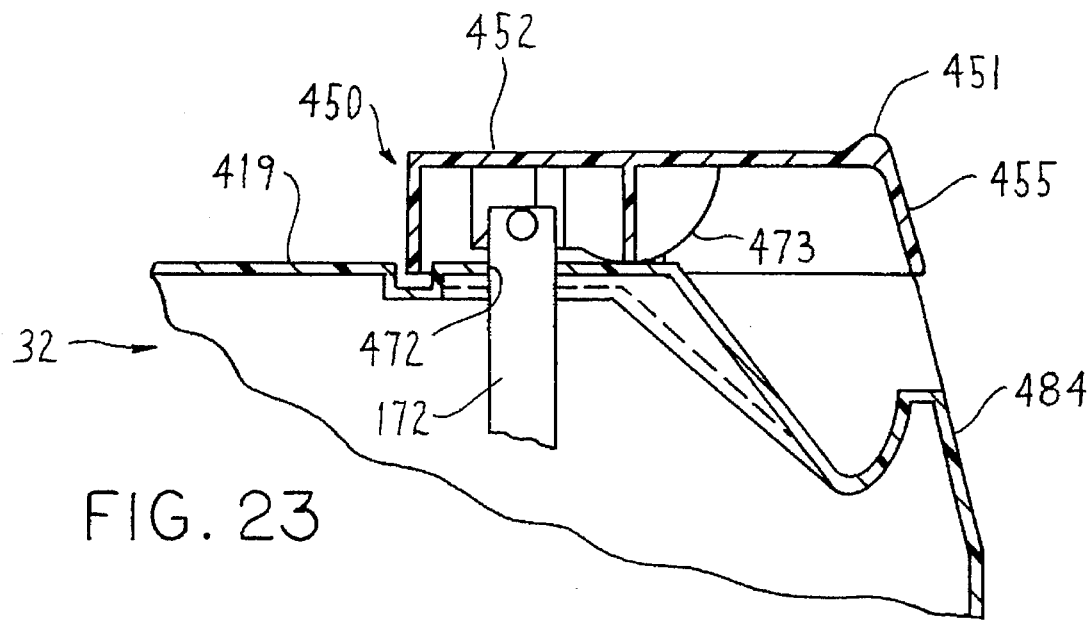
FIG. 23 is a fragmentary enlarged sectional view also substantially taken on the line 23—23 of FIG. 20A and showing the vacuum control lever at rest and the valve plunger down, to close the reservoir blood outlet.
Figure 23A:
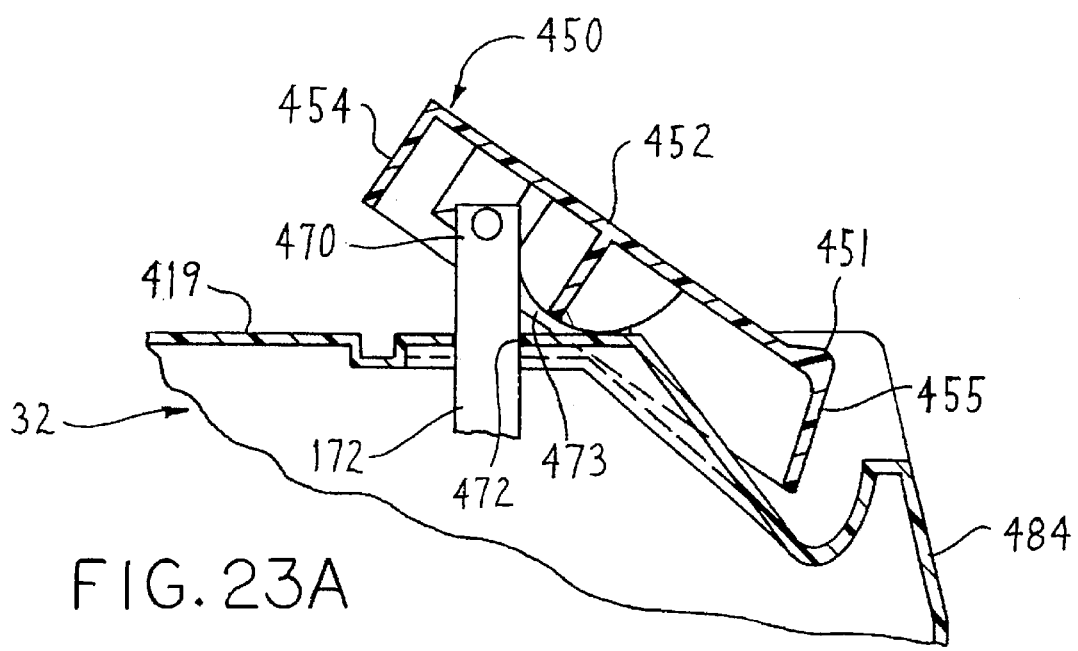
FIG. 23A is a view similar to FIG. 23 but with the vacuum control lever fully pivoted to raise the vacuum plunger and open the blood outlet from the reservoir.

The rocker edges 473 of the ribs 457 are intended to bear against the top wall 419 of the cover 450, to allow pivoting of the lever 450 with respect to the cover 32, between its normal at rest FIG. 23 position and a tilted position in which the front end wall 455 is displaced downward, the rear wall 454 is displaced upward, and the valve plunger 172 is lifted upward. Thus, the rocker edge 473, by pivoting and sliding rearward slightly upon the cover top wall 419, acts as a fulcrum allowing the pivoting lever 450 to pull the valve plunger 172 straight up with respect to the cover 32 and base 31, to shift the valve plunger 172 from its FIGS. 15 and 23 closed position up to its FIGS. 15A and 23A open position. Since the valve plunger 172 must shift straight up and down, coaxial with the valve sleeve 171, and perpendicular to the floor 43 of the base 31 and to the top wall of the installed (FIG. 2) cover 32, the lever must be capable of slight forward/rearward displacement as it pivots, so that its valleys 463, rather than pivoting arcuately upward away from the cover 32, will rise upward generally in a straight vertical line, with the valve plunger pivot pins 471.

Figure 25:
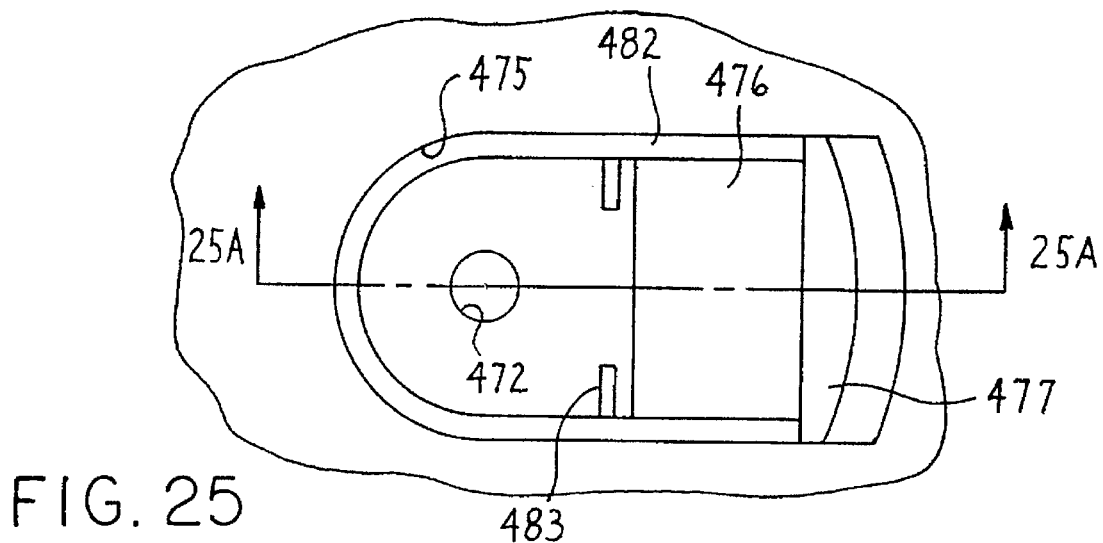
FIG. 25 is a top view of a fragment of the cover without the valve control lever thereon.

In the preferred embodiment shown, the top wall 419 of the cover 32 is provided with a shallow groove 475, generally U-shaped in plan, as seen in FIG. 25. The U-shaped groove 475 has a rounded rear bight portion centered on the hole 472 and legs which extend straight forward therefrom. The U-shaped groove 475 receives the lower edge portion of the convexly rounded rear wall 454 and a portion of the adjoining side walls 453 of the lever 450 in the rest (FIG. 23) position of the lever 450 on the cover 32 (corresponding to the lowered, closed position of the valve plunger 172).

Figure 25A:
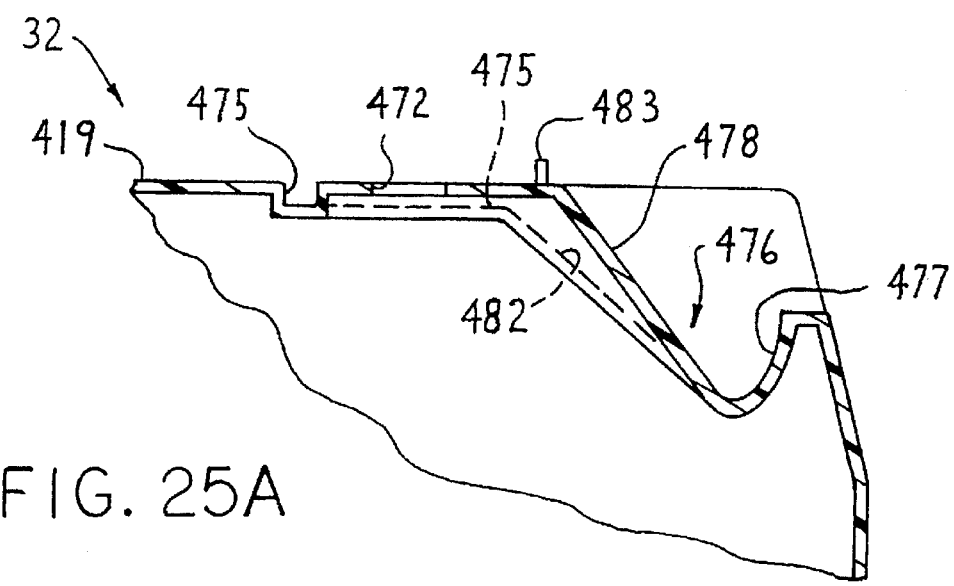
FIG. 25A is a fragmentary sectional view substantially taken on the line 25A—25A of FIG. 25.

To allow downward tilting of the forward half of the lever 450, as seen in FIG. 23A, the front central portion of the cover top wall 419 is depressed to form a generally V-cross section depression 476 (FIGS. 25 and 25A). Preferably the front wall 477 of the depression 476 is concavely curved, the depression being sized to allow downward pivoting thereinto of the front end portion 455 of the lever 450 as seen in FIG. 23A.

Similarly, the forward extending legs of the U-shaped groove 475 slope downward toward the bottom of the depression 476 from a point spaced rearward from the top of the depression rear wall 478. The downward legs portions 482 of the U-shaped groove 475 thus angle down more shallowly to the bottom of the depression 476 than does the rear wall 478 of such depression. The downward angled groove legs 482 accommodate the bottom portions of the side walls 453 of the lever 450 during tilting of the lever from its FIG. 23 to its FIG. 23A position.

Upstanding lugs 483 (FIGS. 25 and 25A), located just inboard of the forward portions 482 of the U-shaped groove 475 and protruding up from the flat portion of the cover top wall 419, bear against the insides of the lever side walls 453 to positively prevent sideways movement of the lever 450 with respect to the cover 32, and in particular to prevent sideways pivoting of the lever 450 about the axis of the valve plunger 172 and hole 472. In the embodiment shown, the forward wall 455 of the lever 450 is curved convexly in plan and slopes forward and downward so that, in its relaxed, horizontal FIG. 23 position, the lever front wall 455 substantially continues the shape of the cover front end wall 484.

Figure 26:
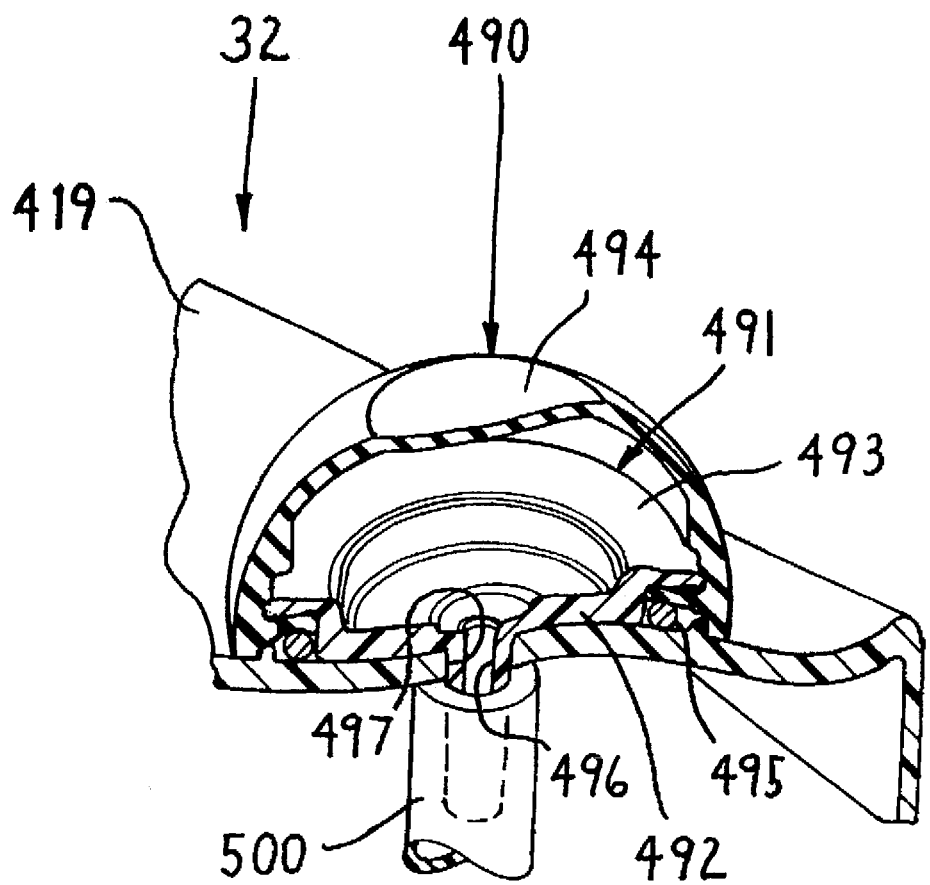
FIG. 26 is an enlarged fragment of FIG. 3 with the vacuum indicator partially broken away to show internal structural detail.

A vacuum indicator 490 (FIGS. 2–5 and 26) is provided for visually indicating the presence or absence of subatmospheric pressure in the reservoir 12. The vacuum indicator here comprises a platter 491 (FIG. 26) with a depressed central portion 492 seated upon the cover top wall 419 and a raised annular rim 493 located substantially in a plane parallel to the plane of the central depressed portion 492. A substantially semispherical, thinned walled, flexible, rubber-like dome 494 resiliently collapses in response to a less than atmospheric pressure therebeneath, by having the upper central portion thereof pulled down into a somewhat toroidal shape.

The dome 494 opens downward and has a bottom rim 495 in the form of a radially inward extending, relatively rigid flange which underlies the rim 493 of the platter 491. The platter 491 has a hollow coaxially depending nipple 496 which extends downward in a tight, sealed press fit through a hole 497 in the top wall 419 of the cover 32 to thereby clamp the inward extending rim 495 of the dome 494 between the overlying rim 493 of the platter 491 and the top of the cover wall 419.

The nipple 496 extends downward beneath the cover top wall 419 for receiving, in snug telescoped relation fixedly thereover, a tube 500 (FIGS. 3 and 26), which leads generally down and forward (as seen in FIG. 3) to sealingly sleeve over a nipple 501 (FIG. 8) upstanding from the floor 43 of the base 31. The nipple 501 communicates, through a hole 502 (FIG. 6) in the floor 43, with the reservoir 12. In this way, the tube 500 connects the dome 490 to the reservoir 12 so that the dome 490 collapses in response to a subatmospheric pressure in the reservoir 12, thereby providing a visible indicator of the subatmospheric pressure in the reservoir 12.

OPERATION

The inventive system 10 may be marketed complete as shown in FIG. 1, with all tube connections made, sterilized in a package, tube connections in FIG. 1, ready for use merely by removal from the package and insertion of the wound drain collector 17 in the patient surgical wound W at the end of surgery and for post operative vacuum draining of the wound. The blood return intravenous cannula 24 can be inserted in the vein of the patient when convenient. The FIG. 1 system 10 may travel with the patient from operating room to intensive care room or hospital room and may be conveniently supported, for example, clamped on the rail R of a gurney or hospital bed in the manner above described with respect to FIG. 5.

The responsible care giver initiates vacuum wound drainage by rotating the knob 434 on the cover 32 from the zero (off) setting to the desired vacuum setting I, II or III. This shifts the slider 241, from its outboard (off) position, inboard to the selected one of its three detent positions which produce the following two results. First, the contact 286 on the slider moves inboard with it, to connect the positive end of the inboard battery 264 to the switch 274. Second, the switch 274 moves inboard with the slider 241, into contact with the closed end of the bellows 142, thereby closing internal contacts (now shown) of the switch 274 and causing the batteries 23 and 264 to start the vacuum pump motor 101 and thus start pumping by the vacuum pump 103.

The actuated vacuum pump 103 draws air from within the bellows 142 and through the bellows manifold 164, the tube 68, the FIG. 15 path through the venting recess 195 of the lowered valve plunger 172, the tube 203 (FIG. 8), air filter assembly 205 and hence from the interior of the reservoir 12.

The reservoir 12 is sealed against ambient air leakage thereinto, at its top by the bottom of the base 31 and at its bottom by the down position of the valve plunger 1714 which seals the standpipe 82. Pumping continues until air pressure drops to the desired level of subatmospheric pressure in the reservoir 12 and bellows 142, axially compressing the bellows 142 enough to deactuate the switch 274, and thus shut off the vacuum pump motor 101. The subatmospheric pressure in the reservoir 12 draws drainage liquid, normally blood with fatty liquid (e.g. lipids) and solids (e.g. small clots, bone fragments, etc.) from the wound W into the reservoir 12. The solids are trapped within the screen cage 90 (FIG. 8) and the liquid enters the portion of the reservoir surrounding the screen cage 90. The level of blood in the reservoir 12 gradually rises. The fatty liquid normally floats in a layer on top of the blood.

As the liquid level gradually rises in the reservoir 12, reducing the air space therein, the air pressure thus rises toward atmospheric pressure in the reservoir 12 and in the bellows 142. The bellows 142 thus progressively expands axially due to its internal spring 146 (FIG. 14) until its closed end 143 reaches and depresses the actuator 275 and actuates the switch 274, which reactuates the vacuum pump 103 to restore the desired level of subatmospheric pressure in the reservoir 12.

Accordingly, the subatmospheric pressure level in the reservoir 12 cycles up and down within a preselected range as flowable material is drawn into the reservoir 12 from the wound W.

Once the reservoir 12 has filled with blood to the desired level, the responsible care giver (e.g. nurse) actuates the lever 450 (FIGS. 23 and 23A) by manual downward pressure on the front end ridge 451 thereof, which pivots the lever 450 from its FIG. 23 to its FIG. 23A position, lifting the valve plunger 172 from its FIG. 15 to its FIG. 15A position.

This lifting of the valve plunger 172 closes the path to the vacuum sensing unit 140 and vacuum pump 103 from the reservoir 12 and vents the reservoir 12 to the atmosphere through the axial vent groove 198, as seen in the upper part of FIG. 15A, to return the reservoir 12 to atmospheric pressure.

This lifting of the valve plunger also lifts the annular flange 184 at the bottom of the valve plunger above the seal washer 182 to open the sinuous liquid path from inside the reservoir 12 down around the valve plunger annular flange 184, up over the top of the standpipe 82, and down through the nipple 83 to the blood outlet tube 21. With pinch plate 25 (FIG. 1) thereof in its open position (not shown), the blood bag 20 fills by gravity from the reservoir 12, thereby draining blood from the reservoir 12 into the blood bag 20.

This lifting of the valve plunger also opens the anti-siphon passage 177 in the valve plunger, between the upper portion of the reservoir 12 and the open bottom of the valve plunger, thereby preventing blood outflowing through the standpipe 82 and blood outlet tube 21 down to the blood bag 20 from siphoning liquid into the standpipe 82 after the liquid level in the reservoir 12 drops to the height of the top of the standpipe 82, so as to prevent siphoning of the usual floating lipids layer into the blood bag.

When the reservoir 12 has sufficiently emptied of blood, leaving the floating lipids layer still in the reservoir 12, the nurse releases the lever 450, thereby allowing the spring 173 to push the valve plunger 172 back down into its lowered FIG. 15 position. This positively and sealingly closes the top of the standpipe 82 and once again connects the reservoir 12 to the vacuum pump 103. This also closes the connection between the reservoir and the axial vent groove 198 and closes the passage 177 between the top of the reservoir 12 and the underside of the valve plunger 172. In other words, this restores the valve plunger to its bottom position of FIG. 15 for vacuum draining of liquid from the wound into the reservoir 12 as above described. Thus, more blood can be vacuum drained from the wound into the reservoir 12.

At the same time, since the blood bag 20 is no longer connected to the reservoir 12 through the standpipe 82, the blood bag 12 can be clamped and a standard blood administration set connected to the blood bag to return the blood collected to the vein of the patient.

The above cycle can be repeated a number of times within the capability of the batteries 263 and 264.

Once vacuum wound drainage is no longer needed, due to sufficient healing of the wound W, the system 10 (FIG. 1) can be disconnected from the patient, by removal of the collector 17 and cannula 24, and the FIG. 1 system 10 can be thrown away in its entirety, thereby avoiding any need for sterilizing of any portion thereof and eliminating any possibility whatsoever of cross contamination between successive patients.

The system 10, minus the blood bag 20 and intravenous cannula 24, can of course be used simply for vacuum wound drainage or the like.

Thus, it will be seen that the entire system is is disposable after use with one patient so as to avoid the need to attempt to sterilize any part of the apparatus for reuse with a second patient. The system is self contained and includes its own onboard power source for repetitively establishing subatmospheric conditions in a wound drainage reservoir, wherein the apparatus does not require any connection to an outside energy supply and the entire system is adapted to travel with the postoperative patient. The apparatus is normally furnished as a one piece unit from which no part need be separable. The reservoir is formed as a simple open top cup sealingly and releasably fixable dependently from an overlying self-contained disposable evacuation unit. The liquid connections (wound drainage liquid in and blood out) are made directly to the reservoir.

Figure 7:
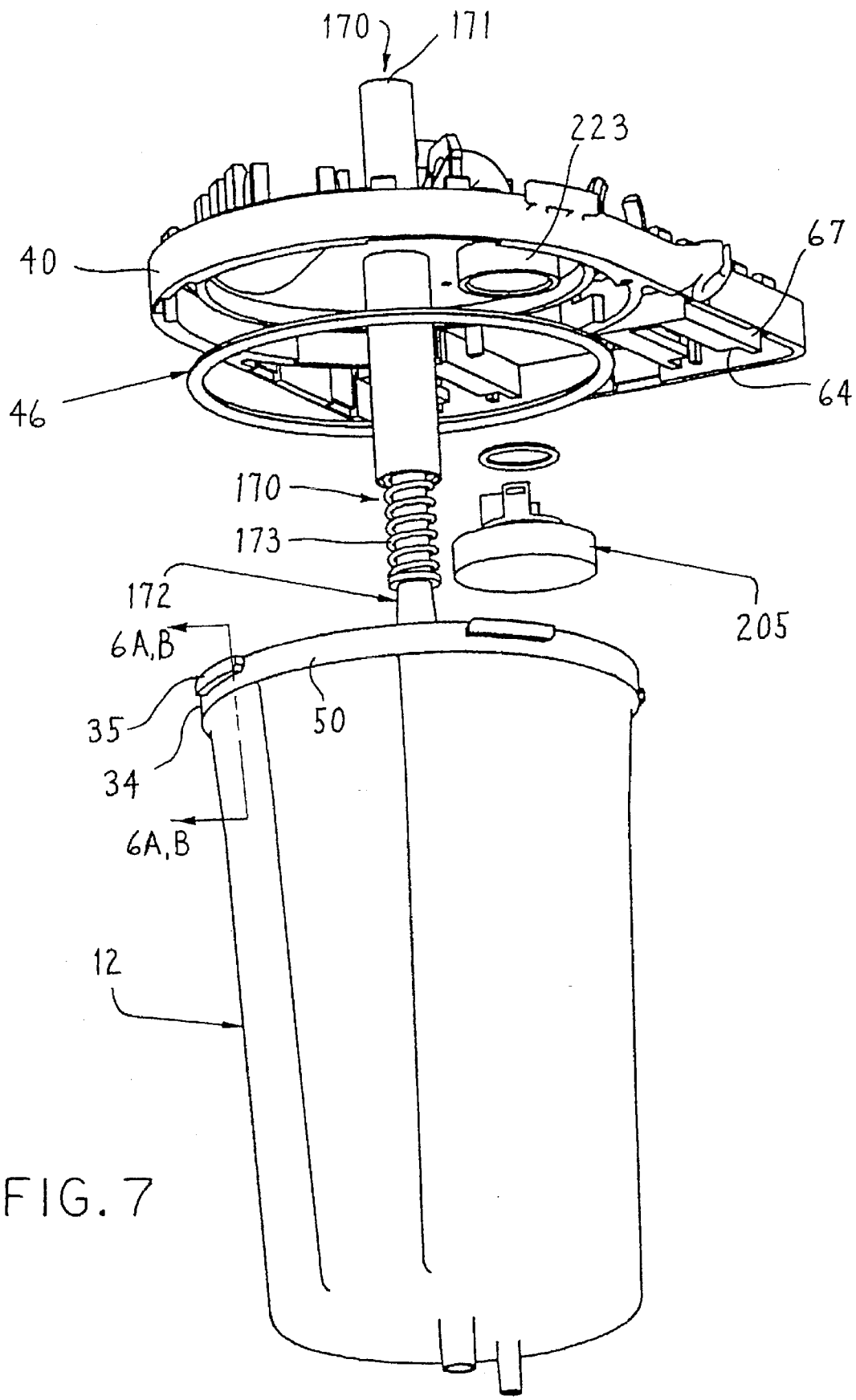
FIG. 7 is an exploded pictorial view of the FIG. 2 system prior to installing operating structure atop the floor of the base.
Figure 9:
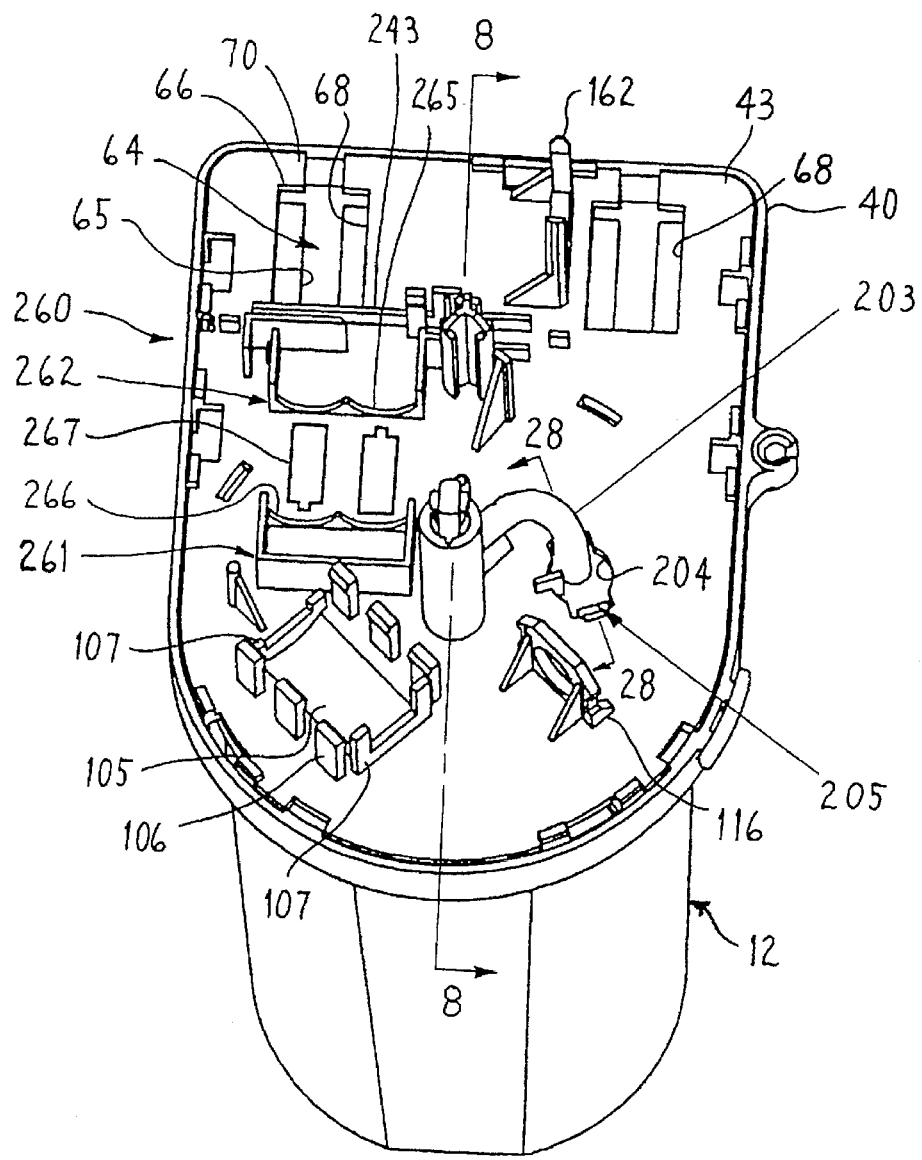
FIG. 9 is a pictorial view of the FIG. 7 apparatus taken from the front and from above.

It is helpful in producing a low cost system 10 to produce the base 31 with the integral structure seen for example, in FIGS. 7 and 9 (excluding the valve plunger and soft tube 203) as a single rigid plastics molded piece. While requiring a complex and hence rather costly mold, same is more than counterbalanced by substantial savings in assembly labor and hardware cost as compared to using separate fasteners to secure the motor, pump, bellows, batteries, contacts, valve plunger, reservoir, and air filter, for example, to the floor 43.

Although a particular preferred embodiment of the invention has been disclosed in detail for illustrative purposes, it will be recognized that variations or modifications of the disclosed apparatus, including the rearrangement of parts, lie within the scope of the present invention.

The embodiments of the invention in which an exclusive property or privilege is claimed are defined as follows:

1. Medical apparatus for vacuum draining a surgical wound on a patient comprising:
    a reservoir evacuable to subatmospheric pressure and means for drawing liquid thereinto from a draining wound;
    an evacuation means for placing the reservoir under subatmospheric pressure and including an evacuation pump for producing a subatmospheric pressure, expandable/contractible means connected in a subatmospheric pressure path with said evacuation pump and reservoir for contraction in response to reduction of air pressure in said reservoir by operation of said evacuation pump, energizing means responsive to contraction of said expandable/contractible means for turning off said pump and responsive to an expansion of said expandable/contractible means for turning on said pump.

2. The apparatus of claim 1 in which said evacuation means includes displaceable means displaceable for changing the pressure range in which said expandable/contractible means maintains said pump on.

3. The apparatus of claim 2 in which said expandable/contractible means comprises a bellows contractible in response to a subatmospheric pressure therein and having a free end moveable in the direction of such contraction, said displaceable means comprising a slider manually moveable in the direction of contraction of said bellows and carrying with it contact means engageable with the free end of said bellows for actuating said evacuation pump to lower the pressure in the reservoir, said slider having a rest position corresponding to atmospheric pressure in said bellows and reservoir and a position displaced from such rest position corresponding to a subatmospheric pressure in the reservoir.

4. The apparatus of claim 3 in which said displaceable means comprises a knob rotatable through a range of positions to select a desired subatmospheric pressure in said reservoir, and interengaging teeth fixed with respect to said knob and slider for slidably displacing said slider in correspondence to a rotation of the knob.

5. The apparatus of claim 4 including a floor from which said reservoir depends, said bellows and slider being supported above said floor, a bearing support upstanding from said floor adjacent to said slider, said knob surmounting a hollow tubular pinion sleeved over said bearing support for rotatably supporting same, the teeth associated with said knob being on said tubular pinion and engaging the teeth on said slider, the teeth on said slider being arranged as a horizontally extending rack.

6. The apparatus of claim 5 including a cover spaced above and overlying the floor, a radially protruding fin on said tubular pinion insertable down through a notch in a pinion receiving hole in said cover for aligning said fin to abut the end of the slider with the slider in its rest position, said knob being rotatable from its rest position to advance said slider by toothed engagement between slider and tubular pinion, a stop upstanding from said floor for blocking further rotation of said fin at the end of tubular pinion rotation and slider advancement to an end position corresponding to the maximum vacuum level in the reservoir.

7. The apparatus of claim 1 including a floor from which said reservoir depends, cradle means fixed with respect to said floor for supporting batteries, a slider and a guide rail fixed with respect to said floor for guiding said slider, an electrical conductor fixed on said slider for sliding therewith along said guide rail, a portion of said guide rail isolating one battery from said slider, said guide rail leaving an opening between a second battery and said electrical conductor on said slider, said electrical conductor extending only part-way along the slider, such that with the slider in its rest position corresponding to atmospheric pressure in the reservoir, the second battery contacts a nonconductive portion of said slider, but with the slider partially advanced in the direction required to evacuate the reservoir, the second battery contacts said electrical conductor on said slider for energizing said evacuation pump until the air pressure in said reservoir drops to a pre-selected level corresponding to the position of said slider.

8. The apparatus of claim 1 in which said energizing means comprises switch means operatively engageable by said expandable/contractible means and actuable in response to expansion of said expandable/contractible means to switch the state of said switch means, battery contact means for engaging and passing electric current from an electric battery, motor means connected to said pump for driving same and electrically connected in circuit with said switch means and battery contact means for causing said pump to reduce air pressure in said expandable/contractible means and reservoir in response to expansion of said expandable/contractible means sufficient to cause said switch means to switch state.

9. The apparatus of claim 8 in which said energizing means further comprises spring means for resiliently expanding said expandable/contractible means upon a rise in air pressure in said expandable/contractible means from subatmospheric pressure toward atmospheric pressure.

10. The apparatus of claim 8 in which said energizing means comprises subatmospheric pressure limit adjusting means in turn comprising relatively shiftable support means carrying said expandable/contractible means and said switch means and actuable for relatively shifting said expandable/contractible means and said switch means and therewith for changing the expansion/contraction dimension of said expandable/contractible means which actuates said switch means, and manually engagable control means operatively connected to said relatively shiftable support means and actuable for relatively shifting said expandable/contractible means and said switch means.

11. The apparatus of claim 1 in which said energizing means comprises switch means operatively engagable with said expandable/contractible means and actuable in response to expansion of said expandable/contractible means for energizing said pump, subatmospheric pressure limit adjusting means in turn comprising relatively shiftable support means carrying said expandable/contractible means and said switch means and actuable for relatively shifting said expandable/contractible means and said switch means and therewith for changing the expanded extent of said expandable/contractible means at which it actuates said switch means, and manually engagable control means operatively connected to said relatively shiftable support means and actuable for relatively shifting said expandable/contractible means and switch means.

12. The apparatus of claim 11 in which said relatively shiftable support means comprises detent means for identifying to the user several discreet points in a range of relative shifting of said switch means and expandable/contractible means at which to set said manually engagable control means for selecting relatively high and low subatmospheric pressure limits at which to turn off said evacuation pump.

13. The apparatus of claim 1 in which said expandable/contractible means comprises a bellows contractible in response to a subatmospheric pressure therein and having a free end moveable in the direction of such contraction for causing said energizing means to turn off said pump, spring means in said bellows prebiased for expanding said bellows to an expanded condition in response to atmospheric pressure in said bellows and reservoir and overcome by a subatmospheric pressure in the reservoir for allowing such contraction of said bellows.

14. The apparatus of claim 1 including a floor from which said reservoir depends, a standpipe opening through the bottom of said reservoir, a tubular valve sleeve extending rigidly down from said floor coaxially with said standpipe, a valve plunger axially moveable in said valve sleeve and having an open lower end coaxially telescopable over said standpipe and capable of maintaining coaxiality with said standpipe.

15. The apparatus of claim 14 in which the tubular valve sleeve includes a hole opening radially therein near and below said floor, said valve plunger having an up position opening said standpipe and connecting said tubular valve sleeve hole through a passage axially downward in said valve plunger to the open bottom end of the valve plunger for preventing siphoning of floating flowable contaminants from a layer in said reservoir into said standpipe due to blood flow from the reservoir down through said standpipe, said valve plunger having a down position closing said hole.

16. The apparatus of claim 14 including a cover spaced above and overlying the floor, and in which said tubular valve sleeve has ports above said floor and below said cover open to the top portion of said reservoir for drawing air therefrom into a suction path, said valve plunger having means in its down position for interconnecting said last mentioned ports and means in its up position for connecting said reservoir to the atmosphere above said cover and blocking said suction port.

17. The apparatus of claim 1 comprising a base defining a normally substantially horizontal floor and an annular flange depending from said floor, a resilient seal ring snugly surrounding said depending annular flange, said reservoir being cup-shaped and having an open top bounded by an annular reservoir rim, said rim having a radially outward extending annular portion, from an outer edge of which arises an axially upward extending annular portion, said axially upward extending portion of said reservoir rim being upwardly slidable over said seal ring and spaced immediately outward from said annular flange depending from said floor for partially radially crushing said seal ring therebetween and therewith to establish an airtight seal of the top of said reservoir to said floor without need to axially crush a seal, cooperating means on said reservoir rim and depending from said floor around and spaced radially outward from said depending annular flange for fixing said reservoir rim to the underside of said floor.

18. The apparatus of claim 17 in which said cooperating means comprise ears extending radially outward from said reservoir rim and ledges fixed with respect to the underside of said floor and extending radially inward toward said reservoir rim, said ledges being circumferentially spaced to allow upward displacement of said ears therepast toward said floor, said reservoir being rotatable to circumferentially slide said ears into radial spaces between corresponding ones at said ledges and the underside of said floor to establish a bayonet connection of said reservoir to the underside of said floor to maintain said reservoir rim in radial seal ring crushing relation with said annular flange depending from said floor.

19. The apparatus of claim 17 in which said reservoir includes a coaxial standpipe opening through the bottom thereof, a tubular valve sleeve extending rigidly down from said floor coaxially with said dependent annular flange and reservoir, and a valve plunger axially moveable in said valve sleeve and having an open lower end coaxially telescopable over said standpipe and capable of maintaining coaxiality with said standpipe during circumferential tightening and loosening movement of said reservoir with respect to said floor.

20. The apparatus of claim 19 including a seal washer on said reservoir bottom around the bottom of said standpipe for sealing contact with the bottom end of the valve plunger to close the top of the standpipe against communication with the interior of the reservoir during vacuum collection of liquid in the said reservoir.

21. The apparatus of claim 1 in which said evacuation means includes a vacuum pump comprising a generally hat-shaped flexible member having a radially outwardly extending brim and a central crown, a fixed bracket open to loosely receive the crown reciprocably therethrough, a rigid cup open toward said bracket, said brim of said flexible member being axially fixedly clamped between said bracket and the open end of said cup, said cup being of sufficient depth as to allow reciprocation of said resilient member crown axially therein for establishing an expansible pumping chamber between said moveable crown and rigid cup, said cup having a closed end wall with an inlet port and an outlet port, inlet and outlet check valves associated with said inlet and outlet ports respectively, resiliently flexible hooks extending from the closed end of said cup in and along the sides thereof to resiliently snap over opposite sides of said bracket for pressing the open end of said cup and said bracket in sandwiching relation against the brim of said hat-shaped flexible member for fixing said brim with respect to said bracket, a push rod fixed to the crown of said hat-shaped flexible member and extending away from said cup open end and bracket, a motor having a rotatable shaft carrying an eccentric and pivotally connected to the free end of said push rod for reciprocating said push rod and thereby said crown of said hat-shaped flexible member for thereby pumping fluid through said pumping chamber, a floor supporting said bracket and motor above said reservoir and means connecting said inlet check valve of said pump to said reservoir for evacuating same.

22. The apparatus of claim 21 in which said motor and pump have central length axes respectively extending along the motor shaft and pump push rod and defining a V-shape, said reservoir being substantially circular as seen from the open end thereof, said floor having a perimeter edge portion generally rounded to correspond to the opposed upper open end of said reservoir, a valve assembly coaxially upstanding in said reservoir and protruding through said floor, the perimeter of said floor adjacent said motor and pump being convexly rounded substantially on a radius from the central axis of said valve assembly, said pump and motor being on opposite sides of said valve assembly and being located radially between said valve member and the perimeter of said floor, said V-shape defined by said motor and pump axes opening toward said valve assembly and pointing over the central portion of said rounded perimeter edge of said floor.

23. The apparatus of claim 1 comprising a suction and control assembly having front and rear portions and normally positioned approximately horizontally and including said evacuation means, said reservoir being open topped and fixed pendently beneath the front portion of said suction and control assembly, the back side of said reservoir and the underside of said suction and control assembly immediately behind said reservoir having surfaces adapted to bear rearward and downward, respectively, against a variety of supports including rails on patient supporting beds and chairs;
clamping means comprising a paddle dependent from said suction and control assembly adjacent to the rear edge thereof and spaced to the rear of said reservoir for pressing forwardly against such a rail, the top edge of said paddle and the bottom of said suction and control assembly having cooperating means manually actuable for moving the paddle forward toward said reservoir for sandwiching such a rail therebetween and responsive to forward pressure on the top edge of said paddle for jam locking the top of said paddle against rearward movement away from such rail and for clamping such rail between said paddle and reservoir.

24. The apparatus of claim 1 comprising a suction and control assembly which includes said evacuation means and from which said reservoir depends, said suction and control assembly including a floor overlying the open top of said reservoir for closing same, an air filter depending from said floor and comprising a shallow upward opening cup, a generally hat-shaped lid having a radially outward extending brim mostly closing the top of said cup while allowing air flow from the reservoir into said cup, said lid being spaced above the bottom wall of said cup to form an air chamber therein, said floor having a depending annular flange, said lid having a crown for sliding snugly upward into said annular flange, air seal means interposed between said crown and the annular flange depending from said floor for preventing air leakage therebetween from above the floor down into said reservoir.

25. The apparatus of claim 24 including a suction port in the top of said crown of said hat-shaped lid for drawing air from said reservoir through the chamber and up into said crown, a hydrophobic and oleophobic filter sheet fixed with respect to said lid for passing air flow but not liquid flow from said reservoir therethrough and into the suction port in said crown, said filter sheet being spaced above a bottom wall of said cup and facing downward thereinto such that any blood or lipids entering but not filling the cup will tend to lie by gravity in spaced relation below said filter sheet, wherein agitation may cause blood and lipids accidentally in said cup to splash up against the filter sheet but wherein gravity will tend to drop such blood and lipids away from said filter sheet to the bottom of said cup and thereby leave said filter sheet capable of passing air from said reservoir up therethrough and into the suction port of said crown.

26. The apparatus of claim 24 in which leaf spring-like fingers extend up from the top of the crown and are generally evenly circumferentially spaced along the perimeter of the crown, upward tapering wedges on the upper outer surface of each finger for snapping over the top of the floor upon insertion of said crown up into said depending annular flange, for positively supporting said air filter beneath said floor.

27. The apparatus of claim 26 in which said brim has openings near the outer edge thereof for receiving air flow from said reservoir, said crown having an upstanding fin engageable in a notch in said floor for positively orienting said air openings in said lid close to and aimed toward the central axis of said reservoir, to permit tipping of said reservoir in any direction with least likelihood of liquid in the reservoir reaching and entering said openings in said lid.

28. Medical apparatus for vacuum draining a surgical wound on a patient comprising:
reservoir evacuable to subatmospheric pressure and means for drawing liquid thereinto from a draining wound;
an evacuation means for placing the reservoir under subatmospheric pressure and including an evacuation pump for producing a subatmospheric pressure, expandable/contractible means connected in a subatmospheric pressure path with said evacuation pump and reservoir for contraction in response to reduction of air pressure in said reservoir by operation of said evacuation pump, energizing means responsive to contraction of said expandable/contractible means for turning off said pump and responsive to an expansion of said expandable/contractible means for turning on said pump;

a suction and control assembly including at least a portion of said evacuation means and having front and rear portions and normally positioned approximately horizontally, said reservoir being fixed pendently beneath a front portion of said suction and control assembly, a back side of said reservoir and an underside of said suction and control assembly immediately behind said reservoir having surfaces adapted to bear rearward and downward, respectively, against a variety of supports including rails on patient supporting beds and chairs;

clamping means comprising a paddle dependent from said suction and control assembly adjacent to a rear edge thereof and spaced to the rear of said reservoir for pressing forwardly against such a rail, the top edge of said paddle and the bottom of said suction and control assembly having cooperating means manually actuable for moving the paddle forward toward said reservoir for sandwiching such a rail therebetween and responsive to forward pressure on the top edge of said paddle for jam locking the top of said paddle against rearward movement away from such rail and for clamping such rail between said paddle and reservoir, said cooperating means comprising a pair of L-shaped arms arising from a fixed elbow spaced above the top of said paddle, the forward extending free ends of said arms having cross pins, said suction and control assembly including a downward facing floor and slot means in said floor for receiving said arms with said cross pins above said slots, said floor including means atop said slots for blocking upward rise of said elbows, such that forcing the top edge of said paddle forward toward a rail to be clamped tight against the back of said reservoir pivots said elbows up against said floor and said pivot pins down against a dropped portion of said floor for jamming said elbows and cross pins fixedly with respect to the floor to prevent unintended rear movement of said paddle away from the rail to be clamped.

29. The apparatus of claim 28 in which said paddle is flexible, allowing downward bending of the bottom portion of said paddle to forcibly engage a rail and push same against said reservoir, and including a strand extending from a lower corner of said paddle, said strand being flexible and capable of wrapping forward and upward partially around a rail, said suction and control assembly having a strand receiving bracket on its periphery adjacent to the rear portion of the reservoir for receiving said strand upward therethrough, said strand having enlarged beads spaced along the length thereof for preventing pulling down of said strand out of said bracket, such that the strand positively prevents lifting of said suction and control assembly up and away from such a rail.

30. Medical apparatus for vacuum draining a surgical wound on a patient comprising:

a reservoir evacuable to subatmospheric pressure and means for drawing liquid thereinto from a draining wound;

an evacuation means for placing the reservoir under subatmospheric pressure and including an evacuation pump for producing a subatmospheric pressure, expandable/contractible means connected in a subatmospheric pressure path with said evacuation pump and reservoir for contraction in response to reduction of air pressure in said reservoir by operation of said evacuation pump, energizing means responsive to contraction of said expandable/contractible means for turning off said pump and responsive to an expansion of said expandable/contractible means for turning on said pump, including a suction and control assembly which includes a cover spaced above a floor and housing at least a portion of said evacuation means, a valve plunger for sealing an outlet of said reservoir and extending up through a hole in said cover, an inverted cup-shaped lever pivotally and releasably engaging the top of said valve plunger as it protrudes above the cover, said cover having a groove to receive the bottom perimeter edge of the inverted cup-shaped lever for preventing rotation of said lever and valve plunger in a plane parallel to said floor, said groove including a deep portion adjacent the front of said cover for downward pivoting of the front end of said lever thereinto, said lever having rocker means engaging the top of said cover in a rocking chair manner for pivotally rocking and sliding forward and rearward on said cover as needed to move said valve plunger axially up and down in response to the rocking movement of said lever.

31. Medical apparatus for vacuum draining a surgical wound on a patient, comprising:

a reservoir evacuable to subatmospheric pressure and means for drawing liquid thereinto from a patient;

an evacuation means for placing the reservoir under subatmospheric pressure and including an evacuation pump for producing a subatmospheric pressure, expandable/contractible means connected in a subatmospheric pressure path with said evacuation pump and reservoir for contraction in response to reduction of air pressure in said reservoir by operation of said evacuation pump, energizing means responsive to contraction of said expansible/contractible means for changing the operating state of said pump to a first state and responsive to expansion of said expandable/contractible means for changing said operating state of said pump to a second state.

32. The apparatus of claim 31 in which said second state is a pump on state.

* * * * *